US012595300B2

(12) United States Patent (10) Patent No.: US 12,595,300 B2
Xia et al. (45) Date of Patent: Apr. 7, 2026

(54) ANTI-HUMAN P40 PROTEIN DOMAIN ANTIBODY AND USE THEREOF

(71) Applicant: Akeso Biopharma, Inc, Zhongshan (CN)

(72) Inventors: Yu Xia, Zhongshan (CN); Zhongmin Maxwell Wang, Zhongshan (CN); Peng Zhang, Zhongshan (CN); Baiyong Li, Zhongshan (CN)

(73) Assignee: Akeso Biopharma, Inc., Zhongshan (CN)

( * ) Notice: Subject to any disclaimer, the term of this patent is extended or adjusted under 35 U.S.C. 154(b) by 1071 days.

(21) Appl. No.: 17/631,797

(22) PCT Filed: Jul. 28, 2020

(86) PCT No.: PCT/CN2020/105039
§ 371 (c)(1),
(2) Date: Jan. 31, 2022

(87) PCT Pub. No.: WO2021/018114
PCT Pub. Date: Feb. 4, 2021

(65) Prior Publication Data
US 2022/0298235 A1 Sep. 22, 2022

(30) Foreign Application Priority Data

| Jul. 30, 2019 | (CN) | ......................... | 201910706137.1 |
| Oct. 29, 2019 | (CN) | ......................... | 201911040745.X |
| Nov. 25, 2019 | (CN) | ......................... | 201911171754.2 |

(51) Int. Cl.
| *C07K 16/24* | (2006.01) |
| *A61K 47/68* | (2017.01) |
| *A61P 37/06* | (2006.01) |
| *A61K 39/00* | (2006.01) |

(52) U.S. Cl.
CPC ........ *C07K 16/244* (2013.01); *A61K 47/6845* (2017.08); *A61P 37/06* (2018.01); *A61K 2039/505* (2013.01); *C07K 2317/31* (2013.01); *C07K 2317/565* (2013.01); *C07K 2317/567* (2013.01); *C07K 2317/76* (2013.01); *C07K 2317/92* (2013.01); *C07K 2319/30* (2013.01)

(58) Field of Classification Search
CPC .............. C07K 16/244; C07K 2317/31; C07K 2317/565; C07K 2317/567; C07K 2317/76; C07K 2317/92; C07K 2319/30; A61K 47/6845; A61K 2039/505; A61P 37/06
See application file for complete search history.

(56) References Cited

U.S. PATENT DOCUMENTS

| 4,816,567 A | 3/1989 | Cabilly |
| 4,946,778 A | 8/1990 | Ladner |
| 5,260,203 A | 11/1993 | Ladner |
| 6,902,734 B2 * | 6/2005 | Giles-Komar ....... C07K 16/244 424/139.1 |
| 10,174,309 B2 * | 1/2019 | Grawunder .............. C12N 5/10 |
| 10,669,336 B2 * | 6/2020 | Frazier ................... A61P 19/00 |

FOREIGN PATENT DOCUMENTS

| CN | 101379085 | | 3/2009 |
| CN | 102177178 | | 9/2011 |
| CN | 103275222 | | 9/2013 |
| CN | 103275222 B | * | 4/2014 |
| CN | 109400709 | | 3/2019 |
| JP | 2014506132 | | 3/2014 |
| WO | 1988001649 | | 1/1988 |
| WO | 2019058345 A2 | | 3/2019 |
| WO | 2019110691 | | 6/2019 |
| WO | 2021018114 | | 2/2021 |

OTHER PUBLICATIONS

Chailyan, A., Marcatili, P. and Tramontano, A. (2011), The association of heavy and light chain variable domains in antibodies: implications for antigen specificity. The FEBS Journal, 278: 2858-2866. https://doi.org/10.1111/j.1742-4658.2011.08207.x (Year: 2011).*
Gniadecki et al., 2016, Combination of antitumour necrosis factor-alpha and anti-interleukin-12/23 antibodies in refractory psoriasis and psoriatic arthritis: a long-term case-series observational study. Br. J. Dermatol, 174: 1145-1146.*
Acierno, et al., "Affinity Maturation Increases the Stability and Plasticity of the Fv Domain of Anti-protein Antibodies", J. Mol. Biol., 374:130-146 (2007).
Altschul, et al., "Basic Local Alignment Search Tool", J. Mol. Biol., 2015:403-410 (1990).
Altschul, et al., "Gapped BLAST and PSI-BLAST: a new generation of protein database search programs", 25(17):33893402 (1997).
Bird, et al., Single-Chain Antigen-Binding Proteins, Science, 242:423-426 (1988).
Chothia, et al., "Canonical Structures for the Hypervariable Regions of Immunoglobulins", J. Mol. Biol., 196:901-917 (1987).
Chothia, et al., "Conformations of immunoglobulin hypervariable regions", Nature, 342:878-883 (1989).
Clark, "Antibody humanization: a case of the 'Emperor's new clothes'?", Immunol. Today, 21(8):397-402 (2000).
Demignot, et al., "Mouse IgG2b monoclonal antibodies Fab, Fc, and Fab/c Preparation and purification of fragments", J. Immunol. Method, 121:209-217 (1989).
Dondelinger, et al., "Understanding the Significance and Implications of Antibody Numbering and Antigen-Binding Surface/Residue Definition", Front. in Immunol., 9(2278): 1-15 (2018).

(Continued)

*Primary Examiner* — Joanne Hama
(74) *Attorney, Agent, or Firm* — Pabst Patent Group LLP

(57) ABSTRACT

Provided is an antibody for the treatment or prevention of autoimmune diseases, comprising a heavy chain variable region represented by SEQ ID NO: 1 or SEQ ID NO: 24, and a light chain variable region represented by SEQ ID NO: 6, SEQ ID NO: 11, SEQ ID NO: 13, SEQ ID NO: 15, SEQ ID NO: 17, or SEQ ID NO: 25.

20 Claims, 11 Drawing Sheets

Specification includes a Sequence Listing.

(56) References Cited

OTHER PUBLICATIONS

Dull, et al., "A Third-Generation Lentivirus Vector with a Conditional Packaging System", J. of Virol., 72(11):8463-8471 (1998).
Gonnet, et al., "Exhaustive Matching of the Entire Protein Sequence Database", Science, 256:1443-1445 (1992).
Hubel, "Animals in the laboratory", Science, 244(4903):409 (1989).
Huston, et al., "Protein engineering of antibody binding sites: Recovery of specific activity in an anti-digoxin single-chain Fv analogue produced in *Escherichia coli*", PNAS, 85:5879-5883 (1988).
Jeltsch-David, et al., "Neuropsychiatric systemic lupus erythematosus and cognitive dysfunction: The MRL-lpr mouse strain as a model", Autoimmunity Reviews, 13:963-973 (2014).
Jones, et al., "Replacing the complemetarity-determing regions in a human antibody with those from a mouse", Nature, 321:522-525 (1986).
Kohler, et al., "Continuous cultures of fused cells secreting antibody of predefined specificity", Nature, 256:495-497 (1975).
Kostelny, et al., "Formation of a bispecific antibody by the use of leucine zippers", The Jouranal of Immunology, 148(5):1547-1553 (1992).
Lefranc, et al., "IMGT unique numbering for immunoglobulin and T cell receptor variable domains and Ig superfamily V-like domains", Developmental and Comparative Immunology, 27:55-77 (2003).
Manetti, et al., "Natural Killer Cell Stimulatory Factor (Interleukin 12 [11,12]) Induces T Helper Type 1 (Thl)-specific Immune Responses and Inhibits the Development of ID4-producing Th Cells", J. Exp. Med., 177(4):1199-1204 (1993).
Martin, et al., "Modeling antibody hypervariable loops: A combined algorithm", PNAS, 86:9268-9272 (1989).

Molecular Cloning, Cold Spring Harbor retreived Feb. 18, 2002.
Oppmann, et al., "Novel p19 Protein Engages IL-12p40 to Form a Cytokine, IL-23, with Biological Activities Similar as Well as Distinct from IL-12", Immunity, 13:715-725 (2000).
Pearson, "Flexible Sequence Similarity Searching with the FASTA3 Program Package", Methods in Molecular Biology, 132:185-2019 (2000).
Pearson, "Rapid and Sensitive Sequence Comparison with FASTP and FASTA", Methods in Enzymology, 183:63-98 (1990).
Pearson, "Using the FASTA Program to Search Protein and DNA Sequence Databases", Methodsin Molecular Biology, 24:307-331 (1994).
Presta, "Antiobdy engineering", Current Opinion in Biotechnology, 3:394-398 (1992).
Reichmann, et al., "Reshaping human antibodies for therapy", Nature, 332:323-327 (1988).
Rosmarin, et al., "The potential of interlukin 12 inhibition in the treatment of psoriasis", J, Drugs Dermatol., 4(3):318-325 (2005). Abstract.
Songsivilai, et al., "Bispecific antibody: a tool for diagnosis and treatment of disease", Clin. Exp. Immunol., 79:315-321 (1990).
Vanvollenhoven, et al., "Efficacy and safety of ustekinumab, an IL-12 and IL-23 inhibitor, in patients with active systemic lupus erythematosus: results of a multicentre, double-blind, phase 2, randomised, controlled study", Lancet, 392:1330-1339 (2018).
Ward, et al., "Binding activites of a repertoire of single immunoglobulin variable domains secreted from *Escherichia coli*", Nature, 341:544-546 (1989).
English Translation of International Search Report for PCT/CN2020/105039 dated Nov. 3, 2020.
Signapore Search Report and Written Opinion: 11202200880T mailed Jan. 28, 2025.
Rudikoff et al., "Single amino acid substitution altering antigenbinding specificity", Proceedings of the National Academy of Sciences, National Academy of Sciences, vol. 79, No. 6, Mar. 1, 1982 (Mar. 1, 1982), pp. 1979-1983.

* cited by examiner

SEQUENCE LISTING

<160> NUMBER OF SEQ ID NOS: 54

<210> SEQ ID NO 1
<211> LENGTH: 119
<212> TYPE: PRT
<213> ORGANISM: Artificial Sequence
<220> FEATURE:
<223> OTHER INFORMATION: Artificially Synthesized Sequence

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Gln Ser Ser Gly Tyr Ser Phe Thr Thr Tyr
                20                  25                  30

Trp Ile Gly Trp Val Arg Gln Met Pro Gly Gln Gly Leu Glu Trp Ile
            35                  40                  45

Gly Ile Met Ser Pro Val Asp Ser Asp Ile Arg Tyr Asn Pro Met Phe
        50                  55                  60

Arg Gly Gln Val Thr Met Ser Val Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Met Val Thr Val Ser Ser
        115

<210> SEQ ID NO 2
<211> LENGTH: 357
<212> TYPE: DNA
<213> ORGANISM: Artificial Sequence
<220> FEATURE:
<223> OTHER INFORMATION: Artificially Synthesized Sequence

<400> SEQUENCE: 2
gaggtgcagc tggtgcagtc tggggccgaa gtgaagaaac ccggggagag tctgaagatc      60
tcatgccaga gctccggcta ctccttcacc acatattgga tcgggtgggt gagacagatg     120
cctggccagg ggctggaatg gatcggaatt atgagcccag tggactccga tattcgctac     180
aaccccatgt ttcgaggcca ggtgacaatg agcgtggaca gtctagttc aactgcttat      240 ctgcagtgga gctccctgaa agccagcgat accgctatgt actattgtgc ccggagaagg     300
cctggacagg gctacttcga cttttggggg cagggaacta tggtgaccgt ctctagt        357

<210> SEQ ID NO 3
<211> LENGTH: 8
<212> TYPE: PRT
<213> ORGANISM: Artificial Sequence
<220> FEATURE:
<223> OTHER INFORMATION: Artificially Synthesized Sequence

<400> SEQUENCE: 3

Gly Tyr Ser Phe Thr Thr Tyr Trp
1               5

<210> SEQ ID NO 4
<211> LENGTH: 8
<212> TYPE: PRT
<213> ORGANISM: Artificial Sequence
<220> FEATURE:
<223> OTHER INFORMATION: Artificially Synthesized Sequence -continued

<400> SEQUENCE: 4

Met Ser Pro Val Asp Ser Asp Ile
1                5

<210> SEQ ID NO 5
<211> LENGTH: 12
<212> TYPE: PRT
<213> ORGANISM: Artificial Sequence
<220> FEATURE:
<223> OTHER INFORMATION: Artificially Synthesized Sequence

<400> SEQUENCE: 5

Ala Arg Arg Arg Pro Gly Gln Gly Tyr Phe Asp Phe
1                5                10

<210> SEQ ID NO 6
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 6

Asp Ile Gln Met Thr Gln Ser Pro Ser Ser Leu Ser Ala Ser Val Gly
1                5                10                15

Asp Arg Val Thr Ile Thr Cys Lys Ala Ser Gln Asn Val Gly Ser Trp
            20                25                30

Leu Ala Trp Tyr Gln Gln Lys Pro Gly Lys Ala Pro Lys Ser Leu Ile
        35                40                45

Tyr Ser Ala Ser Ser Arg Gln Ser Gly Val Pro Ser Arg Phe Ser Gly
        50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Tyr Asp Ile Tyr Pro Phe
                85                90                95

Thr Phe Gly Gln Gly Thr Lys Leu Glu Ile Lys
            100                105

<210> SEQ ID NO 7
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 7
gatattcaga tgacccagag cccttcaagc ctgtccgcaa gcgtcgggga tagagtgacc        60
attacctgta aagcaagcca gaacgtggga agctggctgg cctggtacca gcagaagcca       120
ggcaaagcac ccaagtctct gatctatagt gcaagctccc ggcagtcagg agtgccaagc       180
agattcagtg gctcagggag cggaacagac tttaccctga caatctctag tctgcagcct       240
gaggacttcg caacttacta ttgccagcag tacgatatct acccattcac atttggccag       300
gggactaaac tggagatcaa g                                                 321

<210> SEQ ID NO 8
<211> LENGTH: 6
<212> TYPE: PRT
<213> ORGANISM: Artificial Sequence
<220> FEATURE:
<223> OTHER INFORMATION: Artificially Synthesized Sequence

<400> SEQUENCE: 8

Gln Asn Val Gly Ser Trp
1               5

<210> SEQ ID NO 9
<211> LENGTH: 3
<212> TYPE: PRT
<213> ORGANISM: Artificial Sequence
<220> FEATURE:
<223> OTHER INFORMATION: Artificially Synthesized Sequence

<400> SEQUENCE: 9

Ala Ser Ser
1

<210> SEQ ID NO 10
<211> LENGTH: 9
<212> TYPE: PRT
<213> ORGANISM: Artificial Sequence
<220> FEATURE:
<223> OTHER INFORMATION: Artificially Synthesized Sequence

<400> SEQUENCE: 10

Gln Gln Tyr Asp Ile Tyr Pro Phe Thr
1               5

<210> SEQ ID NO 11
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 11

Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Gly Ser Trp
                20                  25                  30

Leu Ala Trp Tyr Gln Gln Lys Pro Gly Gln Ala Pro Arg Ser Leu Ile
        35                  40                  45

Tyr Ala Ala Ser Asn Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys
            100                 105

<210> SEQ ID NO 12
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 12
gagatcgtcc tgacacagag tcctgctacc ctgagcgctt ccccaggaga gagggcaacc        60
atctcctgcc gcgcctctca gagcgttggc tcctggctgg cttggtacca gcagaagcca       120
ggccaggcac cccgaagcct gatctatgcc gcttctaatc tgcagagcgg gattcccgct       180
agattctctg gcagtgggtc aggaacagac tttaccctga caatctcaag cctggagcct       240

-continued

```
gaagatttcg ccgtgtacta ttgccagcag tacaacatct acccatatac atttggccag      300
gggactcggc tggagatcaa g                                                 321
```

<210> SEQ ID NO 13
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 13

```
Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Ser Ser Trp
            20                  25                  30

Leu Ala Trp Tyr Gln Gln Lys Pro Gly Gln Ala Pro Arg Ser Leu Ile
        35                  40                  45

Tyr Ser Ala Ser Asn Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys
            100                 105
```

<210> SEQ ID NO 14
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 14

```
gagatcgtcc tgacacagag tcctgctacc ctgagcgctt ccccaggaga gagggcaacc       60
atctcctgcc gcgcctctca gagcgttagc tcctggctgg cttggtacca gcagaagcca      120
ggccaggcac cccgaagcct gatctattcc gcttctaatc tgcagagcgg gattcccgct      180
agattctctg gcagtgggtc aggaacagac tttaccctga caatctcaag cctggagcct      240
gaagatttcg ccgtgtacta ttgccagcag tacaacatct acccatatac atttggccag      300
gggactcggc tggagatcaa g                                                 321
```

<210> SEQ ID NO 15
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 15

```
Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Ser Ser Trp
            20                  25                  30

Leu Ala Trp Tyr Gln Gln Lys Pro Gly Gln Ala Pro Arg Ser Leu Ile
        35                  40                  45

Tyr Ala Ala Ser Asn Arg Gln Ser Gly Ile Pro Ala Arg Phe Ser Gly
    50                  55                  60
```

```
Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys
            100                 105
```

```
<210> SEQ ID NO 16
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 16
gagatcgtcc tgacacagag tcctgctacc ctgagcgctt ccccaggaga gagggcaacc        60
atctcctgcc gcgcctctca gagcgttagc tcctggctgg cttggtacca gcagaagcca       120
ggccaggcac cccgaagcct gatctatgcc gcttctaatc ggcagagcgg gattcccgct       180
agattctctg gcagtgggtc aggaacagac tttaccctga caatctcaag cctggagcct       240
gaagatttcg ccgtgtacta ttgccagcag tacaacatct acccatatac atttggccag       300
gggactcggc tggagatcaa g                                                 321
```

```
<210> SEQ ID NO 17
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 17

Glu Ile Val Leu Thr Gln Ser Pro Ala Thr Leu Ser Ala Ser Pro Gly
1                   5                   10                  15

Glu Arg Ala Thr Ile Ser Cys Arg Ala Ser Gln Ser Val Ser Ser Trp
                20                  25                  30

Leu Ala Trp Tyr Gln Gln Lys Pro Gly Gln Ala Pro Arg Ser Leu Ile
            35                  40                  45

Tyr Ala Ala Ser Asn Leu Gln Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Phe
                85                  90                  95

Thr Phe Gly Gln Gly Thr Arg Leu Glu Ile Lys
            100                 105
```

```
<210> SEQ ID NO 18
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 18
gagatcgtcc tgacacagag tcctgctacc ctgagcgctt ccccaggaga gagggcaacc        60
atctcctgcc gcgcctctca gagcgttagc tcctggctgg cttggtacca gcagaagcca       120
ggccaggcac cccgaagcct gatctatgcc gcttctaatc tgcagagcgg gattcccgct       180
```

-continued

```
agattctctg gcagtgggtc aggaacagac tttaccctga caatctcaag cctggagcct      240
gaagatttcg ccgtgtacta ttgccagcag tacaacatct acccatttac atttggccag      300
gggactcggc tggagatcaa g                                                 321
```

```
<210> SEQ ID NO 19
<211> LENGTH: 6
<212> TYPE: PRT
<213> ORGANISM: Artificial Sequence
<220> FEATURE:
<223> OTHER INFORMATION: Artificially Synthesized Sequence

<400> SEQUENCE: 19

Gln Ser Val Gly Ser Trp
1               5

<210> SEQ ID NO 20
<211> LENGTH: 6
<212> TYPE: PRT
<213> ORGANISM: Artificial Sequence
<220> FEATURE:
<223> OTHER INFORMATION: Artificially Synthesized Sequence

<400> SEQUENCE: 20

Gln Ser Val Ser Ser Trp
1               5

<210> SEQ ID NO 21
<211> LENGTH: 3
<212> TYPE: PRT
<213> ORGANISM: Artificial Sequence
<220> FEATURE:
<223> OTHER INFORMATION: Artificially Synthesized Sequence

<400> SEQUENCE: 21

Ala Ser Asn
1

<210> SEQ ID NO 22
<211> LENGTH: 9
<212> TYPE: PRT
<213> ORGANISM: Artificial Sequence
<220> FEATURE:
<223> OTHER INFORMATION: Artificially Synthesized Sequence

<400> SEQUENCE: 22

Gln Gln Tyr Asn Ile Tyr Pro Tyr Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Artificially Synthesized Sequence

<400> SEQUENCE: 23

Gln Gln Tyr Asn Ile Tyr Pro Phe Thr
1               5

<210> SEQ ID NO 24
<211> LENGTH: 119
<212> TYPE: PRT
<213> ORGANISM: Artificial Sequence
<220> FEATURE:
<223> OTHER INFORMATION: Artificially Synthesized Sequence
```

```
<400> SEQUENCE: 24

Glu Val Gln Leu Val Gln Ser Gly Ala Glu Val Lys Lys Pro Gly Glu
1               5                   10                  15

Ser Leu Lys Ile Ser Cys Gln Ser Ser Gly Tyr Thr Phe Thr Ser Tyr
            20                  25                  30

Trp Ile Gly Trp Val Arg Gln Met Pro Gly Gln Gly Leu Glu Trp Ile
            35                  40                  45

Gly Ile Met Ser Pro Val Asp Ser Asp Ile Arg Tyr Asn Pro Met Phe
        50                  55                  60

Arg Gly Gln Val Thr Met Ser Val Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Met Val Thr Val Ser Ser
        115

<210> SEQ ID NO 25
<211> LENGTH: 107
<212> TYPE: PRT
<213> ORGANISM: Artificial Sequence
<220> FEATURE:
<223> OTHER INFORMATION: Artificially Synthesized Sequence

<400> SEQUENCE: 25

Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Gly Thr Trp
            20                  25                  30

Val Ala Trp Tyr Gln Gln Lys Pro Gly Gln Ala Pro Arg Ser Leu Ile
            35                  40                  45

Tyr Ala Ala Ser Asn Leu Gln Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys
            100                 105

<210> SEQ ID NO 26
<211> LENGTH: 8
<212> TYPE: PRT
<213> ORGANISM: Artificial Sequence
<220> FEATURE:
<223> OTHER INFORMATION: Artificially Synthesized Sequence

<400> SEQUENCE: 26

Gly Tyr Thr Phe Thr Ser Tyr Trp
1               5

<210> SEQ ID NO 27
<211> LENGTH: 6
<212> TYPE: PRT
<213> ORGANISM: Artificial Sequence
<220> FEATURE:
<223> OTHER INFORMATION: Artificially Synthesized Sequence

<400> SEQUENCE: 27
```

```
Gln Ser Val Gly Thr Trp
1               5

<210> SEQ ID NO 28
<211> LENGTH: 3
<212> TYPE: PRT
<213> ORGANISM: Artificial Sequence
<220> FEATURE:
<223> OTHER INFORMATION: Artificially Synthesized Sequence

<400> SEQUENCE: 28

Ala Ala Ser
1

<210> SEQ ID NO 29
<211> LENGTH: 25
<212> TYPE: PRT
<213> ORGANISM: Artificial Sequence
<220> FEATURE:
<223> OTHER INFORMATION: Artificially Synthesized Sequence

<400> SEQUENCE: 29

Glu Val Gln Leu Val Gln Ser Gly Ala Glu Val Lys Lys Pro Gly Glu
1               5                   10                  15

Ser Leu Lys Ile Ser Cys Gln Ser Ser
            20                  25

<210> SEQ ID NO 30
<211> LENGTH: 17
<212> TYPE: PRT
<213> ORGANISM: Artificial Sequence
<220> FEATURE:
<223> OTHER INFORMATION: Artificially Synthesized Sequence

<400> SEQUENCE: 30

Ile Gly Trp Val Arg Gln Met Pro Gly Gln Gly Leu Glu Trp Ile Gly
1               5                   10                  15

Ile

<210> SEQ ID NO 31
<211> LENGTH: 38
<212> TYPE: PRT
<213> ORGANISM: Artificial Sequence
<220> FEATURE:
<223> OTHER INFORMATION: Artificially Synthesized Sequence

<400> SEQUENCE: 31

Arg Tyr Asn Pro Met Phe Arg Gly Gln Val Thr Met Ser Val Asp Lys
1               5                   10                  15

Ser Ser Ser Thr Ala Tyr Leu Gln Trp Ser Ser Leu Lys Ala Ser Asp
            20                  25                  30

Thr Ala Met Tyr Tyr Cys
        35

<210> SEQ ID NO 32
<211> LENGTH: 11
<212> TYPE: PRT
<213> ORGANISM: Artificial Sequence
<220> FEATURE:
<223> OTHER INFORMATION: Artificially Synthesized Sequence

<400> SEQUENCE: 32

Trp Gly Gln Gly Thr Met Val Thr Val Ser Ser
1               5                   10
```

<210> SEQ ID NO 33
<211> LENGTH: 26
<212> TYPE: PRT
<213> ORGANISM: Artificial Sequence
<220> FEATURE:
<223> OTHER INFORMATION: Artificially Synthesized Sequence

<400> SEQUENCE: 33

Glu Ile Val Leu Thr Gln Ser Pro Ala Thr Leu Ser Ala Ser Pro Gly
1               5                   10                  15

Glu Arg Ala Thr Ile Ser Cys Arg Ala Ser
            20                  25

<210> SEQ ID NO 34
<211> LENGTH: 17
<212> TYPE: PRT
<213> ORGANISM: Artificial Sequence
<220> FEATURE:
<223> OTHER INFORMATION: Artificially Synthesized Sequence

<400> SEQUENCE: 34

Val Ala Trp Tyr Gln Gln Lys Pro Gly Gln Ala Pro Arg Ser Leu Ile
1               5                   10                  15

Tyr

<210> SEQ ID NO 35
<211> LENGTH: 36
<212> TYPE: PRT
<213> ORGANISM: Artificial Sequence
<220> FEATURE:
<223> OTHER INFORMATION: Artificially Synthesized Sequence

<400> SEQUENCE: 35

Asn Leu Gln Ser Gly Ile Pro Ala Arg Phe Ser Gly Ser Gly Ser Gly
1               5                   10                  15

Thr Asp Phe Thr Leu Thr Ile Ser Ser Leu Glu Pro Glu Asp Phe Ala
            20                  25                  30

Val Tyr Tyr Cys
        35

<210> SEQ ID NO 36
<211> LENGTH: 10
<212> TYPE: PRT
<213> ORGANISM: Artificial Sequence
<220> FEATURE:
<223> OTHER INFORMATION: Artificially Synthesized Sequence

<400> SEQUENCE: 36

Phe Gly Gln Gly Thr Arg Leu Glu Ile Lys
1               5                   10

<210> SEQ ID NO 37
<211> LENGTH: 357
<212> TYPE: DNA
<213> ORGANISM: Artificial Sequence
<220> FEATURE:
<223> OTHER INFORMATION: Artificially Synthesized Sequence

<400> SEQUENCE: 37
gaggtgcagc tggtgcagtc tggggccgaa gtgaagaaac ccgggggagag tctgaagatc      60 tcatgccaga gctccggcta caccttcacc tcatattgga tcgggtgggt gagacagatg     120
cctggccagg ggctggaatg gatcggaatt atgagcccag tggactccga tattcgctac     180

-continued

```
aaccccatgt ttcgaggcca ggtgacaatg agcgtggaca agtctagttc aactgcttat      240
ctgcagtgga gctccctgaa agccagcgat accgctatgt actattgtgc ccggagaagg      300
cctggacagg gctacttcga cttttggggg cagggaacta tggtgaccgt ctctagt        357

<210> SEQ ID NO 38
<211> LENGTH: 321
<212> TYPE: DNA
<213> ORGANISM: Artificial Sequence
<220> FEATURE:
<223> OTHER INFORMATION: Artificially Synthesized Sequence

<400> SEQUENCE: 38
gagatcgtcc tgacacagag tcctgctacc ctgagcgctt ccccaggaga gagggcaacc       60
atctcctgcc gcgcctctca gagcgttggc acctgggtgg cttggtacca gcagaagcca      120
ggccaggcac cccgaagcct gatctatgcc gcttctaatc tgcagagcgg gattcccgct      180
agattctctg gcagtgggtc aggaacagac tttaccctga caatctcaag cctggagcct      240
gaagatttcg ccgtgtacta ttgccagcag tacaacatct acccatatac atttggccag      300
gggactcggc tggagatcaa g                                                321

<210> SEQ ID NO 39
<211> LENGTH: 449
<212> TYPE: PRT
<213> ORGANISM: Artificial Sequence
<220> FEATURE:
<223> OTHER INFORMATION: Artificially Synthesized Sequence

<400> SEQUENCE: 39

Glu Val Gln Leu Val Gln Ser Gly Ala Glu Val Lys Lys Pro Gly Glu
1               5                   10                  15

Ser Leu Lys Ile Ser Cys Gln Ser Ser Gly Tyr Thr Phe Thr Ser Tyr
                20                  25                  30

Trp Ile Gly Trp Val Arg Gln Met Pro Gly Gln Gly Leu Glu Trp Ile
            35                  40                  45

Gly Ile Met Ser Pro Val Asp Ser Asp Ile Arg Tyr Asn Pro Met Phe
        50                  55                  60

Arg Gly Gln Val Thr Met Ser Val Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

-continued

```
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

<210> SEQ ID NO 40
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 40

```
Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Gly Thr Trp
                20                  25                  30

Val Ala Trp Tyr Gln Gln Lys Pro Gly Gln Ala Pro Arg Ser Leu Ile
        35                  40                  45

Tyr Ala Ala Ser Asn Leu Gln Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 26
<212> TYPE: PRT
<213> ORGANISM: Artificial Sequence
<220> FEATURE:
<223> OTHER INFORMATION: Artificially Synthesized Sequence

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser
            20                  25

<210> SEQ ID NO 42
<211> LENGTH: 18
<212> TYPE: PRT
<213> ORGANISM: Artificial Sequence
<220> FEATURE:
<223> OTHER INFORMATION: Artificially Synthesized Sequence

<400> SEQUENCE: 42

Leu Ala Trp Tyr Gln Gln Lys Pro Gly Lys Ala Pro Lys Ser Leu Ile
1               5                   10                  15

Tyr Ser

<210> SEQ ID NO 43
<211> LENGTH: 35
<212> TYPE: PRT
<213> ORGANISM: Artificial Sequence
<220> FEATURE:
<223> OTHER INFORMATION: Artificially Synthesized Sequence

<400> SEQUENCE: 43

Arg Gln Ser Gly Val Pro Ser Arg Phe Ser Gly Ser Gly Ser Gly Thr
1               5                   10                  15

Asp Phe Thr Leu Thr Ile Ser Ser Leu Gln Pro Glu Asp Phe Ala Thr
            20                  25                  30

Tyr Tyr Cys
        35

<210> SEQ ID NO 44
<211> LENGTH: 10
<212> TYPE: PRT
<213> ORGANISM: Artificial Sequence
<220> FEATURE:
<223> OTHER INFORMATION: Artificially Synthesized Sequence

<400> SEQUENCE: 44
```

-continued

```
Phe Gly Gln Gly Thr Lys Leu Glu Ile Lys
1               5                   10

<210> SEQ ID NO 45
<211> LENGTH: 18
<212> TYPE: PRT
<213> ORGANISM: Artificial Sequence
<220> FEATURE:
<223> OTHER INFORMATION: Artificially Synthesized Sequence

<400> SEQUENCE: 45

Leu Ala Trp Tyr Gln Gln Lys Pro Gly Gln Ala Pro Arg Ser Leu Ile
1               5                   10                  15

Tyr Ala

<210> SEQ ID NO 46
<211> LENGTH: 35
<212> TYPE: PRT
<213> ORGANISM: Artificial Sequence
<220> FEATURE:
<223> OTHER INFORMATION: Artificially Synthesized Sequence

<400> SEQUENCE: 46

Leu Gln Ser Gly Ile Pro Ala Arg Phe Ser Gly Ser Gly Ser Gly Thr
1               5                   10                  15

Asp Phe Thr Leu Thr Ile Ser Ser Leu Glu Pro Glu Asp Phe Ala Val
            20                  25                  30

Tyr Tyr Cys
        35

<210> SEQ ID NO 47
<211> LENGTH: 18
<212> TYPE: PRT
<213> ORGANISM: Artificial Sequence
<220> FEATURE:
<223> OTHER INFORMATION: Artificially Synthesized Sequence

<400> SEQUENCE: 47

Leu Ala Trp Tyr Gln Gln Lys Pro Gly Gln Ala Pro Arg Ser Leu Ile
1               5                   10                  15

Tyr Ser

<210> SEQ ID NO 48
<211> LENGTH: 35
<212> TYPE: PRT
<213> ORGANISM: Artificial Sequence
<220> FEATURE:
<223> OTHER INFORMATION: Artificially Synthesized Sequence

<400> SEQUENCE: 48

Arg Gln Ser Gly Ile Pro Ala Arg Phe Ser Gly Ser Gly Ser Gly Thr
1               5                   10                  15

Asp Phe Thr Leu Thr Ile Ser Ser Leu Glu Pro Glu Asp Phe Ala Val
            20                  25                  30

Tyr Tyr Cys
        35

<210> SEQ ID NO 49
<211> LENGTH: 449
<212> TYPE: PRT
<213> ORGANISM: Artificial Sequence
<220> FEATURE:
<223> OTHER INFORMATION: Artificially Synthesized Sequence
```

-continued

```
<400> SEQUENCE: 49

Glu Val Gln Leu Val Gln Ser Gly Ala Glu Val Lys Lys Pro Gly Glu
1               5                   10                  15

Ser Leu Lys Ile Ser Cys Gln Ser Ser Gly Tyr Ser Phe Thr Thr Tyr
                20                  25                  30

Trp Ile Gly Trp Val Arg Gln Met Pro Gly Gln Gly Leu Glu Trp Ile
            35                  40                  45

Gly Ile Met Ser Pro Val Asp Ser Asp Ile Arg Tyr Asn Pro Met Phe
    50                  55                  60

Arg Gly Gln Val Thr Met Ser Val Asp Lys Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 50
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ser Trp
            20                  25                  30

Leu Ala Trp Tyr Gln Gln Lys Pro Gly Lys Ala Pro Lys Ser Leu Ile
            35                  40                  45

Tyr Ser Ala Ser Ser Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ile Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 51
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 51

Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Gly Ser Trp
            20                  25                  30

Leu Ala Trp Tyr Gln Gln Lys Pro Gly Gln Ala Pro Arg Ser Leu Ile
            35                  40                  45
```

```
Tyr Ala Ala Ser Asn Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 52
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 52

```
Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Ser Ser Trp
            20                  25                  30

Leu Ala Trp Tyr Gln Gln Lys Pro Gly Gln Ala Pro Arg Ser Leu Ile
        35                  40                  45

Tyr Ser Ala Ser Asn Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 53
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 53

Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Ser Ser Trp
                20                  25                  30

Leu Ala Trp Tyr Gln Gln Lys Pro Gly Gln Ala Pro Arg Ser Leu Ile
        35                  40                  45

Tyr Ala Ala Ser Asn Arg Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Ile Tyr Pro Tyr
                85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 214
<212> TYPE: PRT
<213> ORGANISM: Artificial Sequence
<220> FEATURE:
<223> OTHER INFORMATION: Artificially Synthesized Sequence

<400> SEQUENCE: 54

Glu Ile Val Leu Thr Gln Ser Pro Ala Thr Leu Ser Ala Ser Pro Gly
1               5                   10                  15

Glu Arg Ala Thr Ile Ser Cys Arg Ala Ser Gln Ser Val Ser Ser Trp
                20                  25                  30

Leu Ala Trp Tyr Gln Gln Lys Pro Gly Gln Ala Pro Arg Ser Leu Ile
        35                  40                  45

Tyr Ala Ala Ser Asn Leu Gln Ser Gly Ile Pro Ala Arg Phe Ser Gly
```

-continued

```
        50                    55                    60

Ser Gly Ser Gly Thr Asp Phe Thr Leu Thr Ile Ser Ser Leu Glu Pro
65                    70                    75                    80

Glu Asp Phe Ala Val Tyr Tyr Cys Gln Gln Tyr Asn Ile Tyr Pro Phe
                  85                    90                    95

Thr Phe Gly Gln Gly Thr Arg Leu Glu Ile Lys Arg Thr Val Ala Ala
                 100                   105                   110

Pro Ser Val Phe Ile Phe Pro Pro Ser Asp Glu Gln Leu Lys Ser Gly
             115                   120                   125

Thr Ala Ser Val Val Cys Leu Leu Asn Asn Phe Tyr Pro Arg Glu Ala
         130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                 165                   170                   175

Ser Thr Leu Thr Leu Ser Lys Ala Asp Tyr Glu Lys His Lys Val Tyr
                 180                   185                   190

Ala Cys Glu Val Thr His Gln Gly Leu Ser Ser Pro Val Thr Lys Ser
         195                   200                   205

Phe Asn Arg Gly Glu Cys
    210
```

ANTI-HUMAN P40 PROTEIN DOMAIN ANTIBODY AND USE THEREOF

CROSS-REFERENCE TO RELATED APPLICATIONS

This application is a National Phase application under 35 U.S.C. 371 of PCT/CN2020/105039, filed Jul. 28, 2020, and claims the benefit of and priority to Chinese Application No. 201910706137.1, filed Jul. 30, 2019, Chinese Application No. 201911040745.X, filed Oct. 29, 2019, and Chinese Application No. 201911171754.2, filed Nov. 25, 2019, the disclosures of which are hereby incorporated herein by reference in their entirety.

REFERENCE TO SEQUENCE LISTING

The Sequence Listing submitted on Jan. 31, 2022, as a text file named "ABIO_101_ST25.txt," created on Jul. 28, 2020, and having a size of 41,010 bytes is hereby incorporated by reference.

TECHNICAL FIELD

The present invention belongs to the field of medicines, and particularly relates to a monoclonal antibody for blocking the function of an interleukin IL-12/IL-23 p40 protein domain and use thereof.

BACKGROUND

Interleukin 12 (IL-12), also known as cytotoxic lymphocyte maturation factor (CLMF) or natural killer cell stimulation factor (NKSF), is a member of the interleukin family. IL-12 has a unique heterodimeric structure, and it is a glycosylated peptide chain (having a relative molecular mass of 75,000 Daltons) formed by covalently linking two protein domains, p40 and p35, via a disulfide bond. It has a heavy chain (p40) consisting of 306 amino acids and comprising 10 cysteine residues and 4 potential glycosylation sites, and a light chain (p35) consisting of 197 amino acids and comprising 7 cysteine residues and 3 potential glycosylation sites.

Interleukin 23 (IL-23), a new member of the Interleukin-12 (IL-12) cytokine family discovered in 2000 by Oppmann et al., is a biologically active complex cytokine formed by covalently linking a p19 protein domain and a p40 protein domain of IL-12 via a disulfide bond. IL-23 can be secreted by activated antigen presenting cells and by dendritic cells. IL-23 binds to its receptors IL-23R and IL-12Rβ1, but not to IL-12Rβ2 (Oppmann B et al., *Immunity*, 2000, 13(5): 715-725).

IL-23 and IL-12 share the same signaling pathways, such as Janus kinases Tyk2, Jak2, and STATs, but each affects different T cells. IL-23 induces acute proliferation of memory T cell CD4+, whereas IL-12 stimulates proliferation of virgin CD4+ T cells. Similar to IL-12, human IL-23 stimulates IFN-γ production and proliferation in PHA-activated T cells and CD45RO+ T cells. Antagonizing the common subunit p40 of IL-12 and IL-23 can effectively antagonize IL-12 and IL-23 pathways simultaneously.

Interleukin 12 is mainly produced by dendritic cells, macrophages, B lymphocytes and some other antigen presenting cells (APCs), and it can enhance the cytotoxicity of natural killer cells (NK cells) and cytoxic T cells (Tc cells), stimulate resting or activated T cells and NK cells to produce interferon γ (IFN-γ), and promote the differentiation of Th0 to Th1. It also promotes Th1 cells to secrete IFN-γ and IL2 to mediate cellular immune responses, induces T cells and NK cells to produce IFN-γ, and provides extramedullary hematopoiesis function. IL-12 plays an extremely important role in both early nonspecific immunity and subsequent antigen-specific adaptive immune processes in the body, and it is a multifunctional immune regulator (Manetti R et al., *Journal of Experimental Medicine,* 1993, 177(4): 1199-1204). The role of IL-12 in autoimmune induction is: (1) promoting the differentiation and proliferation of antigen-specific Th1 cells to generate a plurality of cytokines, and enhancing Th1 type immune response, and (2) stimulating mononuclear macrophages to generate various active media, enhancing the cytotoxicity of immunocompetent cells and causing self tissue damage; IL-12 is also involved in antibody-mediated autoimmunity.

IL-23 plays an important role in a variety of immunological diseases and is thought to be involved in the onset of psoriasis. The accumulation of abnormal IL-2 and TNF-a at the skin lesion of the psoriasis accelerates the occurrence and development of psoriasis, and it is considered that lymphocytes at the skin lesion secrete a plurality of cytokines and thus a huge cell network mainly comprising Th1 cytokines is formed, which is an important pathological basis of the disease. Th1 cytokines secreted by DCs appear to be initiating factors in the onset of psoriasis, and mature DCs can increase IFN-α and IL-12 expression. The specific mechanism of action of mental, genetic and infectious factors in onset of the disease is unknown. Saint-Mezard et al. found that mental stress promoted the aggregation of skin DCs, enhancing the skin's delayed allergic response to haptens. It has been experimentally confirmed that IL-23 also acts on DC-induced inflammatory responses, but it is not clear whether it is a direct inflammatory factor. IL-12 induces the onset of psoriasis by mediating T-cells to the skin surface via skin lymphocyte antigens, and Rosmarin et al. analyzed the structure, receptor and function of IL-12 and suggested that psoriasis can be treated by altering IL-12 levels (Rosmarin D et al., *Journal of Drugs in Dermatology,* 2005, 4(3): 318-325).

Systemic lupus erythematosus (SLE) is a complex systemic autoimmune disease. Currently, there's no effective treatment means for clinical treatment in China, and the conventional treatment mainly comprises hormones and immunosuppressants. STELARA® (ustekinumab), a product of the famous pharmaceutical company Johnson & Johnson, is a completely human IL-12 and IL-23 antagonist, which has been approved by the U.S. FDA for SLE treatment, demonstrating the effectiveness of anti-IL-12 p40 antibodies in treating SLE (Janssen R&D's STELARA (ustekinumab) Shows Positive Results in Treatment of Systemic Lupus Erythematosus in Phase II Trial).

Therefore, IL-12 and IL-23 are extremely important in autoimmune induction and immune response maintenance, so any part in blocking production or signaling of IL-12 and IL-23 can prevent or restrain occurrence and development of an autoimmune disease.

Structurally, IL-12 and IL-23 both have the p40 protein domain, and a monoclonal antibody specifically binding to the p40 protein domain can be used as a blocker for IL-12 and IL-23 pathways, thereby being a new drug for treating autoimmune diseases (such as plaque psoriasis and systemic lupus erythematosus).

Ulcerative colitis is an IBD disease and mainly characterized by immune dysfunction. It features complex clinical pathological changes, long disease course and repeated attacks, and is an immune disease with complex disease condition. More than half of patients have received conventional or biological therapy and haven't been relieved. Ulcerative colitis is the result of the combined action of exogenous and host factors in a certain genetic context. Lesions are usually located in the sigmoid colon and rectum and may extend to the descending colon, or even the entire colon. The disease course is long and repeated attacks are common. The disease occurs at any age, but is most common among those aged 20-30. In view of the characteristics of ulcerative colitis, there is a need to find more excellent antibody drugs for treating patients with ulcerative colitis.

SUMMARY

The inventors designed, based on the crystal structures of IL-12/IL-23 p40 and by using artificial intelligence, a monoclonal antibody technology to develop an antibody sequence, carried out preliminary screening on the antibody by methods such as ELISA, and finally selected the antibody with better potency as a candidate antibody for subsequent pharmacodynamic research.

Further, the inventors prepared humanized antibodies against human IL-12/IL-23 p40 protein domain (e.g., humanized antibodies called H5L9, H5L10, H5L11, H5L12, H5L14 and H8L15).

The inventors surprisingly found that the antibodies can specifically bind to the human IL-12/IL-23 p40 protein domain and exhibit good binding activity.

Further, the inventors surprisingly found that the antibodies disclosed herein can effectively block the binding of the human IL-12/IL-23 p40 protein domain to cell surface receptors IL-12Rβ1 and IL-23R, and inhibit IL-23-induced IL-17A secretion by human peripheral blood mononuclear lymphocytes.

The inventors also surprisingly found that the antibodies disclosed herein can effectively bind to the human IL-12/IL-23 p40 protein domain, block the binding of the human IL-12/IL-23 p40 protein domain to ligands IL-12Rβ1 and IL-23R, and inhibit the activation of the signaling pathways downstream of IL-12/IL-23. They have the potential of being used for preparing medicaments for preventing and treating autoimmune diseases (e.g., plaque psoriasis or systemic lupus erythematosus) and ulcerative colitis (e.g., refractory or recurrent).

The amino acid sequences of the CDR regions of the antibodies above are analyzed by technical means well known to those skilled in the art, for example, by a VBASE2 database.

It will be understood by those of ordinary skill in the art that the CDR regions of an antibody are responsible for the binding specificity of the antibody for an antigen. Given the known sequences of the heavy and light chain variable regions of an antibody, there are several methods for determining the CDR regions of the antibody, including the Kabat, IMGT, Chothia and AbM numbering systems.

Specifically, the AbM numbering system: the AbM method for defining CDRs was derived from Martin's related research (Martin A C R, Cheetham J C, Rees Ark. (1989) Modelling antibody hypervariableloops: A combined algorithm. *Proc Natl Acad Sci USA* 86: 9268-9272), and this method integrates partial definitions of Kabat and Chothia method.

Kabat numbering system: see, e.g., Kabat et al., Sequences of Proteins of Immunological Interest, 5th Ed. Public Health Service, National Institutes of Health, Bethesda, Md., 1991.

Chothia numbering system: see, e.g., Chothia & Lesk (1987) *J. Mol. Biol.* 196: 901-917; Chothia et al. (1989), *Nature* 342: 878-883.

IMGT numbering system: see, e.g., Lefranc et al., *Dev. Comparat. Immunol.* 27: 55-77, 2003.

However, the application of all the definitions of CDRs for an antibody or its variant shall fall within the scope of the terms defined and used herein. If an amino acid sequence of the variable region of the antibody is known, those skilled in the art can generally determine which residues comprise a particular CDR, without relying on any experimental data beyond the sequence itself. Suitable amino acid residues of the CDRs as defined by the Kabat and Chothia CDR numbering systems are listed below for comparison. The exact number of residues comprising a particular CDR will vary with the sequence and size of that CDR.

Preferably, the antibodies H5L9, H5L10, H5L11, H5L12 and H5L14 disclosed herein have the same HCDR1-3:

The amino acid sequences of the 3 HCDR regions of the heavy chain variable region are as follows:

```
                                          (SEQ ID NO: 3)
             HCDR1: GYSFTTYW (SEQ ID NO: 4)
             HCDR2: IMSPVDSDI (SEQ ID NO: 5)
             HCDR3: ARRRPGQGYFDF
```

The antibody H5L9 disclosed herein has LCDR1-3:

The amino acid sequences of the 3 CDR regions of the light chain variable region are as follows:

```
                                          (SEQ ID NO: 8)
             LCDR1: QNVGSW (SEQ ID NO: 9)
             LCDR2: ASS (SEQ ID NO: 10)
             LCDR3: QQYDIYPFT
```

The antibody H5L10 disclosed herein has LCDR1-3:

The amino acid sequences of the 3 CDR regions of the light chain variable region are as follows:

```
                                          (SEQ ID NO: 19)
             LCDR1: QSVGSW (SEQ ID NO: 21)
             LCDR2: ASN (SEQ ID NO: 22)
             LCDR3: QQYNIYPYT
```

The antibodies H5L11 and H5L12 disclosed herein have the same LCDR1-3:

The amino acid sequences of the 3 CDR regions of the light chain variable region are as follows:

```
                                          (SEQ ID NO: 20)
             LCDR1: QSVSSW (SEQ ID NO: 21)
             LCDR2: ASN (SEQ ID NO: 22)
             LCDR3: QQYNIYPYT
```

The antibody H5L14 disclosed herein has LCDR1-3:

The amino acid sequences of the 3 CDR regions of the light chain variable region are as follows:

```
                              (SEQ ID NO: 20)
            LCDR1: QSVSSW (SEQ ID NO: 21)
            LCDR2: ASN (SEQ ID NO: 23)
            LCDR3: QQYNIYPFT
```

The antibody H8L15 disclosed herein has HCDR1-3 and LCDR1-3:

The amino acid sequences of the 3 HCDR regions of the heavy chain variable region are as follows:

```
                              (SEQ ID NO: 26)
            HCDR1: GYTFTSYW (SEQ ID NO: 4)
            HCDR2: MSPVDSDI (SEQ ID NO: 5)
            HCDR3: ARRRPGQGYFDF
```

The amino acid sequences of the 3 CDR regions of the light chain variable region are as follows:

```
                              (SEQ ID NO: 27)
            LCDR1: QSVGTW (SEQ ID NO: 28)
            LCDR2: AAS (SEQ ID NO: 22)
            LCDR3: QQYNIYPYT.
```

The present invention is detailed below.

One aspect of the present invention relates to an antibody or an antigen-binding fragment thereof preferably specifically binding to human IL-12/IL-23 p40, wherein:

(1) the antibody comprises:

an HCDR1, an HCDR2 and an HCDR3 contained in a heavy chain variable region set forth in SEQ ID NO: 1, wherein preferably, the HCDR1 comprises or consists of a sequence set forth in SEQ ID NO: 3, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the HCDR2 comprises or consists of a sequence set forth in SEQ ID NO: 4, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the HCDR3 comprises or consists of a sequence set forth in SEQ ID NO: 5, a sequence having at least 80%, 81%, 82%, 83%, 84%, 85%, 86%, 87%, 88%, 89%, 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence; and the antibody further comprises:

an LCDR1, an LCDR2 and an LCDR3 contained in a light chain variable region set forth in SEQ ID NO: 6, wherein preferably, the LCDR1 comprises or consists of an amino acid sequence set forth in SEQ ID NO: 8, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the LCDR2 comprises or consists of an amino acid sequence set forth in SEQ ID NO: 9, a sequence having at least 80%, 81%, 82%, 83%, 84%, 85% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the LCDR3 comprises or consists of a sequence set forth in SEQ ID NO: 10, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence;

(2) the antibody comprises:

an HCDR1, an HCDR2 and an HCDR3 contained in a heavy chain variable region set forth in SEQ ID NO: 1, wherein preferably, the HCDR1 comprises or consists of a sequence set forth in SEQ ID NO: 3, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the HCDR2 comprises or consists of a sequence set forth in SEQ ID NO: 4, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the HCDR3 comprises or consists of a sequence set forth in SEQ ID NO: 5, a sequence having at least 80%, 81%, 82%, 83%, 84%, 85%, 86%, 87%, 88%, 89%, 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence; and the antibody further comprises:

an LCDR1, an LCDR2 and an LCDR3 contained in a light chain variable region set forth in SEQ ID NO: 11, wherein preferably, the LCDR1 comprises or consists of an amino acid sequence set forth in SEQ ID NO: 19, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the LCDR2 comprises or consists of an amino acid sequence set forth in SEQ ID NO: 21, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the LCDR3 comprises or consists of a sequence set forth in SEQ ID NO: 22, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence;

(3) the antibody comprises:

an HCDR1, an HCDR2 and an HCDR3 contained in a heavy chain variable region set forth in SEQ ID NO: 1, wherein preferably, the HCDR1 comprises or consists of a sequence set forth in SEQ ID NO: 3, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the HCDR2 comprises or consists of a sequence set forth in SEQ ID NO: 4, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the HCDR3 comprises or consists of a sequence set forth in SEQ ID NO: 5, a sequence having at least 80%, 81%, 82%, 83%, 84%, 85%, 86%, 87%, 88%, 89%, 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence; and the antibody further comprises:

an LCDR1, an LCDR2 and an LCDR3 contained in a light chain variable region set forth in SEQ ID NOs: 13 and 15, wherein preferably, the LCDR1 comprises or consists of an amino acid sequence set forth in SEQ ID NO: 20, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the LCDR2 comprises or consists of an amino acid sequence set forth in SEQ ID NO: 21, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the LCDR3 comprises or consists of a sequence set forth in SEQ ID NO: 22, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence;

(4) the antibody comprises:

an HCDR1, an HCDR2 and an HCDR3 contained in a heavy chain variable region set forth in SEQ ID NO: 1, wherein preferably, the HCDR1 comprises or consists of a sequence set forth in SEQ ID NO: 3, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the HCDR2 comprises or consists of a sequence set forth in SEQ ID NO: 4, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the HCDR3 comprises or consists of a sequence set forth in SEQ ID NO: 5, a sequence having at least 80%, 81%, 82%, 83%, 84%, 85%, 86%, 87%, 88%, 89%, 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence; and the antibody further comprises:

an LCDR1, an LCDR2 and an LCDR3 contained in a light chain variable region set forth in SEQ ID NO: 17, wherein preferably, the LCDR1 comprises or consists of an amino acid sequence set forth in SEQ ID NO: 20, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the LCDR2 comprises or consists of an amino acid sequence set forth in SEQ ID NO: 21, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the LCDR3 comprises or consists of a sequence set forth in SEQ ID NO: 23, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence;

(5) the antibody comprises:

an HCDR1, an HCDR2 and an HCDR3 contained in a heavy chain variable region set forth in SEQ ID NO: 24, wherein preferably, the HCDR1 comprises or consists of a sequence set forth in SEQ ID NO: 26, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the HCDR2 comprises or consists of a sequence set forth in SEQ ID NO: 4, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the HCDR3 comprises or consists of a sequence set forth in SEQ ID NO: 5, a sequence having at least 80%, 81%, 82%, 83%, 84%, 85%, 86%, 87%, 88%, 89%, 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence; and the antibody further comprises:

an LCDR1, an LCDR2 and an LCDR3 contained in a light chain variable region set forth in SEQ ID NO: 25, wherein preferably, the LCDR1 comprises or consists of an amino acid sequence set forth in SEQ ID NO: 27, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, the LCDR2 comprises or consists of an amino acid sequence set forth in SEQ ID NO: 28, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence, and the LCDR3 comprises or consists of a sequence set forth in SEQ ID NO: 22, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2 or 3) conservative amino acid mutations (preferably substitutions, insertions or deletions) compared to the sequence.

In some embodiments of the present invention, the antibody comprises:

(1) a heavy chain variable region comprising or consisting of:

an amino acid sequence set forth in SEQ ID NO: 1, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 1, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 1; and a light chain variable region comprising or consisting of:

an amino acid sequence set forth in SEQ ID NO: 6, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 6, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 6;

(2) a heavy chain variable region, comprising or consisting of:

an amino acid sequence set forth in SEQ ID NO: 1, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 1, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 1; and a light chain variable region comprising or consisting of:

an amino acid sequence set forth in SEQ ID NO: 11, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 11, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 11;

(3) a heavy chain variable region comprising or consisting of:

an amino acid sequence set forth in SEQ ID NO: 1, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 1, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 1; and a light chain variable region comprising or consisting of:

an amino acid sequence set forth in SEQ ID NO: 13, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 13, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 13;

(4) a heavy chain variable region comprising or consisting of:

an amino acid sequence set forth in SEQ ID NO: 1, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 1, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 1; and a light chain variable region comprising or consisting of:

an amino acid sequence set forth in SEQ ID NO: 15, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 15, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 15;

(5) a heavy chain variable region comprising or consisting of:

an amino acid sequence set forth in SEQ ID NO: 1, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 1, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 1; and a light chain variable region comprising or consisting of:

an amino acid sequence set forth in SEQ ID NO: 17, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 17, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 17;

(6) a heavy chain variable region comprising or consisting of:

an amino acid sequence set forth in SEQ ID NO: 24, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 24, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 24; and a light chain variable region comprising or consisting of:

an amino acid sequence set forth in SEQ ID NO: 25, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 25, or an amino acid sequence having one or more (preferably 1, 2, 3, 4, 5, 6, 7, 8, 9 or 10) conservative amino acid mutations (preferably substitutions, insertions or deletions) compared to the sequence set forth in SEQ ID NO: 25.

In an embodiment of the present invention, the antibody further comprises framework regions (FRs) in the heavy chain variable region, preferably the FRs including FR-H1, FR-H2, FR-H3 and FR-H4, wherein the FR-H1 comprises or consists of an amino acid sequence set forth in SEQ ID NO: 29, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 29, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 29; the FR-H2 comprises or consists of an amino acid sequence set forth in SEQ ID NO: 30, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 30, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 30; the FR-H3 comprises or consists of an amino acid sequence set forth in SEQ ID NO: 31, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 31, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 31; the FR-H4 comprises or consists of an amino acid sequence set forth in SEQ ID NO: 32, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 32, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 32.

In an embodiment of the present invention, the antibody further comprises framework regions (FRs) in the light chain variable region, preferably the FRs including FR-L1, FR-L2, FR-L3 and FR-L4, wherein the FR-L1 comprises or consists of an amino acid sequence set forth in SEQ ID NO: 33, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 33, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 33; the FR-L2 comprises or consists of an amino acid sequence set forth in SEQ ID NO: 34, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 34, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 34; the FR-L3 comprises or consists of an amino acid sequence set forth in SEQ ID NO: 35, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 35, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 35; the FR-L4 comprises or consists of an amino acid sequence set forth in SEQ ID NO: 36, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 36, or an amino acid sequence having one or more (prefer-ably 1, 2, 3, 4, 5, 6, 7, 8, 9 or 10) conservative amino acid mutations (preferably substitutions, insertions or deletions) compared to the amino acid sequence set forth in SEQ ID NO: 36.

In an embodiment of the present invention, the antibody further comprises framework regions (FRs) in the light chain variable region, preferably the FRs including FR-L1, FR-L2, FR-L3 and FR-L4, wherein the FR-L1 comprises or consists of an amino acid sequence set forth in SEQ ID NO: 41, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 41, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 41; the FR-L2 comprises or consists of an amino acid sequence set forth in SEQ ID NO: 42, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 42, or an amino acid sequence having one or more (prefer-ably 1, 2, 3, 4, 5, 6, 7, 8, 9 or 10) conservative amino acid mutations (preferably substitutions, insertions or deletions) compared to the amino acid sequence set forth in SEQ ID NO: 42; the FR-L3 comprises or consists of an amino acid sequence set forth in SEQ ID NO: 43, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 43, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 43; the FR-L4 comprises or consists of an amino acid sequence set forth in SEQ ID NO: 44, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 44, or an amino acid sequence having one or more (prefer-ably 1, 2, 3, 4, 5, 6, 7, 8, 9 or 10) conservative amino acid mutations (preferably substitutions, insertions or deletions) compared to the amino acid sequence set forth in SEQ ID NO: 44.

In an embodiment of the present invention, the antibody further comprises framework regions (FRs) in the light chain variable region, preferably the FRs including FR-L1, FR-L2, FR-L3 and FR-L4, wherein the FR-L1 comprises or consists of an amino acid sequence set forth in SEQ ID NO: 33, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 33, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 33; the FR-L2 comprises or consists of an amino acid sequence set forth in SEQ ID NO: 45, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 45, or an amino acid sequence having one or more (prefer-ably 1, 2, 3, 4, 5, 6, 7, 8, 9 or 10) conservative amino acid mutations (preferably substitutions, insertions or deletions) compared to the amino acid sequence set forth in SEQ ID NO: 45; the FR-L3 comprises or consists of an amino acid sequence set forth in SEQ ID NO: 46, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 46, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 46; the FR-L4 comprises or consists of an amino acid sequence set forth in SEQ ID NO: 36, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 36, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 36.

In an embodiment of the present invention, the antibody further comprises framework regions (FRs) in the light chain variable region, preferably the FRs including FR-L1, FR-L2, FR-L3 and FR-L4, wherein the FR-L1 comprises or consists of an amino acid sequence set forth in SEQ ID NO: 33, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 33, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 33; the FR-L2 comprises or consists of an amino acid sequence set forth in SEQ ID NO: 47, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 47, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 47; the FR-L3 comprises or consists of an amino acid sequence set forth in SEQ ID NO: 46, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 46, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 46; the FR-L4 comprises or consists of an amino acid sequence set forth in SEQ ID NO: 36, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 36, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 36.

In an embodiment of the present invention, the antibody further comprises framework regions (FRs) in the light chain variable region, preferably the FRs including FR-L1, FR-L2, FR-L3 and FR-L4, wherein the FR-L1 comprises or consists of an amino acid sequence set forth in SEQ ID NO: 33, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 33, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 33; the FR-L2 comprises or consists of an amino acid sequence set forth in SEQ ID NO: 45, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 45, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 45; the FR-L3 comprises or consists of an amino acid sequence set forth in SEQ ID NO: 48, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 48, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 48; the FR-L4 comprises or consists of an amino acid sequence set forth in SEQ ID NO: 36, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence set forth in SEQ ID NO: 36, or an amino acid sequence having one or more (preferably 1, 2, 3, 4, 5, 6, 7, 8, 9 or 10) conservative amino acid mutations (preferably substitutions, insertions or deletions) compared to the amino acid sequence set forth in SEQ ID NO: 36.

In an embodiment of the present invention, the antibody comprises or consists of a heavy chain set forth in SEQ ID NO: 39 and a light chain set forth in SEQ ID NO: 40.

In an embodiment of the present invention, the antibody comprises or consists of a heavy chain set forth in SEQ ID NO: 49 and a light chain set forth in SEQ ID NO: 50.

In an embodiment of the present invention, the antibody comprises or consists of a heavy chain set forth in SEQ ID NO: 49 and a light chain set forth in SEQ ID NO: 51.

In an embodiment of the present invention, the antibody comprises or consists of a heavy chain set forth in SEQ ID NO: 49 and a light chain set forth in SEQ ID NO: 52.

In an embodiment of the present invention, the antibody comprises or consists of a heavy chain set forth in SEQ ID NO: 49 and a light chain set forth in SEQ ID NO: 53.

In an embodiment of the present invention, the antibody comprises or consists of a heavy chain set forth in SEQ ID NO: 49 and a light chain set forth in SEQ ID NO: 54.

One aspect of the present invention relates to an isolated polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 8, 9 and 10.

One aspect of the present invention relates to an isolated polypeptide comprising sequences set forth in SEQ ID NOs: 8, 9 and 10, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

One aspect of the present invention relates to an isolated polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 19, 21 and 22.

One aspect of the present invention relates to an isolated polypeptide comprising sequences set forth in SEQ ID NOs: 19, 21 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

One aspect of the present invention relates to an isolated polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 20, 21 and 22.

One aspect of the present invention relates to an isolated polypeptide comprising sequences set forth in SEQ ID NOs: 20, 21 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

One aspect of the present invention relates to an isolated polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 20, 21 and 23.

One aspect of the present invention relates to an isolated polypeptide comprising sequences set forth in SEQ ID NOs: 20, 21 and 23, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

One aspect of the present invention relates to an isolated polypeptide comprising sequences set forth in SEQ ID NOs: 26, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 27, 28 and 22.

One aspect of the present invention relates to an isolated polypeptide comprising sequences set forth in SEQ ID NOs: 27, 28 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 26, 4 and 5.

One aspect of the present invention relates to an isolated polypeptide comprising a sequence set forth in SEQ ID NO: 1 or 24, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to human IL-12/IL-23 p40 protein domain as part of an anti-human IL-12/IL-23 p40 protein domain antibody, the antibody further comprising a sequence set forth in SEQ ID NO: 6, 11, 13, 15, 17 or 25, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence; or an isolated polypeptide comprising a sequence set forth in SEQ ID NO: 6, 11, 13, 15, 17 or 25, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to human IL-12/IL-23 p40 protein domain as part of an anti-human IL-12/IL-23 p40 protein domain antibody, the antibody further comprising a sequence set forth in SEQ ID NO: 1 or 24, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence.

In an embodiment of the present invention, the antigen-binding fragment is selected from the group consisting of Fab, Fab', F(ab')$_2$, Fd, Fv, dAb, Fab/c, complementarity determining region (CDR) fragment, single chain antibody (e.g., scFv), bivalent antibody and domain antibody.

In an embodiment of the present invention, the antibody is a humanized antibody, a chimeric antibody or a multi-specific antibody (e.g., a bispecific antibody).

In an embodiment of the present invention, the antibody binds to human IL-12/IL-23 p40 protein domain with a $K_D$ of less than about $10^{-5}$ M, e.g., less than about $10^{-6}$ M, $10^{-7}$ M, $10^{-8}$ M, $10^{-9}$ M or $10^{-10}$ M or less. Preferably, the $K_D$ is measured by a Fortebio molecular interaction analyzer.

In an embodiment of the present invention, the antibody binds to human IL-12/IL-23 p40 protein domain with an $EC_{50}$ of less than about 100 nM, e.g., less than about 10 nM, 1 nM, 0.9 nM, 0.8 nM, 0.7 nM, 0.6 nM, 0.5 nM, 0.4 nM, 0.3 nM, 0.2 nM, 0.1 nM or less. Specifically, the $EC_{50}$ is measured by indirect ELISA.

In an embodiment of the present invention, the antibody comprises constant regions, and the constant regions are derived from species other than murine, e.g., from a human antibody, preferably from a human IgG, more preferably from IgG1.

In an embodiment of the present invention, the constant regions of the antibody are humanized, e.g., the heavy chain constant region is an Ig gamma-1 chain C region, preferably an Ig gamma-1 chain C region of GenBank ACCESSION No. P01857; the light chain constant region is an Ig kappa chain C region, preferably an Ig kappa chain C region of GenBank ACCESSION No. P01834.

Another aspect of the present invention relates to an isolated polynucleotide encoding a polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 8, 9 and 10.

One aspect of the present invention relates to an isolated polynucleotide encoding a polypeptide comprising sequences set forth in SEQ ID NOs: 8, 9 and 10, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

Another aspect of the present invention relates to an isolated polynucleotide encoding a polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 19, 21 and 22.

One aspect of the present invention relates to an isolated polynucleotide encoding a polypeptide comprising sequences set forth in SEQ ID NOs: 19, 21 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

Another aspect of the present invention relates to an isolated polynucleotide encoding a polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 20, 21 and 22.

One aspect of the present invention relates to an isolated polynucleotide encoding a polypeptide comprising sequences set forth in SEQ ID NOs: 20, 21 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

Another aspect of the present invention relates to an isolated polynucleotide encoding a polypeptide comprising sequences set forth in SEQ ID NOs: 3, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 20, 21 and 23.

One aspect of the present invention relates to an isolated polynucleotide encoding a polypeptide comprising sequences set forth in SEQ ID NOs: 20, 21 and 23, wherein the polypeptide specifically binds to human IL-12/IL-23 p40 protein domain as part of an anti-human IL-12/IL-23 p40 protein domain antibody, the antibody further comprising sequences set forth in SEQ ID NOs: 3, 4 and 5.

Another aspect of the present invention relates to an isolated polynucleotide encoding a polypeptide comprising sequences set forth in SEQ ID NOs: 26, 4 and 5, wherein the polypeptide specifically binds to human IL-12/IL-23 p40 protein domain as part of an anti-human IL-12/IL-23 p40 protein domain antibody, the antibody further comprising sequences set forth in SEQ ID NOs: 27, 28 and 22.

One aspect of the present invention relates to an isolated polynucleotide encoding a polypeptide comprising sequences set forth in SEQ ID NOs: 27, 28 and 22, wherein the polypeptide specifically binds to human IL-12/IL-23 p40 protein domain as part of an anti-human IL-12/IL-23 p40 protein domain antibody, the antibody further comprising sequences set forth in SEQ ID NOs: 26, 4 and 5.

One aspect of the present invention relates to an isolated polynucleotide encoding a polypeptide comprising a sequence set forth in SEQ ID NO: 1 or 24, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to human IL-12/IL-23 p40 protein domain as part of an anti-human IL-12/IL-23 p40 protein domain antibody, the antibody further comprising a sequence set forth in SEQ ID NO: 6, 11, 13, 15, 17 or 25, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence; or an isolated polynucleotide encoding a polypeptide comprising a sequence set forth in SEQ ID NO: 6, 11, 13, 15, 17 or 25, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence, wherein the polypeptide specifically binds to human IL-12/IL-23 p40 protein domain as part of an anti-human IL-12/IL-23 p40 protein domain antibody, the antibody further comprising a sequence set forth in SEQ ID NO: 1 or 24, a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence, or an amino acid sequence having one or more (preferably 1, 2, 3, 4, 5, 6, 7, 8, 9 or 10) conservative amino acid mutations (preferably substitutions, insertions or deletions) compared to the sequence.

Specifically, the polynucleotide comprises or consists of a nucleotide sequence set forth in SEQ ID NO: 2, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 7, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 12, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 14, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 16, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 18, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 37, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Specifically, the polynucleotide comprises or consists of a nucleotide sequence set forth in SEQ ID NO: 38, or a sequence having at least 80%, 81%, 82%, 83%, 84%, 85%, 86%, 87%, 88%, 89% or 90%, preferably at least 91%, 92%, 93%, 94%, 95%, 96%, 97%, 98% or 99% sequence identity to the sequence.

Yet another aspect of the present invention relates to a vector comprising any one of the polynucleotide molecules disclosed herein as described above.

Yet another aspect of the present invention relates to a host cell comprising any one of the polynucleotide molecules disclosed herein as described above or the vector disclosed herein.

Yet another aspect of the present invention relates to a method for preparing any one of the antibodies or the antigen-binding fragments thereof disclosed herein as described above, comprising culturing the host cell disclosed herein in a suitable condition, and isolating the antibody or the antigen-binding fragment thereof from the cell cultures.

One aspect of the present invention further provides an antibody conjugate comprising the anti-human IL-12/IL-23 p40 protein domain antibody or the antigen-binding fragment thereof and a conjugated moiety coupled thereto, wherein the conjugated moiety is a purification tag (e.g., a His tag), a cytotoxic agent or a detectable label. Preferably, the conjugated moiety is a radioisotope, a luminescent substance, a colored substance, an enzyme or polyethylene glycol.

One aspect of the present invention further provides a fusion protein comprising any one of the anti-human IL-12/IL-23 p40 protein domain antibodies or the antigen-binding fragments thereof as described above.

One aspect of the present invention provides a multispecific antibody, preferably a bispecific antibody, comprising the antibody or the antigen-binding fragment thereof described herein.

One aspect of the present invention further provides a kit comprising any one of the antibodies or the antigen-binding fragments thereof disclosed herein as described above, or the antibody conjugate, the fusion protein or the multispecific antibody disclosed herein.

Preferably, the kit further comprises a second antibody that specifically identifies the antibody or the antigen-binding fragment thereof; optionally, the second antibody further comprises a detectable label, such as a radioisotope, a luminescent substance, a colored substance, an enzyme or polyethylene glycol.

Yet another aspect of the present invention relates to use of any one of the antibodies or the antigen-binding fragments thereof disclosed herein as described above, the antibody conjugate, the fusion protein or the multispecific antibody in preparing a kit for detecting the presence or level of human IL-12/IL-23 p40 in a sample.

Yet another aspect of the present invention relates to a pharmaceutical composition comprising any one of the antibodies or the antigen-binding fragments thereof disclosed herein as described above, the antibody conjugate, the multispecific antibody or the fusion protein, and optionally, a pharmaceutically acceptable carrier and/or an excipient.

Yet another aspect of the present invention relates to use of any one of the antibodies or the antigen-binding fragments thereof as described above or the antibody conjugate, the multispecific antibody, the fusion protein or the pharmaceutical composition in preparing:

a medicament for blocking the binding of human IL-12/IL-23 p40 to human IL-12Rβ1 or human IL-23R, a medicament for blocking the activity of human IL-12/IL-23 p40 or down-regulating the level thereof, or a medicament for blocking cellular response mediated by the binding of human IL-12Rβ1 or human IL-23R to p40;

preferably, a ligand of the human IL-12/IL-23 p40 is human IL-12Rβ1 or human IL-23R.

One aspect of the present invention relates to use of any one of the antibodies or the antigen-binding fragments thereof as described above, the antibody conjugate, the multispecific antibody, the fusion protein or the pharmaceutical composition in preparing a medicament for treating a disease selected from the group consisting of autoimmune diseases (e.g., plaque psoriasis or systemic lupus erythematosus) and ulcerative colitis (e.g., refractory or recurrent).

Yet another aspect of the present invention relates to an in vivo or in vitro method comprising administering a cell comprising the antibody or the antigen-binding fragment thereof, the antibody conjugate, the multispecific antibody, the fusion protein or the pharmaceutical composition described herein, or administering to a subject in need an effective amount of any one of the antibodies or the antigen-binding fragments thereof disclosed herein as described above, the antibody conjugate, the multispecific antibody, the fusion protein or the pharmaceutical composition. The method is selected from the group consisting of:

a method for blocking the binding of human IL-12/IL-23 p40 to ligand IL-12Rβ1 or IL-23R, a method for down-regulating the activity or the level of human IL-12/IL-23 p40, and a method for blocking cellular response mediated by the binding of human IL-12Rβ1 or human IL-23R to p40;

preferably, a ligand of the IL-12/IL-23 p40 is IL-12Rβ1 or IL-23R.

In an embodiment of the present invention, the in vitro method is for non-therapeutic and/or non-diagnostic purposes.

Yet another aspect of the present invention relates to use of any one of the antibodies or the antigen-binding fragments thereof disclosed herein as described above, the antibody conjugate, the multispecific antibody, the fusion protein or the pharmaceutical composition in preparing a medicament for the prevention, treatment, adjuvant treatment and/or diagnosis of autoimmune diseases (e.g., plaque psoriasis or systemic lupus erythematosus) or ulcerative colitis (e.g., refractory or recurrent), or use thereof for the prevention, treatment, adjuvant treatment and/or diagnosis of autoimmune diseases (e.g., plaque psoriasis or systemic lupus erythematosus) or ulcerative colitis (e.g., refractory or recurrent).

In an embodiment of the present invention, the medicament is in a form suitable for administration by subcutaneous injection, intradermal injection, intravenous injection, intramuscular injection or intralesional injection.

Yet another aspect of the present invention relates to a method for the prevention, treatment, adjuvant treatment and/or diagnosis of autoimmune diseases (e.g., plaque psoriasis or systemic lupus erythematosus) or ulcerative colitis (e.g., refractory or recurrent), which comprises administering to a subject in need any one of the antibodies or the antigen-binding fragments thereof disclosed herein as described above, the antibody conjugate, the multispecific antibody, the fusion protein or the pharmaceutical composition.

The present invention also provides a method for treating a patient suffering from ulcerative colitis, which comprises: (i) measuring the level of human IL-12/IL-23 p40 in a sample of the patient, wherein the patient is positive for human IL-12/IL-23 p40, and (ii) administering to the patient a therapeutically effective amount of the anti-human IL-12/IL-23 p40 antibody or the antigen-binding portion thereof.

The ulcerative colitis described herein can be refractory and recurrent. For example, for some patients, the ulcerative colitis is recurrent; for some patients, the ulcerative colitis is refractory.

In some embodiments of the present invention, the patient has received conventional treatment or is inadequately responsive, unresponsive or intolerant to biological agents. In some specific embodiments, the patient's having received conventional treatment or being inadequately responsive, unresponsive or intolerant to biological agents results in failure to complete response or partial response.

As used herein, the H8L15H1L1 is an anti-human IL-12/IL-23 p40 monoclonal antibody, and reference can be made to patent CN201910706137.1 for its sequence and structure. In the H8L15H1L1 monoclonal antibody, the HCDR1 comprises sequence GYTFTSYW (SEQ ID NO: 3), the HCDR2 comprises sequence MSPVDSDI (SEQ ID NO: 4), the HCDR3 comprises sequence ARRRPGQGYFDF (SEQ ID NO: 5), the LCDR1 comprises sequence QSVGTW (SEQ ID NO: 6), the LCDR2 comprises sequence AAS (SEQ ID NO: 7), and the LCDR3 comprises sequence QQYNIYPYT (SEQ ID NO: 8).

In the present invention, unless otherwise defined, the scientific and technical terms used herein have the meanings generally understood by those skilled in the art. In addition, the laboratory operations of cell culture, molecular genetics, nucleic acid chemistry and immunology used in the present invention are the routine operations widely used in the corresponding fields. Meanwhile, in order to better understand the present invention, the definitions and explanations of the relevant terms are provided below.

As used herein, the term "antigen-binding region" means a protein or a portion of a protein that specifically binds to a given antigen. For example, a portion of an antibody comprising amino acid residues that interact with an antigen and confer the antibody the specificity and affinity for the antigen is referred to as an "antigen-binding region". The antigen-binding region generally comprises one or more complementary determining regions (CDRs). Some antigen-binding regions further comprise one or more "framework" regions (FRs). CDRs are amino acid sequences that contribute to antigen binding specificity and affinity.

As used herein, the term "antibody" refers to an intact immunoglobulin of any isotype or an antigen-binding fragment thereof that can compete with an intact antibody for specifically binding to a target antigen, and includes, for example, chimeric, humanized, fully human, and bispecific antibodies or antigen-binding fragments thereof. Such "antibodies" are antigen-binding proteins. An intact antibody generally comprises at least two full-length heavy chains and two full-length light chains, but, in some cases, may comprise fewer chains, such as an antibody naturally existing in camelids that may comprise only a heavy chain. An antibody or an antigen-binding fragment thereof may be derived from a single source only, or may be "chimeric", i.e., different portions of an antibody may be derived from two different sources as further described below. An antibody or an antigen-binding fragment thereof may be produced in hybridomas by recombinant DNA techniques, or by enzymatic or chemical cleavage of intact antibodies. Unless otherwise indicated, the term "antibody", in addition to antibodies comprising two full-length heavy chains and two full-length light chains, also includes derivatives, variants and fragments thereof.

As used herein, the term "antigen-binding fragment" (or abbreviated as "fragment") of an "antibody" or an "immunoglobulin chain" (heavy or light chain) includes part of an antibody (whether obtained or synthesized) that lacks at least some of the amino acid residues present in the full length of the antibody but is capable of specifically binding to the antigen. Such fragments are biologically active as they specifically bind to a target antigen and can compete with other antibodies or antigen-binding fragments thereof for specifically binding to a given epitope. In one aspect, such fragments will retain at least one CDR present in the full-length light or heavy chain of the antibody, and in some embodiments, will comprise a single heavy and/or light chain or a portion thereof. Such biologically active fragments can be produced by recombinant DNA techniques, or, for example, by enzymatic or chemical cleavage of intact antibodies Immunologically functional immunoglobulin fragments include, but are not limited to, Fab, Fab', F(ab')$_2$, Fv, Fd, dAb, Fab/c, complementarity determining region (CDR) fragment, single chain antibody (e.g., scFv), bivalent antibody and domain antibody, and can be derived from any mammal, including but not limited to, human, mouse, rat, camelids or rabbit. It is further contemplated that a functional portion of an antibody disclosed herein, such as one or more CDRs, can be covalently bound to a second protein or a small molecule to generate a therapeutic agent directed to a particular target in the body, thereby having bifunctional therapeutic properties or having an extended serum half-life, such as a fusion protein.

As used herein, the terms "antibody full-length chain", "full-length antibody", "intact antibody" and "whole antibody" are used interchangeably herein to refer to an antibody having a substantially similar structure to a natural antibody structure or having a heavy chain in Fc region as defined herein.

The term "light chain" includes full-length light chains and fragments thereof with sufficient variable region sequences to confer the binding specificity. The full-length light chain comprises a variable region domain $V_L$ and a constant region domain $C_L$. The variable region domain of the light chain is at the amino terminus of the polypeptide. The Light chain includes kappa (κ) and lambda (λ) chains.

The term "heavy chain" includes full-length heavy chains and fragments thereof with sufficient variable region sequences to confer the binding specificity. The full-length heavy chain includes a variable region domain $V_H$ and 3 constant region domains $C_{H1}$, $C_{H2}$ and $C_{H3}$. The $V_H$ domain is at the amino terminus of the polypeptide, and the $C_H$ domains are at the carboxyl terminus, the $C_{H3}$ being closest to the carboxyl terminus of the polypeptide. The heavy chain may be of any isotype, including IgG (including IgG1, IgG2, IgG3 and IgG4 subtypes), IgA (including IgA1 and IgA2 subtypes), IgM and IgE.

As used herein, the term "Fab fragment" consists of one light chain, $C_{H1}$ and the variable region of one heavy chain. The heavy chain of a Fab molecule cannot form disulfide bonds with another heavy chain molecule.

As used herein, the term "Fc" region comprises two heavy chain fragments comprising the $C_{H1}$ and $C_{H2}$ domains of an antibody. The two heavy chain fragments are held together by two or more disulfide bonds and by the hydrophobic interaction of the $C_{H3}$ domains.

As used herein, the term "Fab' fragment" comprises one light chain and part of one heavy chain (containing the $V_H$ domain, the $C_{H1}$ domain, and part of the region between the $C_{H1}$ and $C_{H2}$ domains), such that interchain disulfide bonds can be formed between the two heavy chains of two Fab' fragments to obtain a $F(ab')_2$ molecule.

As used herein, the term "$F(ab')_2$ fragment" comprises two light chains and two heavy chains containing part of the constant region between the $C_{H1}$ and $C_{H2}$ domains, such that interchain disulfide bonds are formed between the two heavy chains. Thus, the $F(ab')_2$ fragment consists of two Fab' fragments held together by disulfide bonds between the two heavy chains.

As used herein, the term "Fv region" comprises the variable regions from the heavy and light chains, but lacks the constant regions.

As used herein, the term "Fd" fragment refers to an antibody fragment consisting of $V_H$ and $C_{H1}$ domains (Ward et al., *Nature*, 341:544-546 (1989)).

As used herein, the term "dAb" fragment consists of $V_H$ domains (Ward et al., *Nature* 341:544-546 (1989)).

As used herein, the term "Fab'-SH" is the designation herein for Fab', wherein one or more cysteine residues of the constant domain carry a free thiol group.

As used herein, the term "Fab/c" fragment is an intermediate formed by pepsin digestion of an immunoglobulin, which combines the advantages of Fab and Fc regions, i.e., strong diffusibility and low metabolic clearance in vivo, while retaining high affinity (Liu Jianjun, *Chinese Journal of Cellular and Molecular Immunology*, 1989(4):29-29).

As used herein, the term "single chain antibody" is an Fv molecule in which the heavy and light chain variable regions are connected by a flexible linker to form a single polypeptide chain (which forms an antigen-binding region) (see, e.g., Bird et al., *Science*, 242:423-426 (1988), and Huston et al., *Proc. Natl. Acad. Sci. USA*, 90:5879-5883 (1988)). Single chain antibodies are described in detail in International Patent Publication No. WO88/01649 and U.S. Pat. Nos. 4,946,778 and 5,260,203, the disclosures of which are incorporated herein by reference.

As used herein, the term "domain antibody" is an immunofunctional immunoglobulin fragment that comprises only the variable region of the heavy chain or the light chain. In some cases, two or more $V_H$ regions are covalently linked by a peptide linker to generate a multivalent domain antibody (particularly a bivalent domain antibody). The two $V_H$ regions of the bivalent domain antibody may target the same or different antigens.

As used herein, the term "bivalent antigen-binding protein" or "bivalent antibody" comprises two antigen-binding sites. In some cases, the two binding sites have the same antigen specificity. The bivalent antibody may be bispecific.

As used herein, the term "multispecific antigen-binding protein" or "multispecific antibody" is an antigen-binding protein or antibody that targets more than one antigen or epitope.

As used herein, the term "bispecific", "dual-specificity" or "bifunctional" antigen-binding protein or antibody is a hybrid antigen-binding protein or antibody having two different antigen-binding sites, respectively. A bispecific antibody is a multispecific antigen-binding protein or a multispecific antibody, and can be produced by a variety of methods, including but not limited to, fusion of hybridomas or linkage of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen-binding protein or antibody will bind to two different epitopes present in the same or different protein targets.

As used herein, the terms "mAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody is highly specific for a single epitope on an antigen. The polyclonal antibody, relative to the monoclonal antibody, generally comprises at least two or more different antibodies which generally identify different epitopes on an antigen. Monoclonal antibodies can generally be obtained by hybridoma technique first reported by Kohler et al. (*Nature,* 256:495, 1975), and can also be obtained by recombinant DNA technique (for example, see U.S. Pat. No. 4,816,567).

As used herein, the term "humanized antibody" refers to an antibody or an antibody fragment obtained when all or part of the CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, e.g., Jones et al., *Nature*, 321:522-525 (1986); Reichmann et al., *Nature*, 332:323-329 (1988); Presta, *Curr. Op. Struct. Biol.*, 2:593-596 (1992); and Clark, *Immunol. Today* 21:397-402 (2000).

As used herein, the term "epitope" refers to a site on an antigen to which an immunoglobulin or an antibody specifically binds. "Epitope" is also called in the field as an "antigenic determinant". The epitope or antigenic determinant generally consists of chemically active surface groups of molecules such as amino acids, carbohydrates or sugar side chains, and usually has specific three-dimensional structural characteristics and specific charge characteristics. For example, the epitope generally comprises at least 3, 4, 5, 6, 7, 8, 9, 10, 11, 12, 13, 14, or 15 consecutive or non-consecutive amino acids in a unique spatial conformation, which can be "linear" or "conformational". See, e.g., Epitope Mapping Protocols in Methods in Molecular Biology, Vol. 66, G. E. Morris, Ed. (1996). In a linear epitope, all interaction sites between a protein and an interaction molecule (e.g., an antibody) are located linearly along the primary amino acid sequence of the protein. In a conformational epitope, the interaction sites are located across amino acid residues of a protein that are separated from each other.

The terms "polypeptide" or "protein" are used herein to refer to a polymer of amino acid residues. The term is also used to refer to an amino acid polymer in which one or more amino acid residues are analogs or mimetics of naturally existing amino acids, and for naturally existing amino acid polymers. The term may also include, for example, amino acid polymers that are modified by addition of saccharide residues to form glycoproteins, or that are phosphorylated. Polypeptides and proteins can be produced by naturally existing cells and non-recombinant cells, or they may be produced by genetically engineered or recombinant cells, and comprise a molecule having the amino acid sequence of a native protein or a molecule having deletions, insertions and/or substitutions in one or more amino acids of the native sequence.

Specifically, the terms "polypeptide" and "protein" include antibodies, such as anti-human p40 antibodies (also referred to as p40 antibodies), p40-binding proteins, and antibodies or sequences having deletions, insertions, and/or replacements in one or more amino acids of an antigen-binding protein.

The term "polypeptide fragment" refers to a polypeptide having an amino-terminal deletion, a carboxyl-terminal deletion, and/or an internal deletion as compared to a full-length protein. Such fragments may also comprise modified amino acids as compared to the full-length protein. In certain embodiments, such fragments are about 5 to 500 amino acids in length. For example, a fragment can be at least 5, 6, 8, 10, 14, 20, 50, 70, 100, 110, 150, 200, 250, 300, 350, 400 or 450 amino acids in length. Useful polypeptide fragments include immunologically functional fragments of antibodies, including binding domains. In the case of human p40 antibodies, useful fragments include but are not limited to CDR regions, variable domains of heavy or light chains, parts of antibody chains, variable domains exactly comprising 2 CDRs, or the like.

A "derivative" of a polypeptide is a polypeptide (e.g., an antigen-binding protein or an antibody) that is chemically modified in other manners than insertion, deletion or substitution, e.g., by conjugation with another chemical moiety, e.g., a PEG-conjugated polypeptide.

As used herein, the term "isolated" refers to being obtained by artificial means from a natural state. If a certain "isolated" substance or component appears in nature, it may be the case that change occurs in its natural environment, or that it is isolated from the natural environment, or both. For example, a certain non-isolated polynucleotide or polypeptide naturally exists in a certain living animal, and the same polynucleotide or polypeptide with a high purity isolated from such a natural state is called isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows for the expression of the protein encoded by the inserted polynucleotide, the vector is called an expression vector. A vector can be introduced into a host cell by transformation, transduction, or transfection so that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages; and animal viruses Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may comprise a variety of elements that control expression, including, but not limited to promoter sequences, transcription initiation sequences, enhancer sequences, selection elements, and reporter genes. In addition, the vector may further comprise a replication initiation site.

As used herein, the term "host cell" refers to cells that can be introduced with vectors, including, but not limited to, prokaryotic cells such as *E. coli* or *Bacillus subtilis*, fungal cells such as yeast cells or *aspergillus*, insect cells such as S2 *drosophila* cells or Sf9, or animal cells such as fibroblasts, CHO cells, COS cells, NSO cells, HeLa cells, BHK cells, HEK 293 cells or human cells.

As used herein, the term "specifically bind" refers to a non-random binding reaction between two molecules, such as a reaction between an antibody and an antigen it targets. In some embodiments, an antibody that specifically binds to an antigen (or an antibody that is specific for an antigen) means that the antibody binds to the antigen with an affinity ($K_D$) of less than about $10^{-5}$ M, such as less than about $10^{-6}$ M, $10^{-7}$ M, $10^{-8}$M, $10^{-9}$ M or $10^{-10}$ M or less.

As used herein, the term "$K_D$" refers to a dissociation equilibrium constant for a specific antibody-antigen interaction, which is used to describe the binding affinity between the antibody and the antigen. Among several parameters measured by molecular binding kinetics, the $K_D$ value is the dissociation equilibrium constant. In antibody drug research, it is the parameter characterizing the intensity of the affinity between an antibody of interest and the target antigen molecule, and is calculated by the formula: $K_D=k_{dis}/k_{on}$. A smaller equilibrium dissociation constant indicates a more intensive antibody-antigen binding and a higher affinity between the antibody and the antigen. $k_{on}$ (association rate constant) is the rate of antigen-antibody complex formation, and a smaller $k_{on}$ suggests a faster binding of an antibody to an antigen. $k_{dis}$ (dissociation rate constant) is the rate at which an antibody dissociates from an antigen-antibody complex, and a smaller $k_{dis}$ suggests a slower rate for the antibody dissociating from the antigen and a firmer binding between the antibody and the antigen. Generally, an antibody binds to an antigen (e.g., L1 protein) with a dissociation equilibrium constant ($K_D$) of less than about $10^{-5}$ M, such as less than about $10^{-6}$ M, $10^{-7}$ M, $10^{-8}$ M, $10^{-9}$ M or $10^{-10}$ M or less, for example, as determined by a Fortebio molecular interaction analyzer using biolayer interferometry (BLI) technique.

As used herein, the term "$EC_{50}$" refers to the effective concentration, 50% of the maximal response of an antibody.

As used herein, the terms "monoclonal antibody" and "McAb" have the same meaning and are used interchangeably; the terms "polyclonal antibody" and "PcAb" have the same meaning and are used interchangeably. Besides, herein, amino acids are generally represented by single-letter and three-letter abbreviations known in the art. For example, alanine can be represented by A or Ala.

As used herein, the terms "percent sequence identity" and "percent sequence homology" are used interchangeably.

As used herein, the terms "similarity", "sequence similarity" and "identity" refers to the correlation between the sequences of two or more protein or polypeptide molecules, as determined by aligning and comparing the sequences. "Percent identity" refers to the percentage of identical amino acid residues in the molecules compared, and can be calculated based on the size of the smallest molecule to be compared. For such calculations, gaps in the alignment (if any) must be addressed by a particular mathematical model or computer program (i.e., an "algorithm"). The term "substantial identity", when used for polypeptides, means that two peptide sequences, when optimally aligned, for example using the programs GAP or BESTFIT, using default gap weights provided by the programs, have at least 70%, 75% or 80% sequence identity, at least 90% or 95% sequence identity, or at least 97%, 98% or 99% sequence identity. In some cases, residue positions that are not identical differ by conservative amino acid substitutions. "Conservative amino acid substitution" is one in which the amino acid residue is replaced with another amino acid residue having a side chain R group with similar chemical properties (e.g., charge, hydrophilicity or hydrophobicity). Generally, conservative amino acid substitutions will substantially retain the functions and properties of the protein. In cases where two or more amino acid sequences differ from each other by conservative substitutions, the percent sequence identity may be elevated to correct for the conservative nature of the substitution. Methods for making this adjustment are well known to those skilled in the art. See, e.g., Pearson, *Methods Mol. Biol.,* 243:307-31 (1994). Examples of groups of amino acids having side chains with similar chemical properties include: 1) aliphatic hydroxyl side chain: glycine, alanine, valine, leucine and isoleucine, 2) aliphatic hydroxyl side chain: serine and threonine, 3) amide-containing side chain: asparagine and glutamine, 4) aromatic side chain: phenylalanine, tyrosine and tryptophan, 5) basic side chain: lysine, arginine and histidine, 6) acidic side chain: aspartic acid and glutamic acid, and 7) sulfur-containing side chain: cysteine and methionine. For example, the conservative amino acid substitution groups are valine-leucine-isoleucine-alanine-glycine, phenylalanine-tyrosine, lysine-arginine, threonine-serine, glutamic acid-aspartic acid and asparagine-glutamine.

Optionally, conservative substitution is any change with a positive value in the PAM250 log-likelihood matrix disclosed in Gonnet et al., *Science,* 256:1443-45 (1992), which is incorporated herein by reference. A "moderately conservative" substitution is any change with a non-negative value in the PAM250 log-likelihood matrix.

Sequence identity of polypeptides is usually measured by sequence analysis software. Protein analysis software matches sequences using a measure of similarity assigned to different substitutions, deletions and other modifications (including conservative amino acid substitutions). For example, GCG, including programs such as "Gap" and "Bestfit" which (using default parameters specified by the program) can be used to determine sequence homology or sequence identity between closely related polypeptides (e.g., homologous polypeptides from different biological species) or between a wild-type protein and its mutant protein. See, e.g., GCG Version 6.1 (University of Wisconsin, WI). Polypeptide sequences can also be compared using FASTA with default or recommended parameters. See GCG Version 6.10 FASTA (e.g., FASTA2 and FASTA3) which provides alignments for regions of optimal overlap between the challenge and query sequences and percent sequence identities (Pearson, Methods Enzymol. 183:63-98 (1990); Pearson, Methods Mol. Biol., 132:185-219 (2000)). Another preferred algorithm used when comparing sequences to a database containing massive sequences from different organisms is the computer program BLAST, in particular, blastp or blastn (using default parameters provided by the program). See, e.g., Altschul et al., *Mol. Biol.,* 215:403-410 (1990); Altschul et al., *Nucleic Acids Res.,* 25:3389-402 (1997).

The term "treatment" or "treating" usually refers to operations for acquiring needed pharmacological effect and/or physiological effect. In terms of fully or partially preventing a disease or a symptom thereof, the effect can be preventive; and/or in terms of partially or fully stabilizing or curing the disease and/or a side effect of the disease, the effect can be therapeutic. As used herein, "treatment" or "treating" covers any treatment to a disease in a patient, including (a) preventing a disease or a symptom of a disease from occurring in a patient that may be predisposed to the disease but has not yet been diagnosed as suffering from it; (b) inhibiting a symptom of a disease, i.e., arresting its development; or (c) relieving a symptom of a disease, i.e., causing regression of a disease or a symptom.

As used herein, the term "general treatment" refers to treatment in which a drug substance is transported through the bloodstream to reach and affect cells of the whole body.

As used herein, the term "systemic chemotherapy" refers to general chemotherapy that excludes chemotherapy for locally advanced disease as a part of multimodal treatment, wherein the chemotherapy for locally advanced disease includes induction chemotherapy, concurrent chemotherapy with radiotherapy, and adjuvant chemotherapy.

As used herein, the term "subject" (sometimes also referred to herein as "patient") refer to a mammal, such as a rodent, a feline, a canine and a primate. Preferably, the subject of the present invention is a human.

"Administer", "administration" or "administering" means physically introducing the composition comprising the therapeutic agent to a subject using any of a variety of methods and delivery systems known to those skilled in the art. Routes of administration for an inhibitor for an autoimmune disease-related factor (e.g., an anti-human IL-12/IL-23 p40 antibody) include intravenous, intramuscular, subcutaneous, intraperitoneal, spinal or other parenteral routes of administration, e.g., by injection or infusion. As used herein, the phrase "parenteral administration" refers to modes of administration except for enteral and local administration, typically by injection, including but not limited to, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion and in vivo electroporation. In certain embodiments, the inhibitor for an autoimmune disease-related factor (e.g., an anti-human IL-12/IL-23 p40 antibody) is administered by a non-parenteral route, and in some embodiments, it is administered orally. Other non-parenteral routes include local, epidermal or mucosal routes of administration, for example, intranasal, vaginal, rectal, sublingual or local administration. Administration may also be performed, e.g., once, multiple times, and/or over one or more extended periods of time.

A "subject" includes any human or non-human animal. The term "non-human animal" includes, but is not limited to, vertebrates such as non-human primates, sheep, dogs, and rodents such as mice, rats and guinea pigs. In certain embodiments, the subject is a human. The terms "subject" and "patient" are used interchangeably herein.

The terms "about", "approximately" or "substantially comprise" refers to a value or composition within an acceptable error range for the particular value or composition as determined by those of ordinary skill in the art, which will depend in part on how the value or composition is measured or determined, i.e., the limitations of the measurement system. For example, "about", "approximately" or "substantially comprise" may refer to being within 1 or more than 1 standard deviation as practiced in the art. Alternatively, "about" or "substantially comprise" may refer to a range that differs by up to 10% or 20% (i.e., ±10% or ±20%) from the parameter or value modified thereby. For example, about 3 mg may include any number between 2.7 mg and 3.3 mg (for 10%) or between 2.4 mg and 3.6 mg (for 20%).

Modes of Administration

The content below is not intended to limit the modes of administration of the medicament disclosed herein.

In an embodiment, the medicament disclosed herein can be formulated into a pharmaceutical composition which is suitable for a single dose or multiple doses.

The medicament disclosed herein is administered in various proper routes, including but not limited to, oral administration or parenteral administration (by intravenous, intramuscular, local or subcutaneous routes). In some embodiments, the medicament disclosed herein is administered by means of oral administration or injection, for example, intravenous injection or intraperitoneal injection.

Suitable dosage forms of the medicament disclosed herein include, but are not limited to, tablet, lozenge, pill, capsule (for example, hard capsule, soft capsule, enteric capsule and microcapsule), elixir, granule, syrup, injection (intramuscular, intravenous and intraperitoneal), granule, emulsion, suspension, solution, pulvis and dosage forms of sustained release formulations for oral or non-oral administration.

The medicament disclosed herein contains a pharmaceutically acceptable carrier and/or excipient.

Beneficial Effects of the Present Invention

The humanized antibodies against human IL-12/IL-23 p40 protein domain can specifically bind to the IL-12/IL-23 p40 protein domain, can effectively block the binding of the IL-12/IL-23 p40 protein domain to cell surface receptors IL-12Rβ1 and IL-23R, inhibit the activation of a signal pathway downstream of the human IL-12/IL-23 p40 protein domain and inhibit IL-23-induced IL-17A secretion. The binding activity of the antibodies disclosed herein to human p40 is significantly better than that of control antibodies ustekinumab and Ab123FR1. The antibodies disclosed herein have the potential of being used for preparing medicaments for preventing and treating autoimmune diseases (e.g., plaque psoriasis or systemic lupus erythematosus) and ulcerative colitis (e.g., refractory or recurrent). Meanwhile, they have good application prospect and market value.

DETAILED DESCRIPTION

Figure 1:
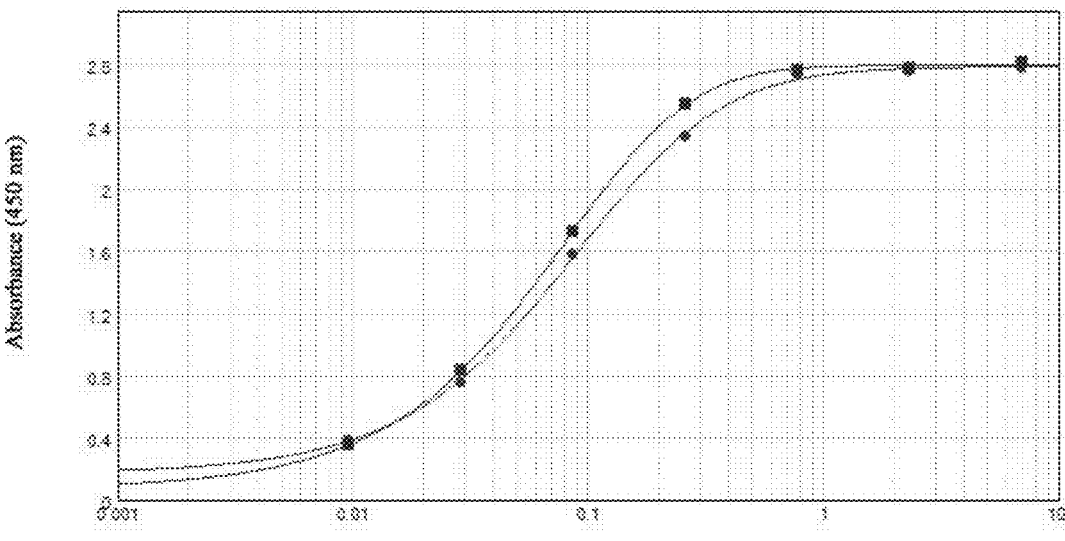
FIG. 1: detection results of binding activity of H5L9 and Ab123FR1 to human IL-12/IL-23 p40 protein domain.
Figure 1:

The embodiments of the present invention will be described in detail below with reference to the examples. Those skilled in the art will understand that the following examples are only used to illustrate the present invention, and should not be regarded as limiting the scope of the present invention. In the cases where the techniques or conditions are not specified, the examples were carried out according to the techniques or conditions described in the literature in the art (see, e.g., Molecular Cloning: A Laboratory Manual, authored by J. Sambrook et al., and translated by Huang Peitang et al., Third Edition, Science Press) or according to the product manual. Reagents or instruments used are commercially available conventional products if the manufacturers thereof are not specified.

In the following examples of the present invention, C57BL/6 mice were purchased from Guangdong Medical Laboratory Animal Center.

In the following examples of the present invention, IL-12 (Human IL12 (His Tag)) was purchased from Sino Biological (Cat. No.: CT-050-H08H-20, Lot No.: LC11MC2805).

In the following examples of the present invention, Ab123FR1, an anti-IL-12/IL-23 p40 antibody, was used as a control antibody, and reference can be made to the Chinese granted patent CN103275222B for its preparation method. It was produced by Akeso Biopharma, Inc, and its sequences were shown as positions 20-468 of SEQ ID NO: 3 and positions 20-233 of SEQ ID NO: 4 in CN103275222B.

In the following examples of the present invention, ustekinumab (trade name Stelara), a marketed anti-p40 antibody for the same target, was purchased from Johnson & Johnson as a control antibody.

In the following examples of the present invention, the cell line 293T-IL-12Rβ1&IL-23R used was constructed by Akeso Biopharma, Inc. The cell line 293T-IL-12Rβ1&IL-23R was prepared by viral infection of 293T cells using 3rd generation lentiviral systems (see, e.g., A Third Generation Lentivirus Vector with a Conditional Packaging System, Dull T, Zufferey R, Kelly M, Mandel R J, Nguyen M, Trono D, and Naldini L., *J Virol.* 1998. 72(11):8463-8471), wherein the lentivirus expression vectors used were pLenti-IL-12Rβ1-BSD (IL-12Rβ1, GenBank accession No. 3549; vector pLenti-BSD, purchased from Invitrogen, Cat. No.: K497000) and pCDH-IL-23R-puro (IL-23R, GenBank accession No. 149233; vector pCDH-CMV-MCS-EF1-Puro, purchased from Youbio, product No. VT1480).

The isotype control antibody was human anti-hen egg lysozyme IgG (anti-HEL, i.e., human IgG, abbreviated as hIgG1), and its sequence was from Affinity Maturation Increases the Stability and Plasticity of the Fv Domain of Anti-Protein Antibodies (Acierno et al., *J Mol Biol.*, 2007, 374(1):130-46, wherein the amino acid sequence of the heavy chain is set forth in SEQ ID NO: 21, and the amino acid sequence of the light chain is set forth in SEQ ID NO: 22). The isotype control antibody was prepared in the laboratory of Akeso Biopharma, Inc.

The hIL-23 recombinant protein (IL-23, GeneBank accession No. 51561) was prepared in the laboratory of Akeso Biopharma, Inc.

The following examples are further illustration of the present invention and are not intended to limit the present invention.

Example 1. Design, Expression and Purification of Heavy Chain and Light Chain Sequences of Anti-Human p40 Antibody H8L15

1. Design of Antibodies

To prepare anti-human IL-12/IL-23 p40 antibody H8L15, the inventors determined amino acid sequences of the CDR regions where the antibody binds to the antigen by quantum simulation calculation based on the structure of IL-12/IL-23 p40 protein domain and by means of structural biology-based three-dimensional space structure simulation technology for antigen-antibody binding and the interaction between the CDR regions of the antibody and the antigen. Meanwhile, the framework part of the antibody was optimized correspondingly without influencing the three-dimensional structure of the CDR regions, and finally antibodies H5L9, H5L10, H5L11, H5L12, H5L14 and H8L15 specifically biding to human IL-12/IL-23 p40 were obtained.

The amino acid sequences of the heavy chain variable regions and the light chain variable regions of the antibodies and the encoding DNA sequences thereof are as follows:

H5L9: the amino acid sequence of the heavy chain variable region is set forth in SEQ ID NO: 1, and the encoding DNA sequence thereof is set forth in SEQ ID NO: 2;

H5L9: the amino acid sequence of the light chain variable region is set forth in SEQ ID NO: 6, and the encoding DNA sequence thereof is set forth in SEQ ID NO: 7;

H5L10: the amino acid sequence of the heavy chain variable region is set forth in SEQ ID NO: 1, and the encoding DNA sequence thereof is set forth in SEQ ID NO: 2;

H5L10: the amino acid sequence of the light chain variable region is set forth in SEQ ID NO: 11, and the encoding DNA sequence thereof is set forth in SEQ ID NO: 12;

H5L11: the amino acid sequence of the heavy chain variable region is set forth in SEQ ID NO: 1, and the encoding DNA sequence thereof is set forth in SEQ ID NO: 2;

H5L11: the amino acid sequence of the light chain variable region is set forth in SEQ ID NO: 13, and the encoding DNA sequence thereof is set forth in SEQ ID NO: 14;

H5L12: the amino acid sequence of the heavy chain variable region is set forth in SEQ ID NO: 1, and the encoding DNA sequence thereof is set forth in SEQ ID NO: 2;

H5L12: the amino acid sequence of the light chain variable region is set forth in SEQ ID NO: 15, and the encoding DNA sequence thereof is set forth in SEQ ID NO: 16;

H5L14: the amino acid sequence of the heavy chain variable region is set forth in SEQ ID NO: 1, and the encoding DNA sequence thereof is set forth in SEQ ID NO: 2;

H5L14: the amino acid sequence of the light chain variable region is set forth in SEQ ID NO: 17, and the encoding DNA sequence thereof is set forth in SEQ ID NO: 18;

H8L15: the amino acid sequence of the heavy chain variable region is set forth in SEQ ID NO: 24, and the encoding DNA sequence thereof is set forth in SEQ ID NO: 37;

H8L15: the amino acid sequence of the light chain variable region is set forth in SEQ ID NO: 25, and the encoding DNA sequence thereof is set forth in SEQ ID NO: 38

2. Expression and Purification of Antibodies

The encoding nucleotide sequence of the heavy chain variable region (set forth in SEQ ID NO: 37; constant region: Ig gamma-1 chain C region; ACCESSION: P01857) and the encoding nucleotide sequence of the light chain variable region (set forth in SEQ ID NO: 38; constant region: Ig kappa chain C region; ACCESSION: P01834) of the above-described antibodies, such as H8L15, were each cloned into vector pUC57simple (provided by Genscript) to obtain pUC57simple-H8L15H containing the full-length heavy chain nucleotide of H8L15 and pUC57simple-H8L15L containing the full-length light chain nucleotide of H8L15, respectively.

Plasmids pUC57simple-H8L15H and pUC57simple-H8L15L were digested (HindIII & EcoRI), and heavy and light chain nucleotide sequences isolated by electrophoresis were subcloned into vector pcDNA3.1, and recombinant plasmids were extracted to co-transfect 293F cells. After the transfected 293F cells were cultured for 7 days, the culture medium was centrifuged at high speed, and the obtained supernatant was concentrated and loaded onto a HiTrap MabSelect SuRe column. The protein was eluted in one step with the eluent to isolate the target sample. The antibody sample was stored in PBS buffer.

Other antibodies were prepared in the same way. The antibodies H5L9, H5L10, H5L11, H5L12, H5L14 and H8L15 prepared in this example were used in the following Examples 2-4.

Example 2. Detection of Binding Activity of Antibodies H5L9, H5L10, H5L11, H5L12, H5L14, H8L15, Ab123FR1 and Ustekinumab to Antigen Human IL-12/IL-23 p40 by ELISA A microplate was coated with human p40-His (Akeso Biopharma, Inc.; gene of p40: GeneBank NM002187). After incubation at 4° C. for no less than 12 h, the plate was washed with PBST, patted dry and blocked with a solution of 1% BSA in PBS. After blocking was completed, the plate was washed with PBST and patted dry. The antibody diluted with PBST solution in gradient was added into the wells of the plate, and the antibody dilution gradient is detailed in Table 1. The plate containing the test antibody was incubated at 37° C. for 30 min and then washed with PBST and patted dry. HRP-labeled goat anti-human IgG (H+L) (purchased from Jackson ImmunoResearch Inc., Cat. No.: 109-035-088) secondary antibody working solution diluted at a ratio of 1:5000 was added, and the resulting mixture was incubated at 37° C. for 30 min After the incubation, the plate was washed with PBST and patted dry. TMB (Neogen, 308177) was added for color developing for 5 min in the absence of light, and then stop solution was added to terminate the chromogenic reaction. Then the plate was put into a plate reader immediately, and the OD value of each well in the plate was read at 450 nm. The data were analyzed by SoftMax Pro 6.2.1.

The detection results of the binding of antibodies H5L9 and Ab123FR1 to the antigen human p40-His are shown in FIG. 1. The OD values for all the dosages are shown in Table 1. The binding $EC_{50}$ of antibody was calculated by curve fitting using antibody concentration as the abscissa and absorbance value as the ordinate, and the results are shown in Table 1 below.

Figure 2:
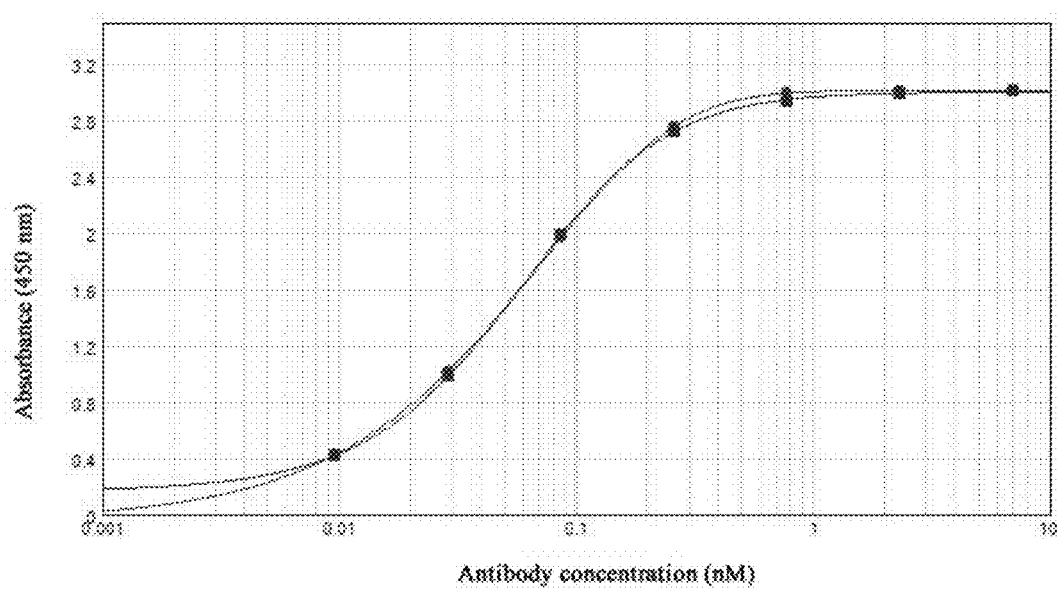
FIG. 2: detection results of binding activity of H5L10 and Ab123FR1 to human IL-12/IL-23 p40 protein domain.
Figure 2:

The detection results of the binding of antibodies H5L10 and Ab123FR1 to the antigen human p40-His are shown in FIG. 2. The OD values for all the dosages are shown in Table 2. The binding $EC_{50}$ of antibody was calculated by curve fitting using antibody concentration as the abscissa and absorbance value as the ordinate, and the results are shown in Table 2 below.

Figure 3:
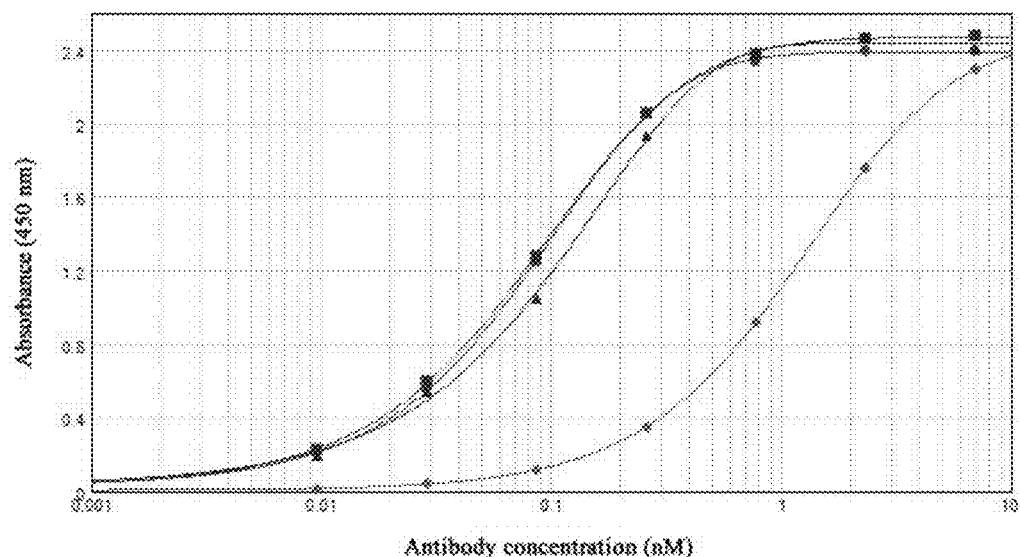
FIG. 3: detection results of binding activity of H5L11, H5L12, H5L14 and Ab123FR1 to human IL-12/IL-23 p40 protein domain.
Figure 3:
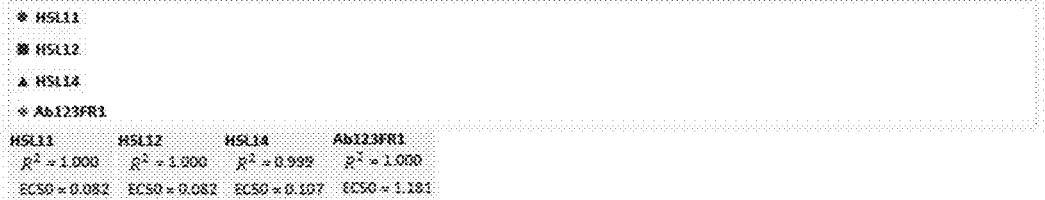

The detection results of the binding of antibodies H5L11, H5L12, H5L14 and Ab123FR1 to the antigen human p40-His are shown in FIG. 3. The OD values for all the dosages are shown in Table 3. The binding $EC_{50}$ of antibody was calculated by curve fitting using antibody concentration as the abscissa and absorbance value as the ordinate, and the results are shown in Table 3 below.

Figure 4:
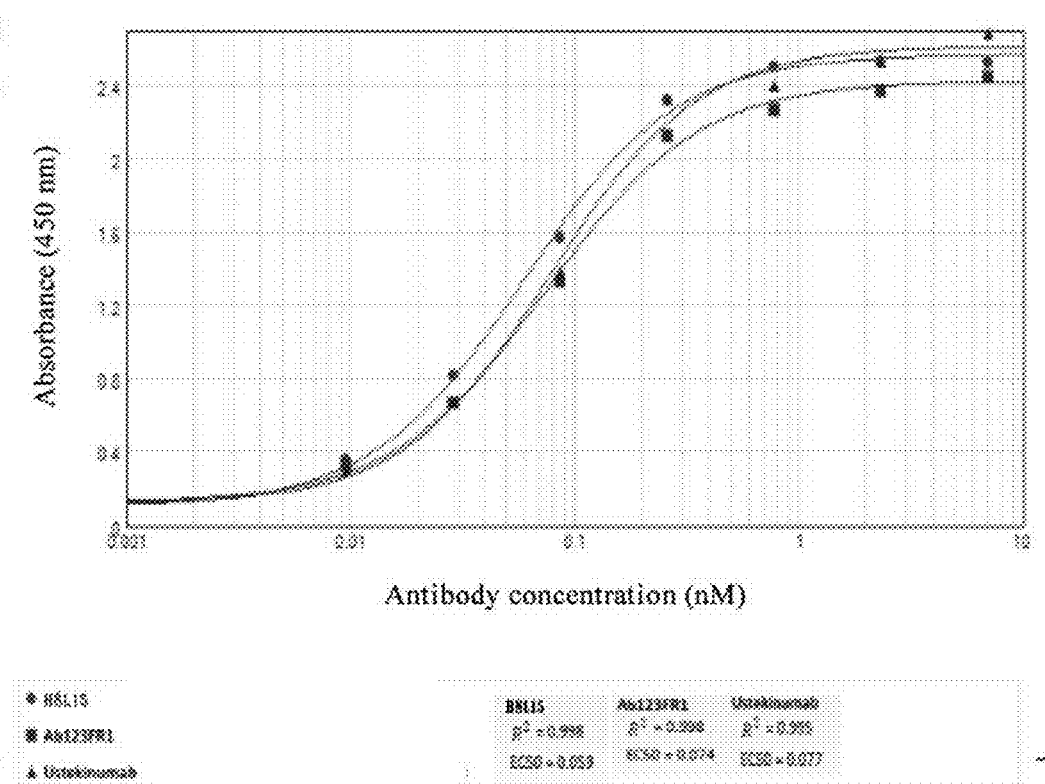
FIG. 4: detection results of activity of H8L15 and Ab123FR1 to human IL-12/IL-23 p40 protein domain.
Figure 5:
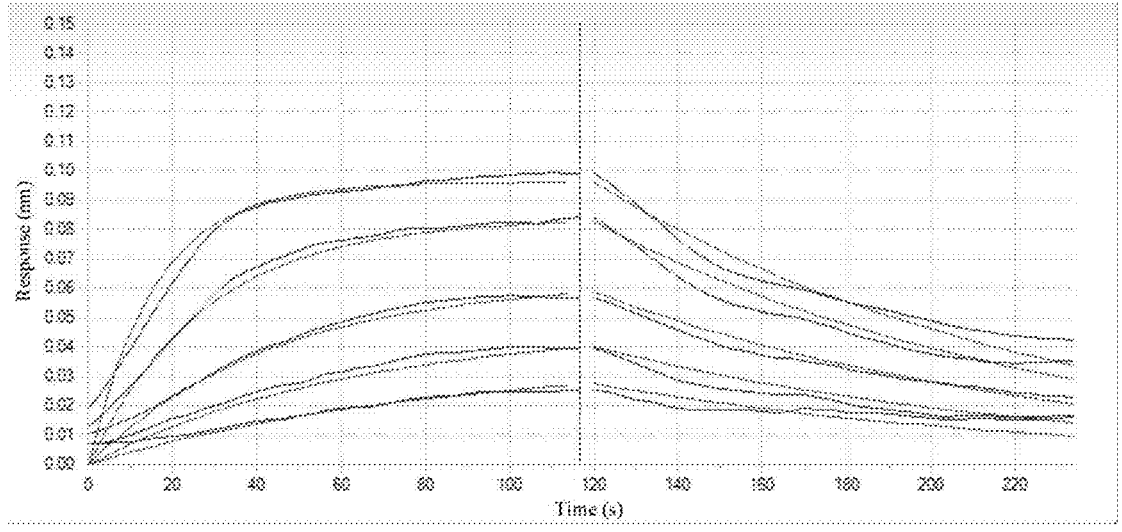
FIG. 5: detection results of affinity constant of H5L9 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 6:
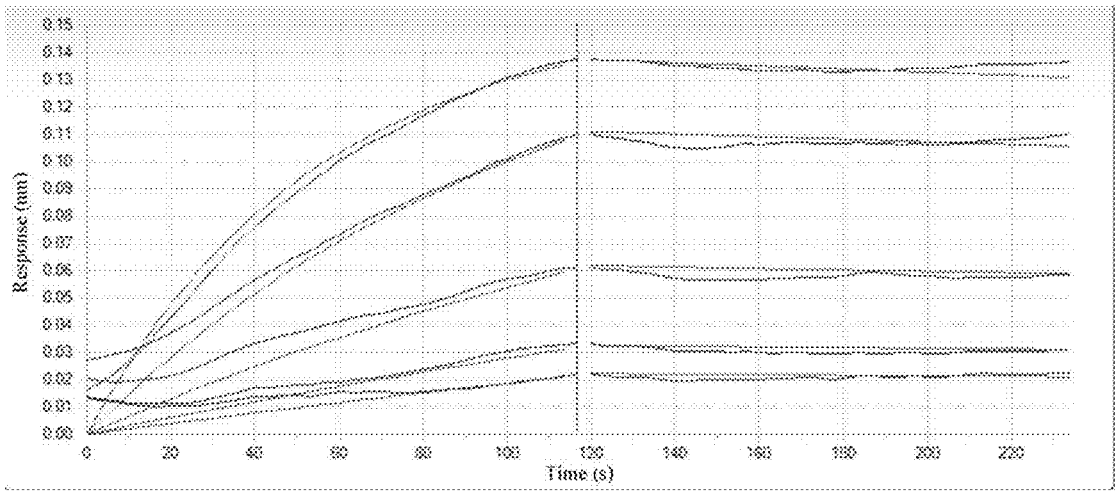
FIG. 6: detection results of affinity constant of H5L10 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 7:
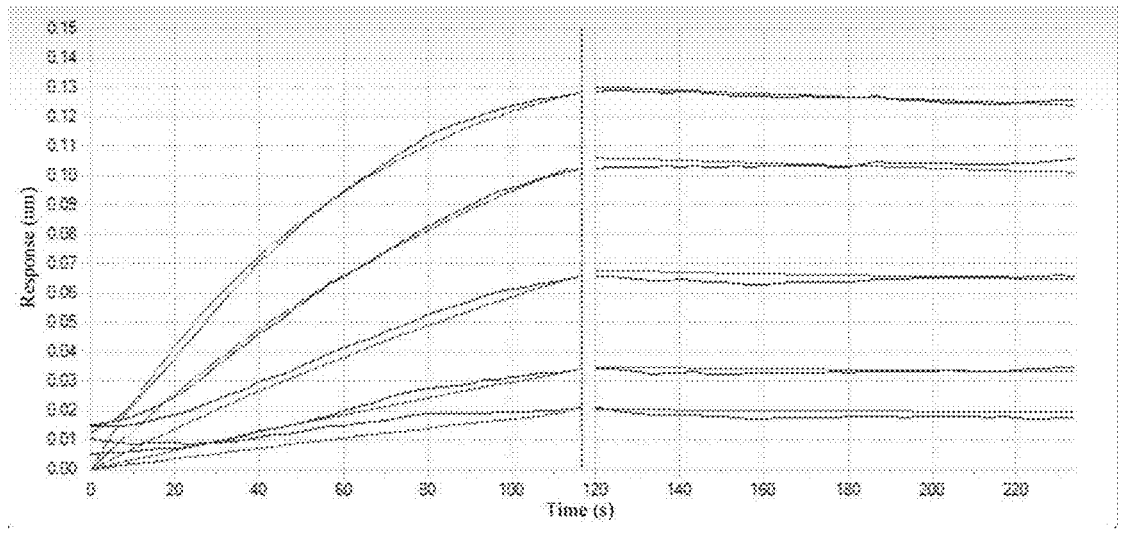
FIG. 7: detection results of affinity constant of H5L11 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 8:
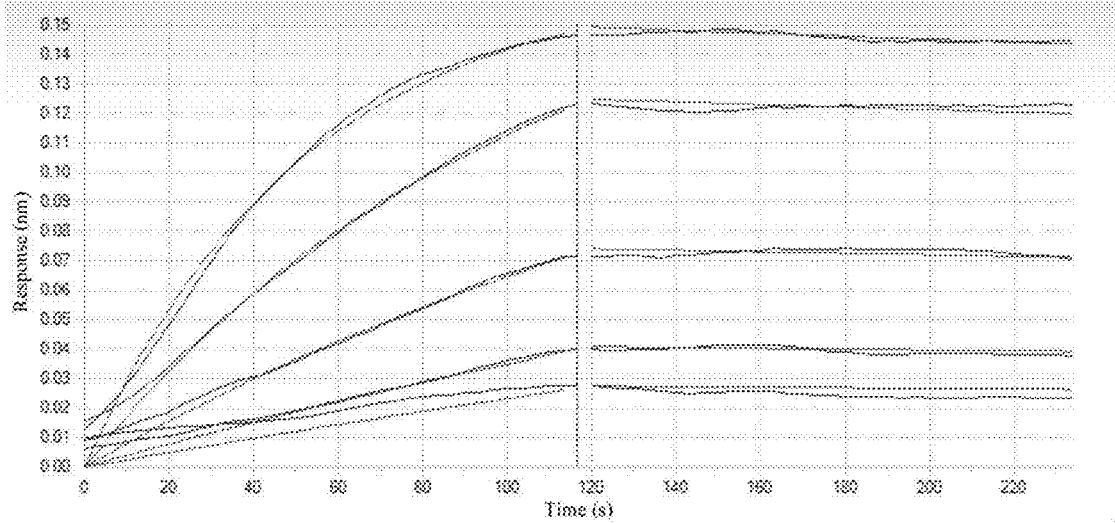
FIG. 8: detection results of affinity constant of H5L12 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 9:
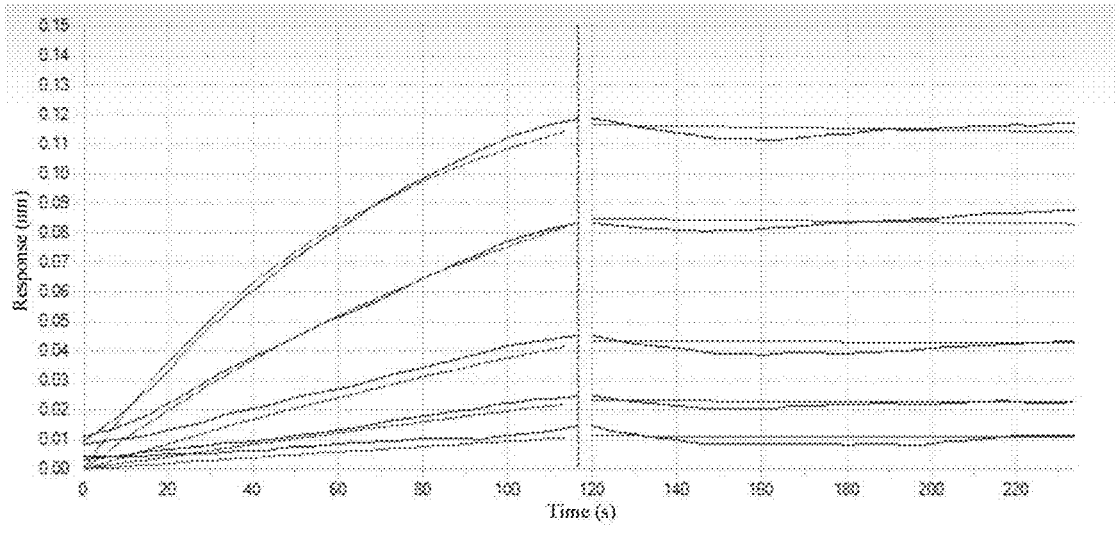
FIG. 9: detection results of affinity constant of H5L14 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 10:
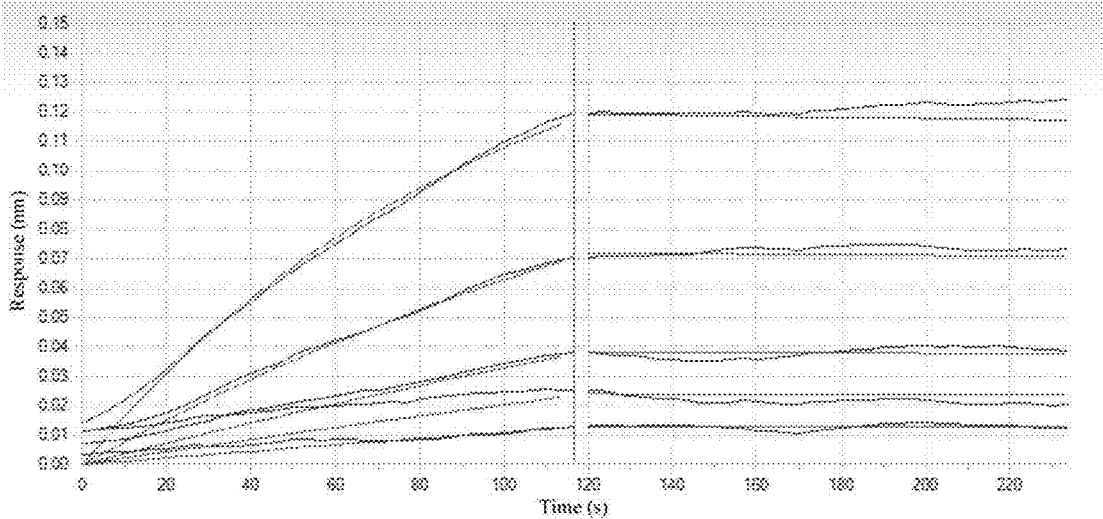
FIG. 10: detection results of affinity constant of Ab123FR1 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 11:
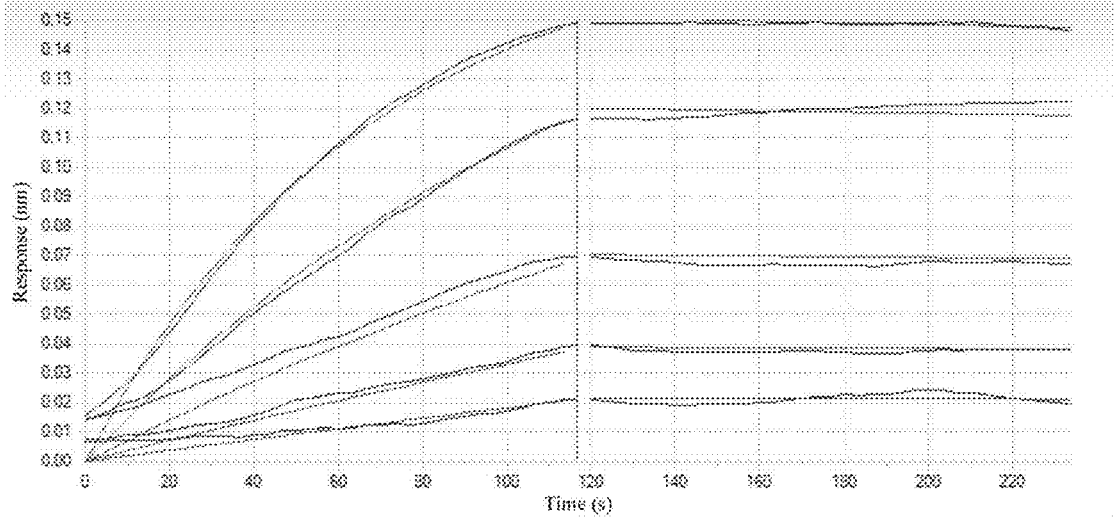
FIG. 11: detection results of affinity constant of H8L15 for human IL-12/IL-23 p40 protein domain. The antibody concentrations for the curve pairs from top to bottom are 5 nM, 2.5 nM, 1.25 nM, 0.75 nM and 0.31 nM, respectively.
Figure 12:
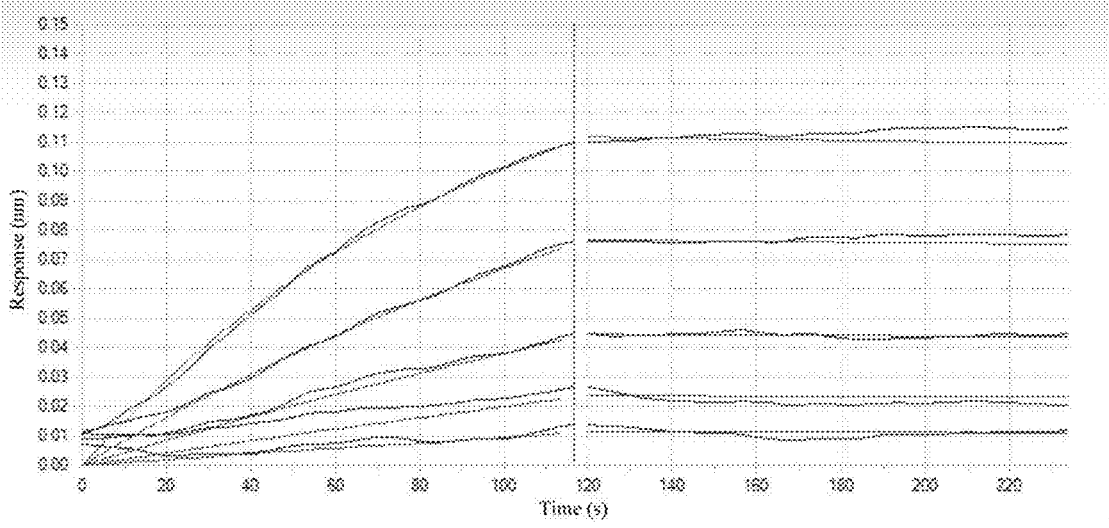
FIG. 12: detection results of affinity constant of ustekinumab for human IL-12/IL-23 p40 protein domain. The antibody concentrations for the curve pairs from top to bottom are 5 nM, 2.5 nM, 1.25 nM, 0.75 nM and 0.31 nM, respectively.

The detection results of the binding of antibodies H8L15 and Ab123FR1 to the antigen human p40-His are shown in FIG. 4. The OD values for all the dosages are shown in Table 4. The binding $EC_{50}$ of antibody was calculated by curve fitting using antibody concentration as the abscissa and absorbance value as the ordinate, and the results are shown in Table 4 below.

The results show that the binding efficiency of H5L9, H5L10, H5L11, H5L12, H5L14 and H8L15 to the antigen human p40-His is dose-dependent.

As shown in FIG. 1 and Table 1, H5L9 binds to human p40-His with an $EC_{50}$ of 0.079 nM, and Ab123FR1 binds to human p40-His with an $EC_{50}$ of 0.063 nM. The binding efficiency of H5L9 is comparable to that of Ab123FR1.

As shown in FIG. 2 and Table 2, H5L10 binds to human p40-His with an $EC_{50}$ of 0.057 nM, and Ab123FR1 binds to human p40-His with an $EC_{50}$ of 0.051 nM. The binding efficiency of H5L10 is comparable to that of Ab123FR1.

As shown in FIG. 3 and Table 3, H5L11, H5L12, H5L14 and Ab123FR1 bind to human p40-His with $EC_{50}$ values of 0.082 nM, 0.082 nM, 0.107 nM and 1.181 nM, respectively. The binding efficiency of H5L11, H5L12 and H5L14 is obviously better than that of Ab123FR1.

As shown in FIG. 4 and Table 4, H8L15, Ab123FR1 and ustekinumab bind to human p40-His with $EC_{50}$ values of 0.059 nM, 0.074 nM and 0.077 nM, respectively. In terms of binding efficiency, Ab123FR1 is comparable to ustekinumab, while H8L15 is significantly better than the two.

TABLE 1

| Binding activity of H5L9 to human p40-His | | | |
|---|---|---|---|
| Antibody Concentration | Antigen coating: p40-His (0.125 µg/mL) | | |
| (µg/mL) | Ab123FR1 | | H5L9 |
| 1.000 | 2.884 | 2.863 | 2.817 | 2.860 |
| 0.333 | 2.818 | 2.838 | 2.864 | 2.776 |
| 0.111 | 2.806 | 2.833 | 2.768 | 2.831 |
| 0.037 | 2.543 | 2.650 | 2.318 | 2.463 |
| 0.012 | 1.751 | 1.792 | 1.649 | 1.622 |
| 0.004 | 0.849 | 0.918 | 0.801 | 0.820 |
| 0.001 | 0.357 | 0.441 | 0.386 | 0.497 |
| PBS | 0.046 | 0.046 | 0.052 | 0.052 |
| Second antibody | HRP-labeled goat anti-human IgG (H + L) (1:5000) | | |
| $EC_{50}$(nM) | 0.063 | | 0.079 |

TABLE 2

| Binding activity of H5L10 to human p40-His | | | |
|---|---|---|---|
| Antibody Concentration | Antigen coating: p40-His (0.125 µg/mL) | | |
| (µg/mL) | Ab123FR1 | | H5L10 |
| 1.000 | 3.070 | 3.071 | 3.052 | 3.094 |
| 0.333 | 3.074 | 3.081 | 3.066 | 3.030 |
| 0.111 | 3.085 | 3.043 | 2.977 | 3.022 |
| 0.037 | 2.853 | 2.788 | 2.794 | 2.784 |
| 0.012 | 2.164 | 1.894 | 1.981 | 2.104 |
| 0.004 | 1.229 | 0.935 | 1.058 | 1.030 |
| 0.001 | 0.532 | 0.438 | 0.490 | 0.464 |
| PBS | 0.062 | 0.059 | 0.059 | 0.057 |
| Second antibody | HRP-labeled goat anti-human IgG (H + L) (1:5000) | | |
| $EC_{50}$(nM) | 0.051 | | 0.057 |

TABLE 3

| Binding activity of H5L11, H5L12 and H5L14 to human p40 | | | | | | | | | |
|---|---|---|---|---|---|---|---|---|---|
| Antibody Concentration | Antigen coating: p40-His (0.125 μg/mL) | | | | | | | | |
| (μg/mL) | H5L11 | | H5L12 | | H5L14 | | Ab123FR1 | | | |
| 1 | 2.474 | 2.410 | 2.518 | 2.542 | 2.475 | 2.429 | 2.386 | 2.342 | 2.353 | 2.282 |
| 0.3 | 2.472 | 2.409 | 2.541 | 2.473 | 2.576 | 2.471 | 1.815 | 1.736 | 1.801 | 1.862 |
| 0.1 | 2.392 | 2.382 | 2.486 | 2.371 | 2.488 | 2.386 | 0.864 | 0.946 | 0.971 | 1.091 |
| 0.03 | 2.132 | 2.074 | 2.096 | 2.111 | 1.995 | 1.964 | 0.356 | 0.372 | 0.408 | 0.438 |
| 0.01 | 1.279 | 1.310 | 1.334 | 1.309 | 1.196 | 0.995 | 0.149 | 0.168 | 0.165 | 0.180 |
| 0.003 | 0.613 | 0.593 | 0.625 | 0.665 | 0.603 | 0.580 | 0.082 | 0.083 | 0.084 | 0.089 |
| 0.001 | 0.269 | 0.242 | 0.286 | 0.263 | 0.237 | 0.256 | 0.056 | 0.060 | 0.056 | 0.062 |
| 0 | 0.045 | 0.046 | 0.045 | 0.047 | 0.046 | 0.049 | 0.048 | 0.037 | 0.041 | 0.046 |
| Second antibody | HRP-labeled goat anti-human IgG (H + L) (1:5000) | | | | | | | | | |
| EC$_{50}$(nM) | 0.082 | | 0.082 | | 0.107 | | 1.181 | | | |

TABLE 4

| Binding activity of H8L15 to human p40-His | | | | | | |
|---|---|---|---|---|---|---|
| Antibody Concentration | Antigen coating: p40-His (0.25 μg/mL) | | | | | |
| (μg/mL) | H8L15 | | Ab123FR1 | | Ustekinumab | |
| 1.0000 | 2.584 | 2.470 | 2.466 | 2.425 | 2.686 | 2.690 |
| 0.3333 | 2.519 | 2.551 | 2.325 | 2.425 | 2.521 | 2.555 |
| 0.1111 | 2.520 | 2.490 | 2.241 | 2.301 | 2.473 | 2.334 |
| 0.0370 | 2.376 | 2.280 | 2.190 | 2.055 | 2.317 | 2.329 |
| 0.0123 | 1.602 | 1.537 | 1.300 | 1.373 | 1.377 | 1.386 |
| 0.0041 | 0.835 | 0.801 | 0.663 | 0.675 | 0.686 | 0.656 |
| 0.0014 | 0.370 | 0.351 | 0.312 | 0.340 | 0.310 | 0.284 |
| 0.0000 | 0.069 | 0.068 | 0.096 | 0.087 | 0.090 | 0.078 |
| Second antibody | HRP-labeled goat anti-human IgG (H + L) (1:5000) | | | | | |
| EC$_{50}$(nM) | 0.059 | | 0.074 | | 0.077 | |

Example 3. Determination of Affinity Constants of H5L9, H5L10, H5L11, H5L12, H5L14, H8L15, Ab123FR1 and Ustekinumab for Antigen Human IL-12/IL-23 p40 by Fortebio The sample dilution buffer for H5L9, H5L10, H5L11, H5L12, H5L14, H8L15, Ab123FR1 and ustekinumab was quency was 0.3 Hz, and the sample plate shaking rate was 500 rpm. The data were analyzed by 1:1 model fitting to obtain affinity constants.

The determination results of the affinity constants of humanized antibodies H5L9, H5L10, H5L11, H5L12, H5L14, Ab123FR1, H8L15 and ustekinumab (as control antibody) for human p40-His are shown in Table 5, and the detection results are shown in FIGS. 5, 6, 7, 8, 9, 10, 11 and 12.

The results show that: the affinity constant of H5L9 for human p40-His is 8.49E-10M, the affinity constant of H5L10 for human p40-His is 1.21E-10M, the affinity constant of H5L11 for human p40-His is 1.36E-10M, the affinity constant of H5L12 for human p40-His is 9.05E-11M, the affinity constant of H5L14 for human p40-His is 6.20E-11M, the affinity constant of Ab123FR1 for human p40-His is 7.40E-11M, the affinity constant of H8L15 for human p40-His is 6.09E-11M, and the affinity constant of ustekinumab for human p40-His is 8.64E-11M.

In terms of affinity, the antibodies were ranked as follows from strong to weak: H8L15, H5L14, Ab123FR1, ustekinumab, H5L12, H5L10, H5L11 and H5L9 H8L15 and H5L14 show stronger affinity for human p40-His than Ab123FR1 and ustekinumab.

TABLE 5

| Affinity constants of H5L9, H5L10, H5L11, H5L12, H5L14, H8L15, Ab123FR1 and ustekinumab for human p40-His | | | | | | |
|---|---|---|---|---|---|---|
| Test antibodies | K$_D$ (M) | kon(l/Ms) | S E (kon) | kdis(1/s) | S E(kdis) | Rmax(nm) |
| H5L9 | 8.49E-10 | 1.08E+07 | 8.50E+05 | 9.20E-03 | 3.07E-04 | 0.11-0.13 |
| H5L10 | 1.21E-10 | 3.58E+06 | 3.64E+05 | 4.35E-04 | 2.22E-04 | 0.14-0.18 |
| H5L11 | 1.36E-10 | 3.15E+06 | 2.32E+05 | 4.28E-04 | 1.44E-04 | 0.16-0.19 |
| H5L12 | 9.05E-11 | 3.84E+06 | 2.12E+05 | 3.48E-04 | 1.24E-04 | 0.17-0.21 |
| H5L14 | 6.20E-11 | 2.94E+06 | 2.36E+05 | 1.82E-04 | 1.58E-04 | 0.11-0.15 |
| Ab123FR1 | 7.40E-11 | 2.00E+06 | 2.89E+05 | 1.48E-04 | 2.15E-04 | 0.15-0.18 |
| H8L15 | 6.09E-11 | 2.95E+06 | 2.13E+05 | 1.80E-04 | 1.37E-04 | 0.18-0.21 |
| Ustekinumab | 8.64E-11 | 1.99E+06 | 2.51E+05 | 1.72E-04 | 1.81E-04 | 0.16-0.17 |

K$_D$ is the affinity constant; K$_D$ = k$_{dis}$/k$_{on}$.

PBS (0.02% Tween-20, 0.1% BSA, pH 7.4). p40-His was immobilized on a HIS1K (manufacturer: Fortebio, Cat. No.: 18-5120) sensor at a concentration of 1 μg/mL for 40 s. The sensor was equilibrated in a buffer for 60 s, and the p40-His immobilized on the sensor bound to the antibody at a concentration of 5-0.31 nM (two-fold dilution) for 120 s, and then the protein dissociated in the buffer for 300 s. The sensor was refreshed with 10 mM glycine solution (pH=1.5). The detection temperature was 37° C., the detection fre-

Example 4. Detection of Anti-Human IL-12/IL-23 p40 Antibodies Competitively Blocking the Binding of Human IL-12 and IL-23 to 293T-IL-12Rβ1&IL-23R Cells by Flow Cytometry 1.1. Detection of Antibodies H5L9, H5L10, H5L11, H5L12, H5L14 and Ustekinumab Competitively Blocking the Binding of Human IL-12 to 293T-IL-12Rβ1&IL-23R Cells by Flow Cytometry 293T-IL-12Rβ1&IL-23R cells were digested in a conventional way and divided into several samples with 300,000 cells for each. 200 μL of 1% PBSA was added into each sample, and the mixture was centrifuged at 700×g for 5 min to discard the supernatant. According to experiment design, correspondingly diluted antibody (highest final concentration of 30 μg/mL, 3-fold dilution, 8 concentrations in total) and human IL-12 (Sino Biological, Cat. No.: CT-050-H08H-20) (final concentration of 20 nM) were mixed at a ratio of 1:1, and a blank control was set. The mixture of antibody and human IL12 was incubated on ice for 30 min and then added to the cell precipitate at 100 μL/sample. The resulting mixture was well mixed and incubated on ice for 60 min 200 μL of 1% PBSA was added, and the mixture was centrifuged at 700×g for 5 min to discard the supernatant, and then washed twice. Alexa Fluor® 488 anti-His tag antibody (Biolegend, Cat. No.: 652509) was diluted at a ratio of 1:400 and added to each tube at 100 μL. The mixture was well mixed and incubated on ice for 40 min in the absence of light. 200 μL of 1% PBSA was added, and the mixture was centrifuged at 700×g for 5 min to discard the supernatant, and then washed twice. 1% PBSA was added at 200 μL/tube, and the cells were resuspended and transferred to a flow cytometry tube for testing. The results of antibodies H5L9, H5L10, H5L11, H5L12, H5L14 and ustekinumab competitively blocking the binding of human IL-12 to 293T-IL-12Rβ1&IL-23R cells detected by FACS are shown in Table 6 and FIG. 13.

Figure 13:
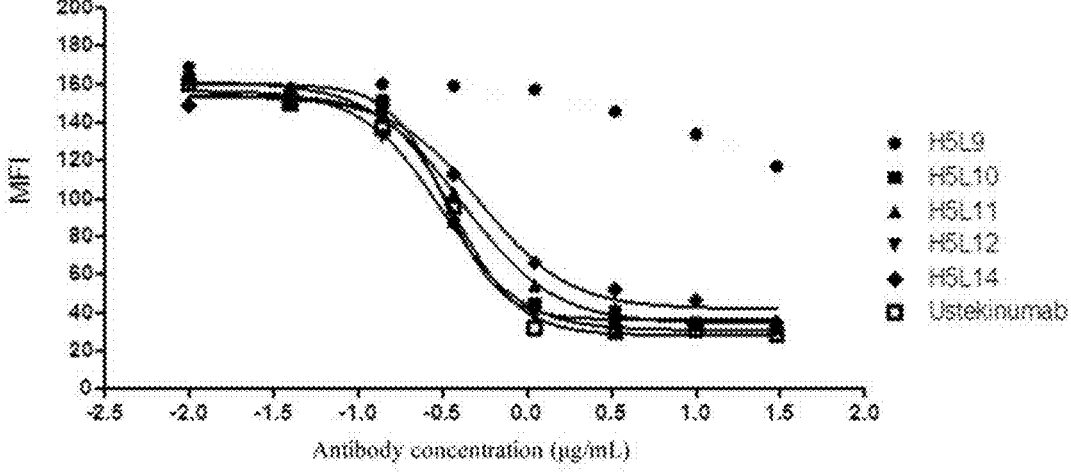
FIG. 13: antibodies H5L9, H5L10, H5L11, H5L12, H5L14 and ustekinumab competitively blocking the binding of human IL-12 to 293T-IL-12Rβ1&IL-23R cells (FACS).

According to the results shown in Table 6 and FIG. 13, H5L9, H5L10, H5L11, H5L12, H5L14 and ustekinumab all can competitively block the binding of IL-12 to IL-12Rβ1 on the cell membrane surface of 293T-IL-12Rβ1&IL-23R, wherein the competitive binding activity of H5L9 is not significant, and the competitive binding $EC_{50}$ values of H5L10, H5L11, H5L12, H5L14 and ustekinumab are 0.3312 μg/mL, 0.414 μg/mL, 0.3172 μg/mL, 0.5320 μg/mL and 0.3770 μg/mL, respectively.

In terms of strength for competitively blocking the binding of IL-12 to IL-12Rβ1 on the cell membrane surface of 293T-IL-12Rβ1&IL-23R, the antibodies were ranked as follows from strong to weak: H5L12, H5L10, ustekinumab, H5L11, H5L14 and H5L9.

The above results show that the competitive binding activity of H5L12 and H5L10 for competitively blocking the binding of IL-12 to IL-12Rβ1 on the cell membrane surface is better than that of ustekinumab.

1.2. Detection of Antibodies Ab123FR1, H8L15 and Ustekinumab Competitively Blocking the Binding of Human IL-12 to 293T-IL-12Rβ1&IL-23R Cells by Flow Cytometry 293T-IL-12Rβ1 &IL-23R cells were digested in a conventional way and divided into several samples with 300, 000 cells for each. 200 μL of 1% PBSA was added into each sample, and the mixture was centrifuged at 1200 rpm for 5 min to discard the supernatant. According to experiment design, correspondingly diluted antibody (highest final concentration of 60 μg/mL, 3-fold dilution, 8 concentrations in total) and IL12-His (Sino Biological, Cat. No.: CT-050-H08H-20) (40 nM) were mixed at a ratio of 1:1, and a blank control was set. The mixture of antibody and IL12 was incubated on ice for 30 min and then added to the cell precipitate at 100 μL/sample. The resulting mixture was well mixed and incubated on ice for 60 min 200 μL of 1% PBSA was added, and the mixture was centrifuged at 1200 rpm for 5 min to discard the supernatant, and then washed twice. THE™ His tag antibody (FITC) (Genscript, Cat. No.: A01620) was diluted at a ratio of 1:500 and added to each tube at 100 μL. The mixture was well mixed and incubated on ice for 40 min in the absence of light. 200 μL of 1% PBSA was added, and the mixture was centrifuged at 1200 rpm for 5 min to discard the supernatant, and then washed twice. 1% PBSA was added at 200 μL/tube, and the cells were resuspended and transferred to a flow cytometry tube for testing. The results of antibodies Ab123FR1, H8L15 and ustekinumab competitively blocking the binding of human IL-12 to 293T-IL-12Rβ1&IL-23R cells detected by FACS are shown in Table 7 and FIG. 20.

Figure 20:
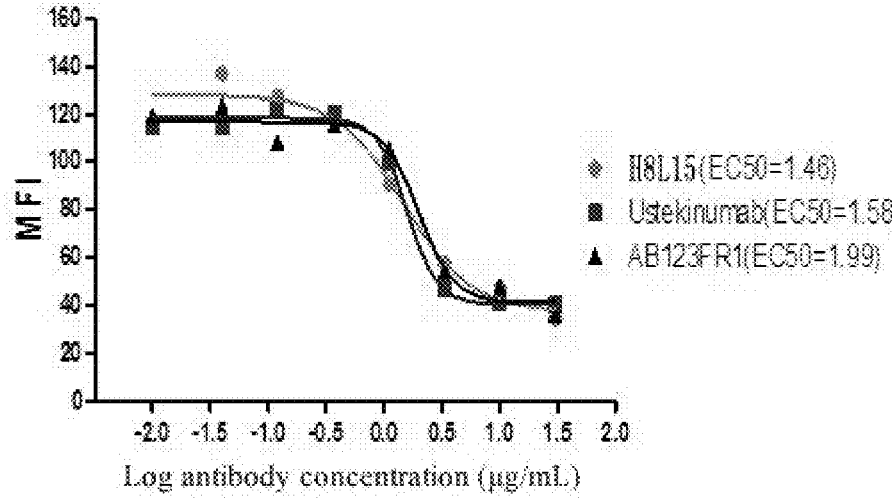
FIG. 20: antibodies Ab123FR1, H8L15 and ustekinumab competitively blocking the binding of human IL-12 to 293T-IL-12Rβ1&IL-23R cells (FACS).

According to the results shown in Table 7 and FIG. 20, Ab123FR1, H8L15 and ustekinumab all can competitively block the binding of IL-12 to IL-12Rβ1 on the cell membrane surface of 293T-IL-12Rβ1&IL-23R, and the binding $EC_{50}$ values of Ab123FR1, H8L15 and ustekinumab are 1.99 μg/mL, 1.46 μg/mL and 1.58 μg/mL, respectively.

The above results show that the competitive binding activity of H8L15 for competitively blocking the binding of IL-12 to IL-12Rβ1 on the cell membrane surface is better than that of Ab123FR1 and ustekinumab.

TABLE 6

Results of antibodies H5L9, H5L10, H5L11, H5L12, H5L14 and ustekinumab competitively blocking the binding of human IL-12 to 293T-IL-12Rβ1&IL-23R cells detected by FACS

| Concentration (μg/mL)/MFI | 30 | 10 | 3.33 | 1.11 | 0.37 | 0.12 | 0.04 | 0.01 | $EC_{50}$ (μg/mL) |
|---|---|---|---|---|---|---|---|---|---|
| H5L9 | 117 | 134 | 146 | 157 | 159 | 160 | 158 | 169 | \ |
| H5L10 | 31.6 | 34.1 | 40.2 | 44.6 | 87.5 | 151 | 154 | 163 | 0.3312 |
| H5L11 | 33 | 33.9 | 42.2 | 54.3 | 103 | 145 | 151 | 166 | 0.414 |
| H5L12 | 31.8 | 32.4 | 31.8 | 38.5 | 86.6 | 133 | 149 | 161 | 0.3172 |
| H5L14 | 34.9 | 46.3 | 51.9 | 66 | 113 | 146 | 155 | 149 | 0.5320 |
| Ustekinumab | 28.7 | 31 | 29.7 | 31.9 | 95.7 | 137 | 150 | 160 | 0.3770 |

TABLE 7

Results of antibodies Ab123FR1, H8L15 and ustekinumab competitively
blocking the binding of IL-12 to 293T-IL-12Rβ1&IL-23R cells detected by FACS

| Concentrationx (μg/mL)/MFI | 30 | 10 | 3.33 | 1.11 | 0.37 | 0.12 | 0.04 | 0.01 | EC$_{50}$ (μg/mL) |
|---|---|---|---|---|---|---|---|---|---|
| H8L15 | 34.92 | 46.83 | 57.84 | 90.8 | 118.86 | 127.45 | 136.89 | 117.45 | 1.46 |
| Ab123FR1 | 36.29 | 47.78 | 54.84 | 105.2 | 115.6 | 108.16 | 123.57 | 118.88 | 1.99 |
| Ustekinumab | 40.32 | 40.9 | 46.98 | 99.64 | 120.43 | 123.28 | 114.93 | 114.66 | 1.58 |

2.1. Detection of Antibodies H5L9, H5L10, H5L11, H5L12, H5L14 and Ustekinumab Competitively Blocking the Binding of Human IL-23 to 293T-IL-12Rβ1&IL-23R Cells by Flow Cytometry 293T-IL-12Rβ1&IL-23R cells were digested in a conventional way and divided into several samples with 300,000 cells for each. 200 μL of 1% PBSA was added into each sample, and the mixture was centrifuged at 700×g for 5 min to discard the supernatant. According to experiment design, correspondingly diluted antibody (highest final concentration of 30 μg/mL, 3-fold dilution, 8 concentrations in total)

brane surface of 293T-IL-12Rβ1&IL-23R, the antibodies were ranked as follows from strong to weak: H5L10, H5L12, H5L11, H5L14, ustekinumab and H5L9.

The above results show that the competitive binding activity of H5L10, H5L12, H5L11 and H5L14 for competitively blocking the binding of IL-23 to IL-23 receptor complex on the cell membrane surface of 293T-IL-12Rβ1&IL-23R is better than that of ustekinumab.

TABLE 8

Results of antibodies H5L9, H5L10, H5L11, H5L12, H5L14 and ustekinumab competitively
blocking the binding of human IL-23 to 293T-IL-12Rβ1&IL-23R cells detected by FACS

| Concentration (μg/mL)/MFI | 30 | 10 | 3.33 | 1.11 | 0.37 | 0.12 | 0.04 | 0.01 | EC$_{50}$ (μg/mL) |
|---|---|---|---|---|---|---|---|---|---|
| H5L9 | 104 | 136 | 153 | 184 | 206 | 217 | 221 | 222 | 4.252 |
| H5L10 | 11.9 | 12.7 | 15.7 | 81.6 | 169 | 221 | 230 | 223 | 0.6995 |
| H5L11 | 12.9 | 14.5 | 20.2 | 97.6 | 179 | 219 | 224 | 219 | 0.8643 |
| H5L12 | 12.3 | 12.7 | 15.8 | 88.5 | 177 | 211 | 234 | 221 | 0.7748 |
| H5L14 | 14.1 | 16.7 | 23.6 | 95.6 | 179 | 203 | 216 | 218 | 0.8806 |
| Ustekinumab | 9.64 | 11.5 | 13.8 | 121 | 186 | 211 | 216 | 219 | 1.158 | and human IL-23 (IL-23-His-Biotin, Akesobio, 20161209) (final concentration of 2 μg/mL) were mixed at a ratio of 1:1, and a blank control was set. The mixture of antibody and human IL23 was incubated on ice for 30 min and then added to the cell precipitate at 100 μL/sample. The resulting mixture was well mixed and incubated on ice for 60 min. 200 μL of 1% PBSA was added, and the mixture was centrifuged at 700×g for 5 min to discard the supernatant, and then washed twice. FITC Steptavidin (Biolegend, Cat. No.: 405202) was diluted at a ratio of 1:500 and added to each tube at 100 μL. The mixture was well mixed and incubated on ice for 40 min in the absence of light. 200 μL of 1% PBSA was added, and the mixture was centrifuged at 700×g for 5 min to discard the supernatant, and then washed twice. 1% PBSA was added at 200 μL/tube, and the cells were resuspended and transferred to a flow cytometry tube for testing. The results of antibodies H5L9, H5L10, H5L11, H5L12, H5L14 and ustekinumab competitively blocking the binding of human IL-23 to 293T-IL-12Rβ1&IL-23R cells detected by FACS are shown in Table 8 and FIG. 14.

Figure 14:
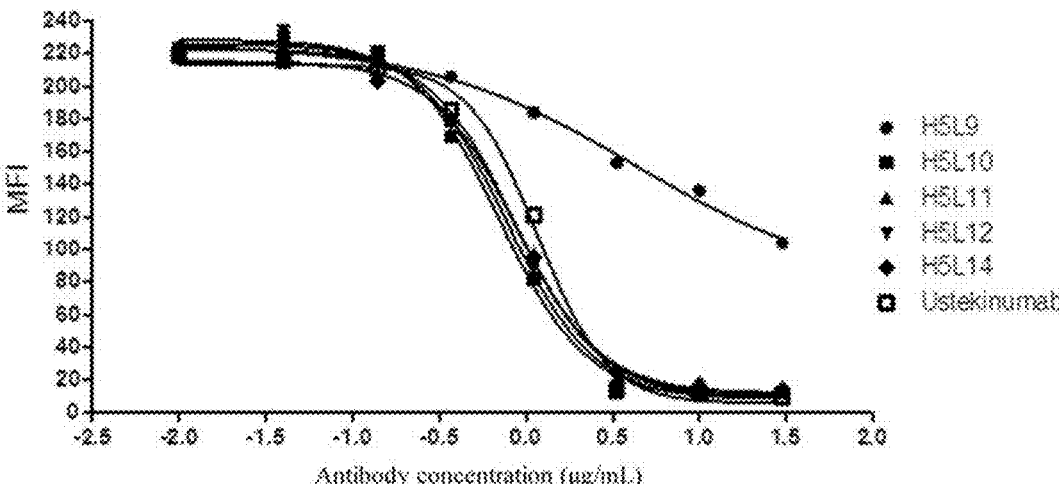
FIG. 14: antibodies H5L9, H5L10, H5L11, H5L12, H5L14 and ustekinumab competitively blocking the binding of human IL-23 to 293T-IL-12Rβ1&IL-23R cells (FACS).

According to the results shown in Table 8 and FIG. 14, H5L9, H5L10, H5L11, H5L12, H5L14 and ustekinumab all can competitively block the binding of IL-23 to IL-23 receptor complex on the cell membrane surface of 293T-IL-12Rβ1&IL-23R, and the competitive binding EC$_{50}$ values of these antibodies are 4.252 μg/mL, 0.6995 μg/mL, 0.8643 μg/mL, 0.7748 μg/mL, 0.8806 μg/mL and 1.158 μg/mL, respectively.

In terms of strength for competitively blocking the binding of IL-23 to IL-23 receptor complex on the cell mem- 2.2. Detection of Antibodies Ab123FR1, H8L15 and Ustekinumab Competitively Blocking the Binding of Human IL-23 to 293T-IL-12Rβ1&IL-23R Cells by Flow Cytometry 293T-IL-12Rβ1&IL-23R cells were digested in a conventional way and divided into several samples with 300,000 cells for each. 200 μL of 1% PBSA was added into each sample, and the mixture was centrifuged at 1200 rpm for 5 min to discard the supernatant. According to experiment design, correspondingly diluted antibody (highest concentration of 60 μg/mL, 3-fold dilution, 8 concentrations in total) and human IL23-His-Biotin (Akeso Biopharma, Inc., Lot. No.: 20161209) (4 μg/mL) were mixed at a ratio of 1:1, and a blank control was set. The mixture of antibody and IL23-His-Biotin was incubated on ice for 30 min and then added to the cell precipitate at 100 μL/sample. The resulting mixture was well mixed and incubated on ice for 60 min. 200 μL of 1% PBSA was added, and the mixture was centrifuged at 1200 rpm for 5 min to discard the supernatant, and then washed twice. FITC Steptavidin (Biolegend, Cat. No.: 405202) was diluted at a ratio of 1:500 and added to each tube at 100 μL. The mixture was well mixed and incubated on ice for 40 min in the absence of light. 200 μL of 1% PBSA was added, and the mixture was centrifuged at 1200 rpm for 5 min to discard the supernatant, and then washed twice. 1% PBSA was added at 200 μL/tube, and the cells were resuspended and transferred to a flow cytometry tube for testing. The results of antibodies Ab123FR1, H8L15 and ustekinumab competitively blocking the binding of human IL-23 to 293T-IL-12Rβ1&IL-23R cells detected by FACS are shown in Table 9 and FIG. 21.

Figure 21:
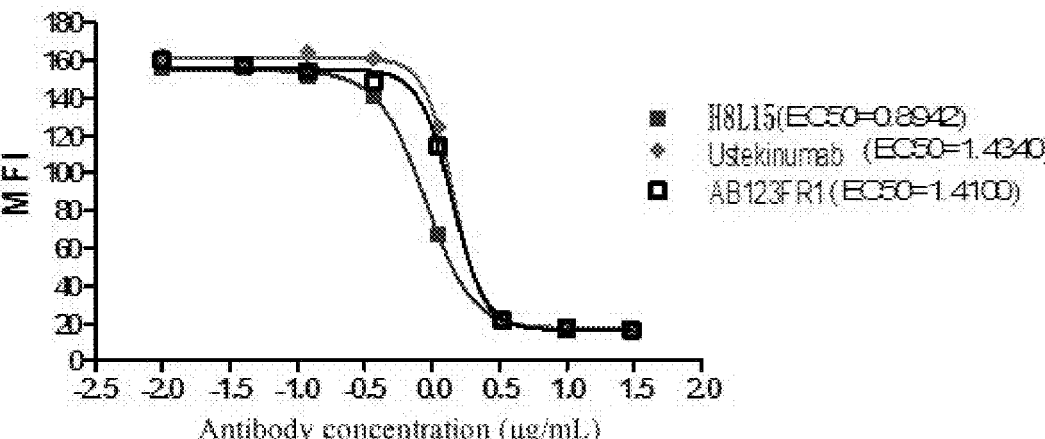
FIG. 21: antibodies Ab123FR1, H8L15 and ustekinumab competitively blocking the binding of human IL-23 to 293T-IL-12Rβ1&IL-23R cells (FACS).

According to the results shown in Table 9 and FIG. 21, Ab123FR1, H8L15 and ustekinumab all can competitively block the binding of IL-23 to IL-23R on the cell membrane surface of 293T-IL-12Rβ1&IL-23R. The binding $EC_{50}$ values of Ab123FR1, H8L15 and ustekinumab are 1.41 μg/mL, 0.8942 μg/mL and 1.434 μg/mL, respectively.

The above results show that the competitive binding activity of H8L15 for competitively blocking the binding of IL-23 to IL-23R on the cell membrane surface of 293T-IL-12Rβ1&IL-23R is better than that of Ab123FR1 and ustekinumab.

TABLE 9

Results of antibodies Ab123FR1, H8L15 and ustekinumab competitively blocking the binding of IL-23 to 293T-IL-12Rβ1&IL-23R cells detected by FACS

| Concentration (μg/mL)/MFI | 30 | 10 | 3.33 | 1.11 | 0.37 | 0.12 | 0.04 | 0.01 | $EC_{50}$ (μg/mL) |
|---|---|---|---|---|---|---|---|---|---|
| H8L15 | 15.67 | 17.95 | 20.65 | 67.47 | 140.58 | 151.42 | 155.60 | 155.36 | 0.8942 |
| Ab123FR1 | 16.62 | 17.43 | 21.52 | 114.17 | 148.32 | 154.10 | 157.47 | 159.75 | 1.41 |
| Ustekinumab | 17.65 | 18.37 | 22.39 | 124.07 | 160.96 | 164.00 | 156.17 | 162.10 | 1.434 |

Example 5. H8L15 Effectively Inhibiting IL-17A Secretion by Spleen Cells of Mice with Spontaneous Systemic Lupus Erythematosus Spontaneous systemic lupus erythematosus model (Jeltsch-David H. Autoimmun Rev. 2014; 13(9):963-973.) mice (MRL/lpr mice, purchased from Shanghai SLAC Laboratory Animal Co., Ltd.) were anesthetized with chloral hydrate, soaked in 75% ethyl alcohol for disinfection, transferred to a biosafety cabinet, and then dissected to take the spleen. The spleen was rinsed in a dish containing 1640 complete medium to remove fat and fascia tissue. The washed mouse spleen was placed in a 70 μm cell strainer and gently ground with a syringe plunger, and the spleen cell suspension was repeatedly washed with the culture solution. The filtrate was collected and centrifuged at 170×g for 5 minutes to discard the supernatant. 7 mL of erythrocyte lysate was added to resuspend the cell precipitate. The mixture was well mixed gently and left to stand on ice for 8 min, and then an equal volume of complete medium was added to stop lysis. The mixture was centrifuged at 170×g for 5 min to discard the supernatant. The cell precipitate was subjected to centrifugation and washing with 1640 complete medium twice, and then the cell precipitate was resuspended in 1640 complete medium, counted, adjusted for cell density, and seeded in a 96-well plate (1×10⁶/100 μL). According to experiment design, 50 μL of antibody was preincubated with 50 μL of IL-23 (final concentration of 20 ng/mL) for 1 h, and then 50 μL of IL-2 (final concentration of 100 U/mL) was added, and the mixture was incubated in an incubator at 37° C./5% $CO_2$ for 6 days. Six days later, cell supernatant was collected by centrifugation, and IL-17A concentration in the supernatant was detected by ELISA.

Figure 15:
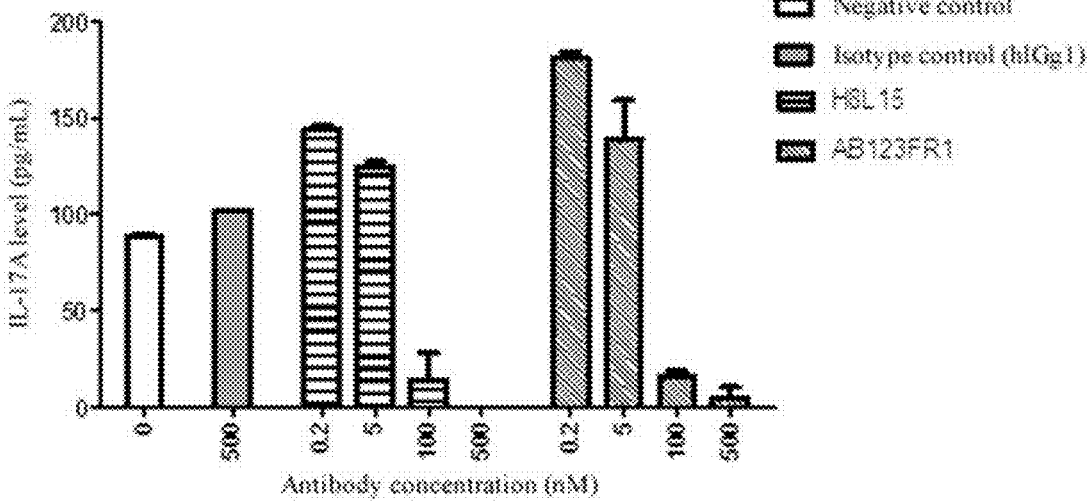
FIG. 15: H8L15 significantly inhibiting IL-23-induced IL-17A secretion by spleen cells of mice with spontaneous systemic lupus erythematosus.

As shown in FIG. 15, IL-23 is effective in promoting the IL-17A secretion by spleen cells of spontaneous systemic lupus erythematosus model mice. The addition of H8L15 while the IL-23 works significantly inhibits the IL-17A secretion, and the inhibitory activity is significantly dose-dependent, and the pharmacodynamic activity is remarkably superior to that of AB123FR1 (sometimes also referred to as Ab123FR1).

Example 6. H8L5 Effectively Ameliorating Skin Injury of Psoriasis Model Mice

After shaving, C57BL/6 mice (purchased from Guangdong Medical Laboratory Animal Center) were randomly divided into a normal group, a model group, a positive control group and H8L15 groups at 10 mice per group. One day prior to the first injection of recombinant human IL-23, the isotype control antibody (i.e., human anti-hen egg lysosome) was injected subcutaneously in the model group, the H8L15 dose groups were injected with H8L15 at corresponding concentrations, and the normal group was injected subcutaneously with an equal volume of normal saline. On day 1 after administration, 3.5% chloral hydrate was intraperitoneally injected at a dose of 7.5 ml/kg to anesthetize C57BL/6 mice, mice in normal group were intradermally injected with normal saline at 25 μL/mouse, and the remaining mice were intradermally injected with recombinant human IL-23 at 10 μg/25 μL/mouse. The injection was performed once daily for 6 consecutive days. On day 2 after the final intradermal injection of recombinant human IL-23, mice in each group were subjected to cervical dislocation, and small pieces of neck skin (about 0.5 cm×0.5 cm) were cut and fixed in formalin tissue fixative. Pathological sections of mouse skin were made 24 h later for 6 mice per group. After the pathological sections were made, 1 representative field of view was selected under a 100× microscope, and 6 sites in an original picture are randomly selected to measure the thickness of the skin epidermis of the mouse. Data were expressed as mean±standard error, and results were evaluated by one-way analysis of variance after the inter-group comparison processed by GraphPad software. P<0.05 suggests significant difference, and P<0.01 suggests very significant difference.

Figure 16:
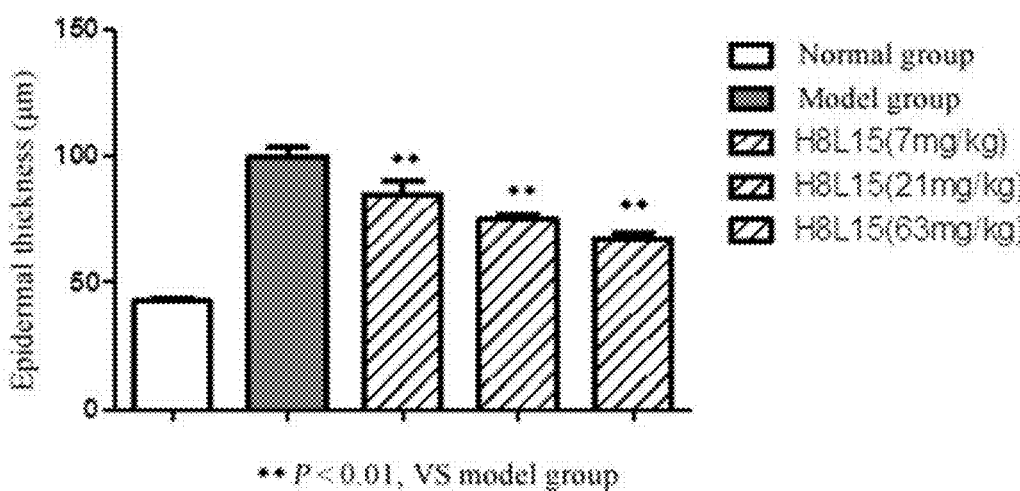
FIG. 16: H8L15 significantly ameliorating skin injury of psoriasis model mice.

The results are shown in FIG. 16. Compared with the normal group, the thickness of the skin epidermis of the mice in the model group is obviously increased (P<0.01). After administration, H8L15 is effective in inhibiting epidermal thickening in psoriasis mice (P<0.01).

Example 7. Treatment of Colitis with Anti-IL-12/IL-23 p40 Antibodies

Anti-IL-12/IL-23 p40 antibodies such as H8L15 were found to be effective in alleviating pathological changes and clinical symptoms in ulcerative colitis model mice.

A colitis model was established by inducing C57BL/6 mice with DSS (dextran sulfate sodium). The experimental mice were divided into groups with 3 mice in normal group and 6 mice in each of other groups. A positive control group (DSS group), an isotype control antibody group (anti-HEL), a high-dose H8L15 group (120 mg/kg) and a low-dose H8L15 group (40 mg/kg) were set. The drugs were administered by subcutaneous injection on D0, D3 and D6. In the normal group, the animal models were established by feeding sterile water through drinking bottles; in the DSS (MP Bio, Cat. No.: Q1723) group, the animal models were established by feeding 1% DSS solution (prepared by adding 2.5 g of DSS to 250 mL of sterile water) through drinking bottles for 9 consecutive days; in the experimental group with antibody, the animal models were established by feeding 1% DSS solution (prepared by adding 2.5 g of DSS to 250 mL of sterile water) through drinking bottles and intraperitoneally injecting hIL-23 recombinant protein (200 µL/100 µg/mouse) daily (D1-D5, D7-D9).

The use and welfare of the laboratory animals were carried out in compliance with the provisions of Association for Assessment and Accreditation of Laboratory Animal Care, International (AAALAC). The health and death of the animals are monitored daily, and routine examinations include observation of the effects of the test substance or drug on the daily performance of the animals, such as behavioral activities, weight changes and appearance.

The experimental index was to study the influence of the drug on colitis, and the specific index was based on the table of pathological scores of mouse colitis, which is shown in Table 10.

TABLE 10

Pathological scores of mouse colitis

| Pathological tissue condition of colon lesion | Score |
|---|---|
| Inflammatory infiltration: | 0—none 1—relatively mild 2—mild 3—moderate 4—relatively severe 5—severe |
| Crypt damage: | 0—none 1—mild 2—moderate 3—severe |
| Ulcer: | 0—none 1—mild 2—moderate 3—severe |
| Edema: | 0—no 1—yes |

TABLE 11

Administration dosage and scheme

| Group | n | Animal model | Administration |
|---|---|---|---|
| Normal group | 3 | Feeding sterile water through drinking bottle | |
| DSS group | 6 | 1% DSS solution was prepared by adding 2.5 g of DSS to 250 mL of sterile water and fed to the mice through drinking bottles for 9 consecutive days (D1-D9), and the experiment was terminated on day 10 | |
| DSS + hIL-23 + hIgG1 120 mg/kg | 6 | 1% DSS solution was prepared by adding 2.5 g of DSS to 250 mL of sterile water and fed to the mice through drinking bottles, hIL-23 recombinant protein (200 µL/100 µg/mouse) were intraperitoneally injected daily (D1-D6, D8-D9), and the experiment was terminated on day 10 | hIgG1, 120 mg/kg, SC, D0, D3, D6 |
| DSS + hIL-23 + H8L15 120 mg/kg | 6 | | H8L15, 120mg/kg, SC, D0, D3, D6 |
| DSS + hIL-23 + H8L15 40 mg/kg | 6 | | H8L15, 40mg/kg, SC, D0, D3, D6 |

*Randomly grouped; the time of first administration was $D_0$; SC: subcutaneous injection.

Figure 17:
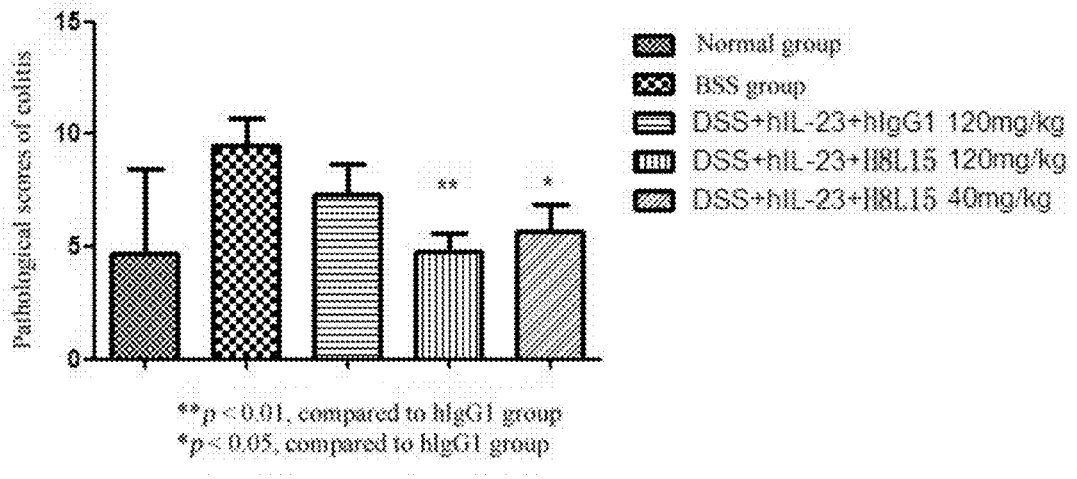
FIG. 17: statistical results of pathological scores for ulcerative colitis in each experimental group; H8L15 significantly alleviates pathological changes and clinical symptoms of ulcerative colitis model mice.
Figure 19:
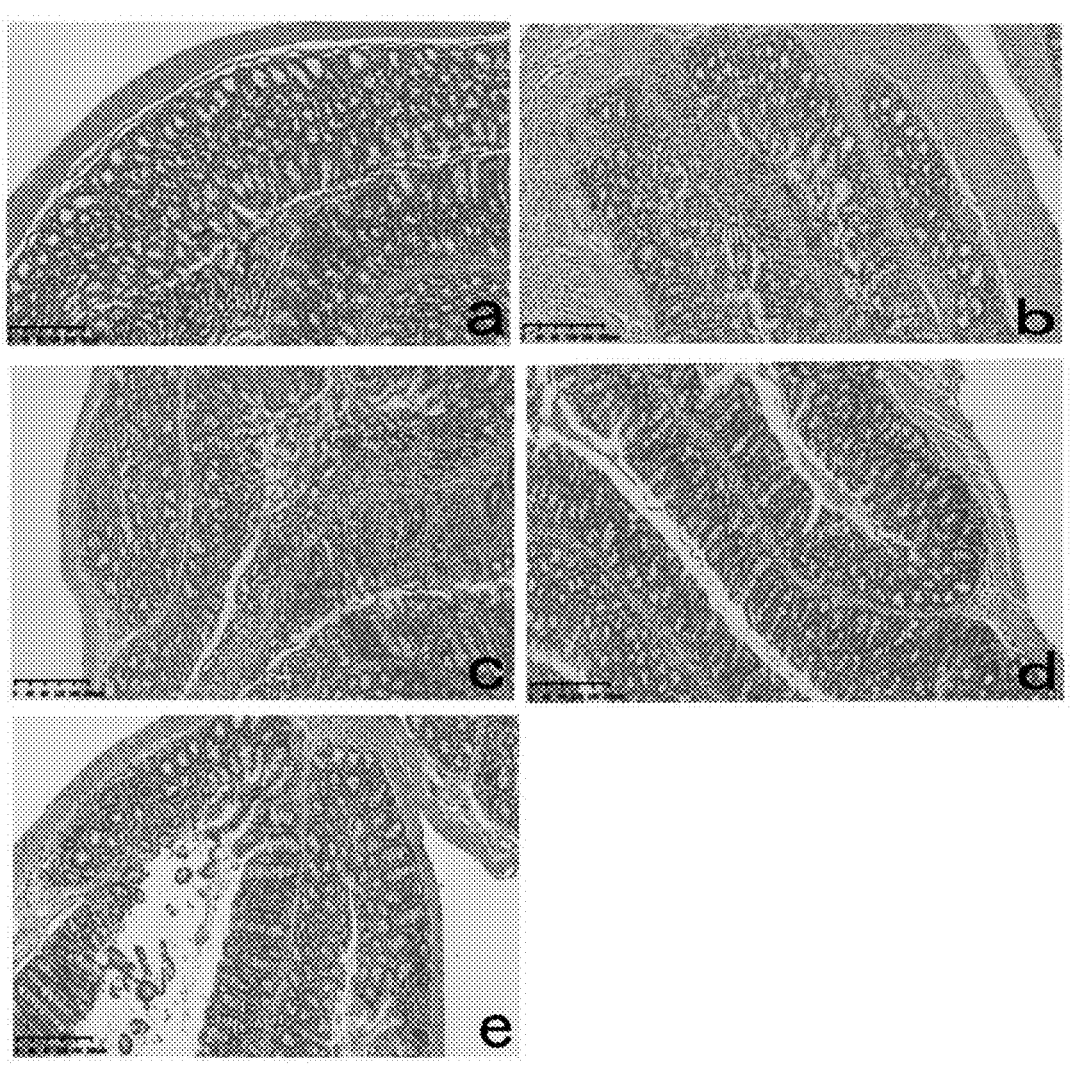
FIG. 19: demonstration of the skin histopathological observation for the H8L15 treatment of colitis mouse induced by DSS in combination with recombinant human IL-23.

For the experimental results, Table 10 is the pathological scoring standard of mouse colitis, Table 11 is the establishment method of mouse models and the administration scheme of antibody in each experimental group, and the pathological scoring results of colitis are shown in FIG. 17. The demonstration of the skin histopathological observation for the H8L15 treatment of colitis mouse induced by DSS in combination with recombinant human IL-23 (HE staining, ×100) (a: Normal group; b: DSS group; c: DSS+hIL-23+ hIgG1 (120 mg/kg) group; d: DSS+hIL-23+H8L15 (120 mg/kg) group; e: DSS+hIL-23+H8L15 (40 mg/kg) group) is shown in FIG. 19.

Figure 18:
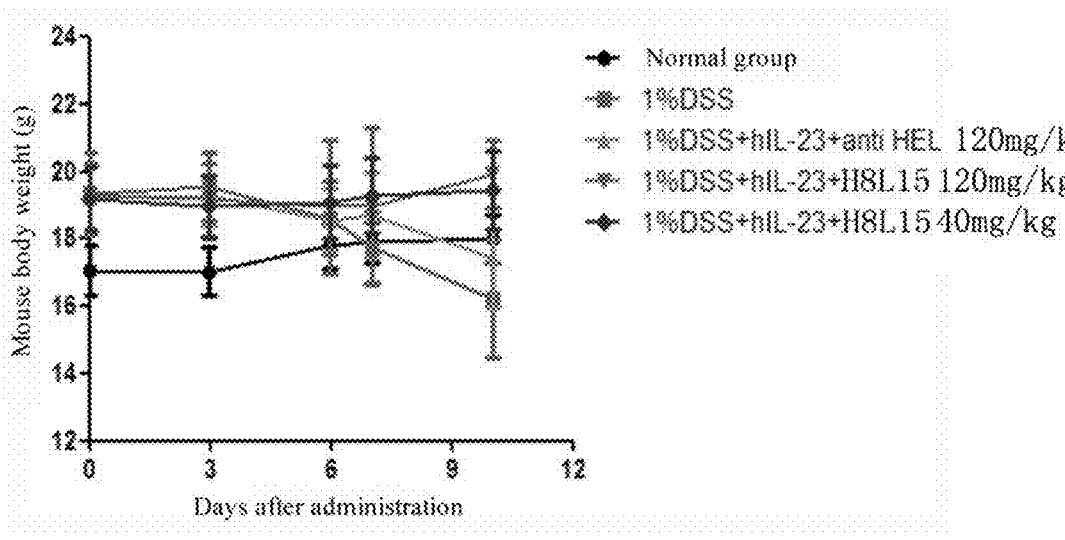
FIG. 18: change in body weight of experimental mice.

Conclusion: according to the body weight of mice in the experimental period shown in FIG. 18, the body weight of mice in model group constantly reduces, while the body weight of mice in treatment groups does not reduce, which is obviously different from that of the model group. According to pathological scores of colitis shown in FIG. 17, the model group shows obvious characteristics of colitis, while the high-dose and low-dose treatment groups show statistically significant differences from the model group, indicating that the antibody H8L15 is effective in treating ulcerative colitis.

The information about sequences is as follows:

The amino acid sequence of heavy chain variable region of H5L9, H5L10, H5L11, H5L12 and H5L14 is set forth in SEQ ID NO: 1

(SEQ ID NO: 1)
EVQLVQSGAEVKKPGESLKISCQSSGYSFTTYWIGWVRQMPGQGLEWIGI

MSPVDSDIRYNPMFRGQVTMSVDKSSSTAYLQWSSLKASDTAMYYCARRR

PGQGYFDFWGQGTMVTVSS

The nucleotide sequence of heavy chain variable region of H5L9, H5L10, H5L11, H5L12 and H5L14 is set forth in SEQ ID NO: 2

(SEQ ID NO: 2)
GAGGTGCAGCTGGTGCAGTCTGGGGCCGAAGTGAAGAAACCCGGGGAGAG

TCTGAAGATCTCATGCCAGAGCTCCGGCTACTCCTTCACCACATATTGGA

TCGGGTGGGTGAGACAGATGCCTGGCCAGGGGCTGGAATGGATCGGAATT

ATGAGCCCAGTGGACTCCGATATTCGCTACAACCCCATGTTTCGAGGCCA

GGTGACAATGAGCGTGGACAAGTCTAGTTCAACTGCTTATCTGCAGTGGA

GCTCCCTGAAAGCCAGCGATACCGCTATGTACTATTGTGCCCGGAGAAGG

CCTGGACAGGGCTACTTCGACTTTTGGGGGCAGGGAACTATGGTGACCGT

CTCTAGT

For H5L9, H5L10, H5L11, H5L12 and H5L14, HCDR1 is set forth in SEQ ID NO: 3, HCDR2 is set forth in SEQ ID NO: 4, and HCDR3 is set forth in SEQ ID NO: 5

(SEQ ID NO: 3)
HCDR1: GYSFTTYW (SEQ ID NO: 4)
HCDR2: MSPVDSDI (SEQ ID NO: 5)
HCDR3: ARRRPGQGYFDF

The amino acid sequence of light chain variable region of H5L9 is set forth in SEQ ID NO: 6
DIQMTQSPSSLSASVGDRVTITCKASQNVGSWLAWYQQKPGKAPKSLIYS

ASSRQSGVPSRFSGSGSGTDFTLTISSLQPEDFATYYCQQYDIYPFTFGQ

GTKLEIK

-continued

-continued

The nucleotide sequence of light chain variable
region of H5L9 is set forth in SEQ ID NO: 7
GATATTCAGATGACCCAGAGCCCTTCAAGCCTGTCCGCAAGCGTCGGGGA

TAGAGTGACCATTACCTGTAAAGCAAGCCAGAACGTGGGAAGCTGGCTGG

CCTGGTACCAGCAGAAGCCAGGCAAAGCACCCAAGTCTCTGATCTATAGT

GCAAGCTCCCGGCAGTCAGGAGTGCCAAGCAGATTCAGTGGCTCAGGGAG

CGGAACAGACTTTACCCTGACAATCTCTAGTCTGCAGCCTGAGGACTTCG

CAACTTACTATTGCCAGCAGTACGATATCTACCCATTCACATTTGGCCAG

GGGACTAAACTGGAGATCAAG

For H5L9, LCDR1 is set forth in SEQ ID NO: 8, LCDR2
is set forth in SEQ ID NO: 9, and LCDR3 is set forth in SEQ
ID NO: 10

(SEQ ID NO: 8)
LCDR1: QNVGSW (SEQ ID NO: 9)
LCDR2: ASS (SEQ ID NO: 10)
LCDR3: QQYDIYPFT
The amino acid sequence of light chain variable
region of H5L10 is set forth in SEQ ID NO: 11
EIVLTQSPATLSASPGERATISCRASQSVGSWLAWYQQKPGQAPRSLIYA

ASNLQSGIPARFSGSGSGTDFTLTISSLEPEDFAVYYCQQYNIYPYTFGQ

GTRLEIK

The nucleotide sequence of light chain variable
region of H5L10 is set forth in SEQ ID NO: 12
GAGATCGTCCTGACACAGAGTCCTGCTACCCTGAGCGCTTCCCCAGGAGA GAGGGCAACCATCTCCTGCCGCGCCTCTCAGaGCgTTGGCTCCTGGCTGG

CTTGGTACCAGCAGAAGCCAGGCCAGGCACCCCGAAGCCTGATCTATGCC

GCTTCTAaTCTGCAGAGCGGGATTCCCGCTAGATTCTCTGGCAGTGGGTC

AGGAACAGACTTTACCCTGACAATCTCAAGCCTGGAGCCTGAAGATTTCG

CCGTGTACTATTGCCAGCAGTACAACATCTACCCATATACATTTGGCCAG

GGGACTCGGCTGGAGATCAAG

The amino acid sequence of light chain variable
region of H5L11 is set forth in SEQ ID NO: 13
EIVLTQSPATLSASPGERATISCRASQSVSSWLAWYQQKPGQAPRSLIYS

ASNLQSGIPARFSGSGSGTDFTLTISSLEPEDFAVYYCQQYNIYPYTFGQ

GTRLEIK

The nucleotide sequence of light chain variable
region of H5L11 is set forth in SEQ ID NO: 14
GAGATCGTCCTGACACAGAGTCCTGCTACCCTGAGCGCTTCCCCAGGAGA GAGGGCAACCATCTCCTGCCGCGCCTCTCAGaGCgTTAGCTCCTGGCTGG

CTTGGTACCAGCAGAAGCCAGGCCAGGCACCCCGAAGCCTGATCTATTCC

GCTTCTAaTCTGCAGAGCGGGATTCCCGCTAGATTCTCTGGCAGTGGGTC

AGGAACAGACTTTACCCTGACAATCTCAAGCCTGGAGCCTGAAGATTTCG

CCGTGTACTATTGCCAGCAGTACAACATCTACCCATATACATTTGGCCAG

GGGACTCGGCTGGAGATCAAG

The amino acid sequence of light chain variable
region of H5L12 is set forth in SEQ ID NO: 15
EIVLTQSPATLSASPGERATISCRASQSVSSWLAWYQQKPGQAPRSLIYA

ASNRQSGIPARFSGSGSGTDFTLTISSLEPEDFAVYYCQQYNIYPYTFGQ

GTRLEIK

The nucleotide sequence of light chain variable
region of H5L12 is set forth in SEQ ID NO: 16
GAGATCGTCCTGACACAGAGTCCTGCTACCCTGAGCGCTTCCCCAGGAGA GAGGGCAACCATCTCCTGCCGCGCCTCTCAGaGCgTTAGCTCCTGGCTGG

CTTGGTACCAGCAGAAGCCAGGCCAGGCACCCCGAAGCCTGATCTATGCC

GCTTCTAaTCGGCAGAGCGGGATTCCCGCTAGATTCTCTGGCAGTGGGTC

AGGAACAGACTTTACCCTGACAATCTCAAGCCTGGAGCCTGAAGATTTCG

CCGTGTACTATTGCCAGCAGTACAACATCTACCCATATACATTTGGCCAG

GGGACTCGGCTGGAGATCAAG

The amino acid sequence of light chain variable
region of H5L14 is set forth in SEQ ID NO: 17
EIVLTQSPATLSASPGERATISCRASQSVSSWLAWYQQKPGQAPRSLIYA

ASNLQSGIPARFSGSGSGTDFTLTISSLEPEDFAVYYCQQYNIYPFTFGQ

GTRLEIK

The nucleotide sequence of light chain variable
region of H5L14 is set forth in SEQ ID NO: 18
GAGATCGTCCTGACACAGAGTCCTGCTACCCTGAGCGCTTCCCCAGGAGA GAGGGCAACCATCTCCTGCCGCGCCTCTCAGaGCgTTAGCTCCTGGCTGG

CTTGGTACCAGCAGAAGCCAGGCCAGGCACCCCGAAGCCTGATCTATGCC

GCTTCTAaTCTGCAGAGCGGGATTCCCGCTAGATTCTCTGGCAGTGGGTC

AGGAACAGACTTTACCCTGACAATCTCAAGCCTGGAGCCTGAAGATTTCG

CCGTGTACTATTGCCAGCAGTACAACATCTACCCATTTACATTTGGCCAG

GGGACTCGGCTGGAGATCAAG

LCDR1 of L10 is set forth in SEQ ID NO: 19
QSVGSW

LCDR1 of L11, L12 and L14 is set forth in
SEQ ID NO: 20
QSVSSW

LCDR2 of L10, L11, L12 and L14 is set forth in
SEQ ID NO: 21
ASN

LCDR3 of L10, L11 and L12 is set forth in
SEQ ID NO: 22
QQYNIYPYT

LCDR3 of L14 is set forth in SEQ ID NO: 23
QQYNIYPFT

The amino acid sequence of heavy chain variable
region of H8L15 is set forth in SEQ ID NO: 24
EVQLVQSGAEVKKPGESLKISCQSSGYTFTSYWIGWVRQMPGQGLEWIG

IMSPVDSDIRYNPMFRGQVTMSVDKSSSTAYLQWSSLKASDTAMYYCAR

RRPGQGYFDFWGQGTMVTVSS

-continued

The amino acid sequence of light chain variable
region of H8L15 is set forth in SEQ ID NO: 25
EIVLTQSPATLSASPGERATISCRASQSVGTWVAWYQQKPGQAPRSLIY

AASNLQSGIPARFSGSGSGTDFTLTISSLEPEDFAVYYCQQYNIYPYTF

GQGTRLEIK

For H8L15, HCDR1 is set forth in SEQ ID NO: 26,
HCDR2 is set forth in SEQ ID NO: 4, HCDR3 is set forth
in SEQ ID NO: 5, LCDR1 is set forth in SEQ ID NO: 27,
LCDR2 is set forth in SEQ ID NO: 28, LCDR3 is set forth
in SEQ ID NO: 22, FR-H1 is set forth in SEQ ID NO: 29,
FR-H2 is set forth in SEQ ID NO: 30, FR-H3 is set forth in
SEQ ID NO: 31, FR-H4 is set forth in SEQ ID NO: 32,
FR-L1 is set forth in SEQ ID NO: 33, FR-L2 is set forth in
SEQ ID NO: 34, FR-L3 is set forth in SEQ ID NO: 35, and
FR-L4 is set forth in SEQ ID NO: 36

```
                                    (SEQ ID NO: 26)
HCDR1: GYTFTSYW (SEQ ID NO: 4)
HCDR2: MSPVDSDI (SEQ ID NO: 5)
HCDR3: ARRRPGQGYFDF (SEQ ID NO: 27)
LCDR1: QSVGTW (SEQ ID NO: 28)
LCDR2: AAS (SEQ ID NO: 22)
LCDR3: QQYNIYPYT (SEQ ID NO: 29)
FR-H1: EVQLVQSGAEVKKPGESLKISCQSS (SEQ ID NO: 30)
FR-H2: IGWVRQMPGQGLEWIGI (SEQ ID NO: 31)
FR-H3: RYNPMFRGQVTMSVDKSSSTAYLQWSSLKASDTAMYYC (SEQ ID NO: 32)
FR-H4: WGQGTMVTVSS (SEQ ID NO: 33)
FR-L1: EIVLTQSPATLSASPGERATISCRAS (SEQ ID NO: 34)
FR-L2: VAWYQQKPGQAPRSLIY (SEQ ID NO: 35)
FR-L3: NLQSGIPARFSGSGSGTDFTLTISSLEPEDFAVYC (SEQ ID NO: 36)
FR-L4: FGQGTRLEIK
```

The nucleotide sequence of heavy chain variable
region of H8L15 is set forth in SEQ ID NO: 37
GAGGTGCAGCTGGTGCAGTCTGGGGCCGAAGTGAAGAAACCCGGGGAGAG

TCTGAAGATCTCATGCCAGAGCTCCGGCTACACCTTCACCTCATATTGGA

TCGGGTGGGTGAGACAGATGCCTGGCCAGGGGCTGGAATGGATCGGAATT

ATGAGCCCAGTGGACTCCGATATTCGCTACAACCCCATGTTTCGAGGCCA

GGTGACAATGAGCGTGGACAAGTCTAGTTCAACTGCTTATCTGCAGTGGA

GCTCCCTGAAAGCCAGCGATACCGCTATGTACTATTGTGCCCGGAGAAGG

-continued

CCTGGACAGGGCTACTTCGACTTTTGGGGGCAGGGAACTATGGTGACCGT

CTCTAGT

The nucleotide sequence of light chain variable
region of H8L15 is set forth in SEQ ID NO: 38
GAGATCGTCCTGACACAGAGTCCTGCTACCCTGAGCGCTTCCCCAGGAGA

GAGGGCAACCATCTCCTGCCGCGCCTCTCAGAGCGTTGGCACCTGGGTGG

CTTGGTACCAGCAGAAGCCAGGCCAGGCACCCCGAAGCCTGATCTATGCC

GCTTCTAATCTGCAGAGCGGGATTCCCGCTAGATTCTCTGGCAGTGGGTC

AGGAACAGACTTTACCCTGACAATCTCAAGCCTGGAGCCTGAAGATTTCG

CCGTGTACTATTGCCAGCAGTACAACATCTACCCATATACATTTGGCCAG

GGGACTCGGCTGGAGATCAAG

The heavy chain amino acid sequence of H8L15 is
set forth in SEQ ID NO: 39
EVQLVQSGAEVKKPGESLKISCQSSGYTFTSYWIGWVRQMPGQGLEWIGI

MSPVDSDIRYNPMFRGQVTMSVDKSSSTAYLQWSSLKASDTAMYYCARRR

PGQGYFDFWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

The light chain amino acid sequence of H8L15 is
set forth in SEQ ID NO: 40
EIVLTQSPATLSASPGERATISCRASQSVGTWVAWYQQKPGQAPRSLIYA

ASNLQSGIPARFSGSGSGTDFTLTISSLEPEDFAVYYCQQYNIYPYTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

For H5L9, the sequences of FR-H1, FR-H2, FR-H3 and
FR-H4 are the same as those of H8L15, the sequence of
FR-L1 is set forth in SEQ ID NO: 41, the sequence of FR-L2
is set forth in SEQ ID NO: 42, FR-L3 is set forth in SEQ ID
NO: 43, and FR-L4 is set forth in SEQ ID NO: 44

```
                                    (SEQ ID NO: 41)
FR-L1: DIQMTQSPSSLSASVGDRVTITCKAS (SEQ ID NO: 42)
FR-L2: LAWYQQKPGKAPKSLIYS (SEQ ID NO: 43)
FR-L3: RQSGVPSRFSGSGSGTDFTLTISSLQPEDFATYYC (SEQ ID NO: 44)
FR-L4: FGQGTKLEIK
```

For H5L10, the sequences of FR-H1, FR-H2, FR-H3 and
FR-H4 are the same as those of H8L15, the sequence of
FR-L1 is set forth in SEQ ID NO: 33, the sequence of FR-L2 is set forth in SEQ ID NO: 45, FR-L3 is set forth in SEQ ID NO: 46, and FR-L4 is set forth in SEQ ID NO: 36

```
                                            (SEQ ID NO: 33)
FR-L1: EIVLTQSPATLSASPGERATISCRAS (SEQ ID NO: 45)
FR-L2: LAWYQQKPGQAPRSLIYA (SEQ ID NO: 46)
FR-L3: LQSGIPARFSGSGSGTDFTLTISSLEPEDFAVYYC (SEQ ID NO: 36)
FR-L4: FGQGTRLEIK
```

For H5L11, the sequences of FR-H1, FR-H2, FR-H3 and FR-H4 are the same as those of H8L15, the sequence of FR-L1 is set forth in SEQ ID NO: 33, the sequence of FR-L2 is set forth in SEQ ID NO: 47, FR-L3 is set forth in SEQ ID NO: 46, and FR-L4 is set forth in SEQ ID NO: 36

```
                                            (SEQ ID NO: 33)
FR-L1: EIVLTQSPATLSASPGERATISCRAS (SEQ ID NO: 47)
FR-L2: LAWYQQKPGQAPRSLIYS (SEQ ID NO: 46)
FR-L3: LQSGIPARFSGSGSGTDFTLTISSLEPEDFAVYYC (SEQ ID NO: 36)
FR-L4: FGQGTRLEIK
```

For H5L12, the sequences of FR-H1, FR-H2, FR-H3 and FR-H4 are the same as those of H8L15, the sequence of FR-L1 is set forth in SEQ ID NO: 33, the sequence of FR-L2 is set forth in SEQ ID NO: 45, FR-L3 is set forth in SEQ ID NO: 48, and FR-L4 is set forth in SEQ ID NO: 36

```
                                            (SEQ ID NO: 33)
FR-L1: EIVLTQSPATLSASPGERATISCRAS (SEQ ID NO: 45)
FR-L2: LAWYQQKPGQAPRSLIYA (SEQ ID NO: 48)
FR-L3: RQSGIPARFSGSGSGTDFTLTISSLEPEDFAVYYC (SEQ ID NO: 36)
FR-L4: FGQGTRLEIK
```

For H5L14, the sequences of FR-H1, FR-H2, FR-H3 and FR-H4 are the same as those of H8L15, the sequence of FR-L1 is set forth in SEQ ID NO: 33, the sequence of FR-L2 is set forth in SEQ ID NO: 45, FR-L3 is set forth in SEQ ID NO: 46, and FR-L4 is set forth in SEQ ID NO: 36

```
                                            (SEQ ID NO: 33)
FR-L1: EIVLTQSPATLSASPGERATISCRAS (SEQ ID NO: 45)
FR-L2: LAWYQQKPGQAPRSLIYA (SEQ ID NO: 46)
FR-L3: LQSGIPARFSGSGSGTDFTLTISSLEPEDFAVYYC (SEQ ID NO: 36)
FR-L4: FGQGTRLEIK
```

-continued

```
The heavy chain amino acid sequence of H5L9,
H5L10, H5L11, H5L12 and H5L14 is set forth in
SEQ ID NO: 49
EVQLVQSGAEVKKPGESLKISCQSSGYSFTTYWIGWVRQMPGQGLEWIGI

MSPVDSDIRYNPMFRGQVTMSVDKSSSTAYLQWSSLKASDTAMYYCARRR

PGQGYFDFWGQGTMVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

The light chain amino acid sequence of H5L9 is set
forth in SEQ ID NO: 50
DIQMTQSPSSLSASVGDRVTITCKASQNVGSWLAWYQQKPGKAPKSLIYS

ASSRQSGVPSRFSGSGSGTDFTLTISSLQPEDFATYYCQQYDIYPFTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The light chain amino acid sequence of H5L10 is
set forth in SEQ ID NO: 51
EIVLTQSPATLSASPGERATISCRASQSVGSWLAWYQQKPGQAPRSLIYA

ASNLQSGIPARFSGSGSGTDFTLTISSLEPEDFAVYYCQQYNIYPYTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The light chain amino acid sequence of H5L11 is
set forth in SEQ ID NO: 52
EIVLTQSPATLSASPGERATISCRASQSVSSWLAWYQQKPGQAPRSLIYS

ASNLQSGIPARFSGSGSGTDFTLTISSLEPEDFAVYYCQQYNIYPYTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The light chain amino acid sequence of H5L12 is
set forth in SEQ ID NO: 53
EIVLTQSPATLSASPGERATISCRASQSVSSWLAWYQQKPGQAPRSLIYA

ASNRQSGIPARFSGSGSGTDFTLTISSLEPEDFAVYYCQQYNIYPYTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The light chain amino acid sequence of H5L14 is
set forth in SEQ ID NO: 54
EIVLTQSPATLSASPGERATISCRASQSVSSWLAWYQQKPGQAPRSLIYA

ASNLQSGIPARFSGSGSGTDFTLTISSLEPEDFAVYYCQQYNIYPFTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

The invention claimed is:

1. An antibody or an antigen-binding fragment thereof, wherein the antibody comprises:

(1) a heavy chain variable region comprising or consisting of:

an amino acid sequence set forth in SEQ ID NO: 1, or a sequence having at least 80% sequence identity to the sequence set forth in SEQ ID NO: 1, and comprising HCDR1 of SEQ ID NO:3, HCDR2 of SEQ ID NO:4 and HCDR3 of SEQ ID NO:5, and a light chain variable region comprising or consisting of:

an amino acid sequence set forth in SEQ ID NO: 6, or a sequence having at least 80% sequence identity to the sequence set forth in SEQ ID NO: 6 and comprising LCDR1 of SEQ ID NO:8, LCDR2 of SEQ ID NO:9 and LCDR3 of SEQ ID NO:10, (2) a heavy chain variable region comprising or consisting of:

an amino acid sequence set forth in SEQ ID NO: 1, or a sequence having at least 80% sequence identity to the sequence set forth in SEQ ID NO: 1 and comprising HCDR1 of SEQ ID NO:3, HCDR2 of SEQ ID NO:4 and HCDR3 of SEQ ID NO:5; and a light chain variable region comprising or consisting of:

an amino acid sequence set forth in SEQ ID NO: 11, or a sequence having at least 80% sequence identity to the sequence set forth in SEQ ID NO: 11 and comprising LCDR1 of SEQ ID NO:19, LCDR2 of SEQ ID NO:21 and LCDR3 of SEQ ID NO:22, (3) a heavy chain variable region comprising or consisting of:

an amino acid sequence set forth in SEQ ID NO: 1, or a sequence having at least 80% sequence identity to the sequence set forth in SEQ ID NO: 1 and comprising HCDR1 of SEQ ID NO:3, HCDR2 of SEQ ID NO:4 and HCDR3 of SEQ ID NO:5; and a light chain variable region comprising or consisting of:

an amino acid sequence set forth in SEQ ID NO: 15, or a sequence having at least 80% sequence identity to the sequence set forth in SEQ ID NO: 15 and comprising LCDR1 of SEQ ID NO:20, LCDR2 of SEQ ID NO:21 and LCDR3 of SEQ ID NO:22, (4) a heavy chain variable region comprising or consisting of:

an amino acid sequence set forth in SEQ ID NO: 1, or a sequence having at least 80% sequence identity to the sequence set forth in SEQ ID NO: 1 and comprising HCDR1 of SEQ ID NO:3, HCDR2 of SEQ ID NO:4 and HCDR3 of SEQ ID NO:5; and a light chain variable region comprising or consisting of:

an amino acid sequence set forth in SEQ ID NO: 17, or a sequence having at least 80% sequence identity to the sequence set forth in SEQ ID NO: 17 and comprising LCDR1 of SEQ ID NO:20, LCDR2 of SEQ ID NO:21 and LCDR3 of SEQ ID NO:23, or (5) a heavy chain variable region comprising or consisting of:

an amino acid sequence set forth in SEQ ID NO: 24, or a sequence having at least 80% sequence identity to the sequence set forth in SEQ ID NO: 24 and comprising HCDR1 of SEQ ID NO:26, HCDR2 of SEQ ID NO:4 and HCDR3 of SEQ ID NO:5; and a light chain variable region comprising or consisting of:

an amino acid sequence set forth in SEQ ID NO: 25, or a sequence having at least 80% sequence identity to the sequence set forth in SEQ ID NO: 25 and comprising LCDR1 of SEQ ID NO:27, LCDR2 of SEQ ID NO:28 and LCDR3 of SEQ ID NO:22, wherein the antigen-binding fragment is selected from the group consisting of: Fab, Fab', F(ab')₂, Fv, Fab/c, single chain antibody, and bivalent antibody.

2. An isolated polynucleotide encoding the antibody or the antigen-binding fragment thereof according to claim 1.

3. The polynucleotide according to claim 2, wherein the polynucleotide is contained in a vector, or a host cell.

4. The polynucleotide according to claim 2, which is used to prepare a polypeptide by culturing a host cell comprising the polynucleotide according to claim 2 in a suitable condition, and isolating the polypeptide from the cell cultures.

5. The antibody or the antigen-binding fragment thereof according to claim 1, wherein the antibody or the antigen-binding fragment thereof according to claim 1 is contained in an antibody conjugate, wherein the antibody or the antigen-binding fragment thereof is coupled to a conjugated moiety, wherein the conjugated moiety is a purification tag, optionally, a His tag, a cytotoxic agent or a detectable label.

6. The antibody or the antigen-binding fragment thereof according to claim 1 wherein the antibody or the antigen-binding fragment thereof is contained in a fusion protein, a multispecific antibody, a kit, or a pharmaceutical composition.

7. An in vivo or in vitro method, comprising administering to a cell or a subject the antibody or the antigen-binding fragment thereof according to claim 1, wherein the method is selected from the group consisting of:
a method for blocking the binding of human IL-12/IL-23 p40 protein domain to ligand IL-12Rβ1 or IL-23R,
a method for down-regulating the activity or the level of human IL-12/IL-23 p40 protein domain, and
a method for blocking cellular response mediated by the binding of human IL-12Rβ1 or human IL-23R to p40 protein domain.

8. A method for the prevention, treatment, adjuvant treatment and/or diagnosis of autoimmune diseases or ulcerative colitis, comprising administering to a subject in need the antibody or the antigen-binding fragment thereof according to claim 1.

9. The antibody or an antigen-binding fragment thereof according to claim 1, wherein the antibody comprises:
(1) a heavy chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 1 and comprising HCDR1 of SEQ ID NO:3, HCDR2 of SEQ ID NO:4 and HCDR3 of SEQ ID NO:5, and
a light chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 6 and comprising LCDR1 of SEQ ID NO:8, LCDR2 of SEQ ID NO:9 and LCDR3 of SEQ ID NO:10,
(2) a heavy chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 1 and comprising HCDR1 of SEQ ID NO:3, HCDR2 of SEQ ID NO:4 and HCDR3 of SEQ ID NO:5; and
a light chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 11 and comprising LCDR1 of SEQ ID NO:19, LCDR2 of SEQ ID NO:21 and LCDR3 of SEQ ID NO:22, (3) a heavy chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 1 and comprising HCDR1 of SEQ ID NO:3, HCDR2 of SEQ ID NO:4 and HCDR3 of SEQ ID NO:5; and
a light chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 15 and comprising LCDR1 of SEQ ID NO:20, LCDR2 of SEQ ID NO:21 and LCDR3 of SEQ ID NO:22,
(4) a heavy chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO: 1 and comprising HCDR1 of SEQ ID NO:3, HCDR2 of SEQ ID NO:4 and HCDR3 of SEQ ID NO:5; and
a light chain variable region comprising or consisting of:
a sequence having 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:17 and comprising LCDR1 of SEQ ID NO:20, LCDR2 of SEQ ID NO:21 and LCDR3 of SEQ ID NO:23, or
(5) a heavy chain variable region comprising or consisting of:
a sequence having 81%, 82%, 83%, 84%, 85%, 86%, 87%, 88%, 89% or 90%, 91%, 92%, 93%, 94%, 95%, 96%, 97%, 98% or 99% sequence identity to the sequence set forth in SEQ ID NO:24 and comprising HCDR1 of SEQ ID NO:26, HCDR2 of SEQ ID NO:4 and HCDR3 of SEQ ID NO:5; and
a light chain variable region comprising or consisting of:
a sequence having 81%, 82%, 83%, 84%, 85%, 86%, 87%, 88%, 89% or 90%, 91%, 92%, 93%, 94%, 95%, 96%, 97%, 98% or 99% sequence identity to the sequence set forth in SEQ ID NO: 25 and comprising LCDR1 of SEQ ID NO:27, LCDR2 of SEQ ID NO:28 and LCDR3 of SEQ ID NO:22.

10. An antibody or an antigen-binding fragment thereof, wherein the antibody comprises or consists of a heavy chain set forth in SEQ ID NO: 49 and a light chain set forth in SEQ ID NO: 50.

11. The antibody or an antigen-binding fragment thereof according to claim 1, wherein the antibody further comprises a heavy chain constant region and a light chain constant region, and the constant regions are derived from a human IgG.

12. The antibody or an antigen-binding fragment thereof according to claim 1, wherein the heavy chain constant region is an Ig gamma-1 chain C region; the light chain constant region is an Ig kappa chain C region.

13. The antibody or an antigen-binding fragment thereof according to claim 1, wherein the antibody is a humanized antibody, a chimeric antibody or a multispecific antibody, optionally, a bispecific antibody.

14. The antibody or an antigen-binding fragment thereof according to claim 5, wherein the conjugated moiety is a radioisotope, a luminescent substance, a colored substance, an enzyme or polyethylene glycol.

15. The antibody or the antigen-binding fragment thereof according to claim 6, wherein the kit further comprises a second antibody specifically identifying the antibody or the antigen-binding fragment thereof.

16. The antibody or the antigen-binding fragment thereof according to claim 6, wherein the pharmaceutical composition comprises a pharmaceutically acceptable carrier and/or an excipient, or the pharmaceutical composition is in a form suitable for administration by subcutaneous injection, intradermal injection, intravenous injection, intramuscular injection or intralesional injection.

17. The antibody or the antigen-binding fragment thereof according to claim 15, wherein the second antibody further comprises a detectable label.

18. The antibody or the antigen-binding fragment thereof according to claim 17, wherein detectable label is a radioisotope, a luminescent substance, a colored substance, an enzyme or polyethylene glycol.

19. The method according to claim 8, wherein autoimmune diseases is plaque psoriasis or systemic lupus erythematosus, or ulcerative colitis is refractory or recurrent.

20. The method according to claim 8, wherein the subject has received conventional treatment or is inadequately responsive, unresponsive or intolerant to biological agents, and thus fails to achieve complete response or partial response.

* * * * *